(12) United States Patent
Chen et al.

(10) Patent No.: US 11,725,057 B2
(45) Date of Patent: Aug. 15, 2023

(54) AUTOIMMUNE SUPPRESSOR AND APPLICATION THEREOF

(71) Applicant: Keymed Biosciences Co., Ltd., Chengdu (CN)

(72) Inventors: Bo Chen, Chengdu (CN); Gang Xu, Chengdu (CN); Juntao Yu, Chengdu (CN)

( * ) Notice: Subject to any disclaimer, the term of this patent is extended or adjusted under 35 U.S.C. 154(b) by 0 days.

(21) Appl. No.: 16/971,774

(22) PCT Filed: May 29, 2019

(86) PCT No.: PCT/CN2019/089031
§ 371 (c)(1),
(2) Date: Aug. 21, 2020

(87) PCT Pub. No.: WO2019/228405
PCT Pub. Date: Dec. 5, 2019

(65) Prior Publication Data
US 2021/0087284 A1 Mar. 25, 2021

(30) Foreign Application Priority Data

May 29, 2018 (CN) .......................... 201810528489.8

(51) Int. Cl.
C07K 16/28 (2006.01)
A61P 37/06 (2006.01)
A61K 39/395 (2006.01)

(52) U.S. Cl.
CPC ........ *C07K 16/2866* (2013.01); *A61K 39/395* (2013.01); *A61P 37/06* (2018.01); *C07K 2317/24* (2013.01); *C07K 2317/522* (2013.01); *C07K 2317/524* (2013.01); *C07K 2317/526* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 3,773,919 A | 11/1973 | Boswell et al. |
| 4,522,811 A | 6/1985 | Eppstein et al. |
| 7,229,619 B1 | 6/2007 | Young et al. |

FOREIGN PATENT DOCUMENTS

| CN | 103739711 A | 4/2014 |
| CN | 107474134 A | 12/2017 |
| JP | 2010505418 A | 2/2010 |
| JP | 2012507294 A | 3/2012 |
| RU | 2539774 C2 | 1/2015 |
| WO | 2000064944 A1 | 11/2000 |
| WO | 2003035847 A2 | 5/2003 |
| WO | 2003038041 A2 | 5/2003 |
| WO | 2003092610 A2 | 11/2003 |
| WO | 2005062967 A2 | 7/2005 |
| WO | 2005076990 A2 | 8/2005 |
| WO | 2008151819 A2 | 12/2008 |
| WO | 2010070346 A2 | 6/2010 |
| WO | 2017114694 A1 | 7/2017 |
| WO | 2017211319 A1 | 12/2017 |

OTHER PUBLICATIONS

English Translation of the Written Opinion of the International Searching Authority of PCT/CN2019/089031 (dated Sep. 2, 2020). (Year: 2020).*
Mariuzza, R.A. et al. The Structural Basis of Antigen-Antibody Recognition1 Annu. Rev. Biophys. Biphys. Chem. 16:139-159.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 1.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Cai, Fang, et al., Bioanalytical Challenges and Improved Detection of Circulating Levels of IL-13, Bioanalysis 8(4), 323-332 (2016).
Wynn, Thomas, et al. IL-13 Effector Functions, Annu. Ref. Immunol. 21:425-56 (2003).
Brightling Christopher et al., Benralizumab for Chronic Obstructive Pulmonary Disease and Sputum Eosinphilia: A Randdomized, Double-Blind, Placebo-controlled Phase 2a Study, Lance Respir Med (2014).
Carrillo, Humberto, et al., The Multiple Sequence Alignment Problem In Biology, SIAM J. Appl. Math, vol. 48, No. Oct. 1988.
Chothis, Cyrus, et al., Canonical Structures for the Hypervariable Regions of Immunoglobulins, J. Mol. Biol. 196901-917 (1987).
Englebienne, Patrick, Use of Colloidal Gold Surface Pasmon Resonance Peak Shift to Inter Affinity Constants form the Internationsl Between Proten Antigens an Antibodies Specific for Single or Multiple Epitopes, Analyst, 123, 599 (1998).
Fahy, John, Type 2 Inflammation in Asthma—Present in Most, Absent in Many, Nat Rev Immunol 15 57-65 (2015).
Hanania, Nicola, et al., Lebrikizumab in Moderate-to-Severe Asthma: Pooled Data From Two Randomised Placedo-Controlled Studies, Thorax 70(8) 748-56 (2015).

(Continued)

*Primary Examiner* — Nora M Rooney

(57) ABSTRACT

The present disclosure relates to a dual inhibiting antibody that targets human interleukin-4 and interleukin-13, a manufacturing method therefor and use thereof.

11 Claims, 7 Drawing Sheets
Specification includes a Sequence Listing.

(56) References Cited

OTHER PUBLICATIONS

Heinzmann, A, et al., Genetic Variants of IL-13 Signalling a Human Asthma and Atopy, Hum Mol Genet 9 549-559 (2000).

Hersey, Gurjit, IL-13 Receptors and Signaling Pathways: An Evolving Web, J Allergy Clin Immunol 111(4) 677-90 (2003).

Miller, Kathy, et al., Design Construction, and In Vitro Analyses of Multivalent Antibodies, Jimmunol 170 4854-4861 (2003).

Nakamura, Yasukazu, et al., Codon Usage Tabulated from International DNA Sequence Databases: Status for the Year 2000, Nucl. Acids Res 28292 (2000).

Noonan, Michael, et al., Dose-ranging Study of Lebrikizumab in Asthmatic Patients Not Receiving Inhaled Steriods, J Allergy Clin Immunol, Sep. 2013.

Oh, C.K., et al., Investigational Therapeutics Targeting the IL-4/IL-13/STAT-6 Pathway for the Treatment of Asthma, Eur Respir Rev 19 46-54 (2010).

Welschof, Martin, et al., Recombinant Antibodies for Cancer Therapy Methods and Protocal (2003).

Rich, Rebecca et al., Advances in Surface Plasmon Resonance Biosensor Analysis, Curr Opin Biotechnol 1154 (2000).

Smith, K.A., et al.. Demystified Recombinant Antibodies, J Clin Pathol 57 912-917 (2004).

UniProtKB-P05112 (IL4_Human).

UniProtKB-P2434 (IL4RA_Human).

UniProtKB-P35225 (IL13_Human).

UniProtKB-P78552 (l13R1_Human).

UniProtKB-Q6JHZ9 (Q6JHZ9_MACFA).

Rudikoff, S., et al., Single Amino Acid Substitution Altering Antigen-binding Specificity, Immunonlogy, Proc. Natl. Acad. Sci. USA, vol. 79, pp. 1979-1983, Mar. 1982.

Smith, D.W., et al., Bioinformatics and the Genome Projects, Biocomputing Informatics and Genome Projects, Academic Press, Tibtech Oct. 1994 vol. 12, pp. 427.

Griffin, H.G., Computer Analysis of Sequence Data, Methods in Molecular Biology, vol. 24, pp. 1-8 (1994).

\* cited by examiner

SEQUENCE LISTING

<160> NUMBER OF SEQ ID NOS: 232

<210> SEQ ID NO 1
<211> LENGTH: 119
<212> TYPE: PRT

<213> ORGANISM: Mus musculus

<400> SEQUENCE: 1

Gln Val Gln Leu Gln Gln Ser Gly Thr Glu Leu Val Lys Pro Gly Ala
1               5                   10                  15
Ser Val Lys Met Ser Cys Lys Ala Ser Val Asn Thr Phe Thr Gly Tyr
            20                  25                  30
Asn Met His Trp Ile Lys Gln Thr Pro Gly Gln Gly Leu Glu Trp Ile
        35                  40                  45
Gly Gly Leu His Pro Gly Asn Gly Asp Ser Ser Tyr Asn Gln Lys Phe
    50                  55                  60
Lys Gly Arg Ala Thr Leu Thr Ala Asp Lys Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Ala Leu Thr Thr Ala Gly Arg Ala Trp Phe Pro Tyr Trp Gly Gln Gly
            100                 105                 110
Thr Leu Val Thr Val Ser Ala
        115

<210> SEQ ID NO 2
<211> LENGTH: 5
<212> TYPE: PRT
<213> ORGANISM: Mus musculus

<400> SEQUENCE: 2

Gly Tyr Asn Met His
1               5

<210> SEQ ID NO 3
<211> LENGTH: 17
<212> TYPE: PRT
<213> ORGANISM: Mus musculus

<400> SEQUENCE: 3

Gly Leu His Pro Gly Asn Gly Asp Ser Ser Tyr Asn Gln Lys Phe Lys
1               5                   10                  15
Gly

<210> SEQ ID NO 4
<211> LENGTH: 8
<212> TYPE: PRT
<213> ORGANISM: Mus musculus

<400> SEQUENCE: 4

Thr Thr Ala Gly Arg Ala Trp Phe
1               5

<210> SEQ ID NO 5
<211> LENGTH: 357
<212> TYPE: DNA
<213> ORGANISM: Mus musculus

<400> SEQUENCE: 5
caggttcagc tgcagcagtc tgggactgag ctggtgaagc ctggggcctc agtgaagatg      60
tcctgcaagg cttctgtcaa cacatttacc ggttacaata tgcactggat aaaacagaca     120
cctggacagg gcctggaatg gattggaggt cttcatccag gaaatggtga ttcttcctac     180
aatcagaagt tcaaaggcag ggccacattg actgcagaca atcctccaa cactgcctac     240

```
atgcagctca gcagcctgac atctgaggac tctgcggtct attactgtgc ccttactacg      300
gctggccggg cctggtttcc ttactggggc caagggactc tggtcactgt ctctgca         357
```

<210> SEQ ID NO 6
<211> LENGTH: 107
<212> TYPE: PRT
<213> ORGANISM: Mus musculus

<400> SEQUENCE: 6

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105
```

<210> SEQ ID NO 7
<211> LENGTH: 11
<212> TYPE: PRT
<213> ORGANISM: Mus musculus

<400> SEQUENCE: 7

```
Arg Ala Ser Gln Asp Ile Ser Asn Tyr Leu Asn
1               5                   10
```

<210> SEQ ID NO 8
<211> LENGTH: 7
<212> TYPE: PRT
<213> ORGANISM: Mus musculus

<400> SEQUENCE: 8

```
Tyr Thr Ser Arg Leu His Ser
1               5
```

<210> SEQ ID NO 9
<211> LENGTH: 9
<212> TYPE: PRT
<213> ORGANISM: Mus musculus

<400> SEQUENCE: 9

```
Gln Gln Gly Asn Thr Leu Pro Pro Thr
1               5
```

<210> SEQ ID NO 10
<211> LENGTH: 321
<212> TYPE: DNA
<213> ORGANISM: Mus musculus

<400> SEQUENCE: 10

```
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
```

```
aggttcagtg gcagtgggtc tggaacagat tattctctca ccattagcaa cctggagcaa    240
gaagatattg ccacttactt ttgccaacag ggtaatacgc ttcctccgac gttcggtgga    300
ggcaccaagc tggaaatcaa a                                               321
```

<210> SEQ ID NO 11
<211> LENGTH: 119
<212> TYPE: PRT
<213> ORGANISM: Mus musculus

<400> SEQUENCE: 11

```
Gln Val Gln Leu Gln Gln Ser Gly Ala Glu Leu Val Lys Pro Gly Ala
1               5                   10                  15

Ser Val Lys Met Ser Cys Thr Ala Thr Gly Asn Ile Phe Thr Gly Tyr
            20                  25                  30

Asn Met His Trp Ile Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Arg Ala Thr Leu Thr Ala Asp Lys Ser Ser Ser Ser Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115
```

<210> SEQ ID NO 12
<211> LENGTH: 5
<212> TYPE: PRT
<213> ORGANISM: Mus musculus

<400> SEQUENCE: 12

```
Gly Tyr Asn Met His
1               5
```

<210> SEQ ID NO 13
<211> LENGTH: 17
<212> TYPE: PRT
<213> ORGANISM: Mus musculus

<400> SEQUENCE: 13

```
Gly Leu His Pro Gly Asn Gly Asp Thr Ser Tyr Asn Gln Lys Phe Lys
1               5                   10                  15

Gly
```

<210> SEQ ID NO 14
<211> LENGTH: 8
<212> TYPE: PRT
<213> ORGANISM: Mus musculus

<400> SEQUENCE: 14

```
Thr Thr Ala Gly Arg Ala Trp Phe
1               5
```

<210> SEQ ID NO 15
<211> LENGTH: 357
<212> TYPE: DNA
<213> ORGANISM: Mus musculus

<400> SEQUENCE: 15

```
caggttcagc tgcagcagtc tggggctgaa ctggtgaagc ctggggcctc agtgaagatg      60
tcctgcacgg ctacaggcaa tatatttacc ggttataata tgcactggat aaagcagaca     120
cctggacagg gcctggaatg gattggaggt cttcatccag gaaatggtga acttcctac     180
aatcagaagt tcaaaggcag ggccacattg actgcagaca atcctccag ctcagcctac     240
atgcaactca gcagcctgac atctgaggac tctgcggtct attactgtgc ccttactacg     300
gctggccggg cctggtttgc ttactggggc caagggactc tggtcactgt ctctgca        357
```

<210> SEQ ID NO 16
<211> LENGTH: 106
<212> TYPE: PRT
<213> ORGANISM: Mus musculus

<400> SEQUENCE: 16

Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
                20                  25                  30
Leu Asn Trp Tyr Gln Gln Lys Pro Asp Gly Thr Val Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asn Thr Leu His Thr
                85                  90                  95
Phe Gly Gly Gly Thr Lys Leu Glu Ile Lys
            100                 105

<210> SEQ ID NO 17
<211> LENGTH: 11
<212> TYPE: PRT
<213> ORGANISM: Mus musculus

<400> SEQUENCE: 17

Arg Ala Ser Gln Asp Ile Ser Asn Tyr Leu Asn
1               5                   10

<210> SEQ ID NO 18
<211> LENGTH: 7
<212> TYPE: PRT
<213> ORGANISM: Mus musculus

<400> SEQUENCE: 18

Tyr Thr Ser Arg Leu His Ser
1               5

<210> SEQ ID NO 19
<211> LENGTH: 8
<212> TYPE: PRT
<213> ORGANISM: Mus musculus

<400> SEQUENCE: 19

Gln Gln Gly Asn Thr Leu His Thr
1               5

<210> SEQ ID NO 20

-continued

```
<211> LENGTH: 318
<212> TYPE: DNA
<213> ORGANISM: Mus musculus

<400> SEQUENCE: 20
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagac tacactcagg agtcccatca     180
aggttcagtg gcagtgggtc tggaacagat tattctctca ccattagcaa cctggagcaa     240
gaagatattg ccacttactt ttgccaacag ggtaatacgc ttcacacgtt cggagggggg     300
accaagctgg aaatcaaa                                                   318

<210> SEQ ID NO 21
<211> LENGTH: 119
<212> TYPE: PRT
<213> ORGANISM: Mus musculus

<400> SEQUENCE: 21

Gln Val Gln Leu Gln Gln Ser Gly Ala Glu Leu Val Lys Pro Gly Ala
1               5                   10                  15

Ser Val Lys Met Ser Cys Lys Ala Ser Val Asn Thr Phe Ala Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 22
<211> LENGTH: 5
<212> TYPE: PRT
<213> ORGANISM: Mus musculus

<400> SEQUENCE: 22

Gly Tyr Asn Met His
1               5

<210> SEQ ID NO 23
<211> LENGTH: 17
<212> TYPE: PRT
<213> ORGANISM: Mus musculus

<400> SEQUENCE: 23

Gly Leu His Pro Gly Asn Gly Asp Thr Ser Tyr Asn Gln Lys Phe Lys
1               5                   10                  15

Gly

<210> SEQ ID NO 24
<211> LENGTH: 8
<212> TYPE: PRT
<213> ORGANISM: Mus musculus
```

-continued

<400> SEQUENCE: 24

Thr Thr Ala Gly Arg Ala Trp Phe
1               5

<210> SEQ ID NO 25
<211> LENGTH: 357
<212> TYPE: DNA
<213> ORGANISM: Mus musculus

<400> SEQUENCE: 25
caggtccagc tgcagcagtc tggggctgag ctggtgaagc ctggggcctc agtgaagatg      60
tcctgcaagg cttctgtcaa cacatttgcc ggttacaata tgcactgggt aaagcagaca     120
cctggacagg gcctggaatg gattggaggt cttcatccag gaaatggtga tacttcctac     180
aatcagaagt tcaaggcaa ggccacattg actgcagaca atcctccaa cactgcctac      240 atgcagctca gcagcctgac atctgaggac tctgcggtct attactgtgc ccttactacg     300
gctggccggg cctggtttgc ttactggggc caaggactc tggtcactgt ctctgca        357

<210> SEQ ID NO 26
<211> LENGTH: 107
<212> TYPE: PRT
<213> ORGANISM: Mus musculus

<400> SEQUENCE: 26

Asp Ile Gln Met Ile Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 27
<211> LENGTH: 11
<212> TYPE: PRT
<213> ORGANISM: Mus musculus

<400> SEQUENCE: 27

Arg Ala Ser Gln Asp Ile Ser Asn Tyr Leu Asn
1               5                   10

<210> SEQ ID NO 28
<211> LENGTH: 7
<212> TYPE: PRT
<213> ORGANISM: Mus musculus

<400> SEQUENCE: 28

Tyr Thr Ser Arg Leu His Ser
1               5

<210> SEQ ID NO 29

```
<211> LENGTH: 9
<212> TYPE: PRT
<213> ORGANISM: Mus musculus

<400> SEQUENCE: 29

Gln Gln Gly Asn Thr Leu Pro Trp Thr
1               5

<210> SEQ ID NO 30
<211> LENGTH: 321
<212> TYPE: DNA
<213> ORGANISM: Mus musculus

<400> SEQUENCE: 30
gacatccaga tgattcagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaagc tggaaataaa a                                               321

<210> SEQ ID NO 31
<211> LENGTH: 119
<212> TYPE: PRT
<213> ORGANISM: Mus musculus

<400> SEQUENCE: 31

Gln Val Gln Leu Gln Gln Ser Gly Thr Glu Leu Val Lys Pro Gly Ala
1               5                   10                  15

Ser Val Lys Met Ser Cys Lys Ala Ser Val Asn Thr Phe Thr Gly Tyr
            20                  25                  30

Asn Met His Trp Ile Lys Gln Thr Pro Gly Gln Gly Leu Glu Trp Ile
        35                  40                  45

Gly Gly Leu His Pro Gly Asn Gly Asp Ser Ser Tyr Asn Gln Lys Phe
    50                  55                  60

Lys Gly Arg Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Pro Tyr Trp Gly Gln Gly
            100                 105                 110

Thr Leu Val Thr Val Ser Ala
        115

<210> SEQ ID NO 32
<211> LENGTH: 5
<212> TYPE: PRT
<213> ORGANISM: Mus musculus

<400> SEQUENCE: 32

Gly Tyr Asn Met His
1               5

<210> SEQ ID NO 33
<211> LENGTH: 17
<212> TYPE: PRT
<213> ORGANISM: Mus musculus

<400> SEQUENCE: 33
```

Gly Leu His Pro Gly Asn Gly Asp Ser Ser Tyr Asn Gln Lys Phe Lys
1               5                   10                  15

Gly

<210> SEQ ID NO 34
<211> LENGTH: 8
<212> TYPE: PRT
<213> ORGANISM: Mus musculus

<400> SEQUENCE: 34

Thr Thr Ala Gly Arg Ala Trp Phe
1               5

<210> SEQ ID NO 35
<211> LENGTH: 357
<212> TYPE: DNA
<213> ORGANISM: Mus musculus

<400> SEQUENCE: 35
caggttcagc tgcagcagtc tgggactgag ctggtgaagc ctggggcctc agtgaagatg      60
tcctgcaagg cttctgtcaa cacatttacc ggttacaata tgcactggat aaaacagaca     120
cctggacagg gcctggaatg gattggaggt cttcatccag gaaatggtga ttcttcctac     180
aatcagaagt tcaaaggcag ggccacattg actgcagaca atcctccaa cactgcctac      240 atgcagctca gcagcctgac atctgaggac tctgcggtct attactgtgc ccttactacg     300
gctggccggg cctggtttcc ttactggggc caagggactc tggtcactgt ctctgca        357

<210> SEQ ID NO 36
<211> LENGTH: 107
<212> TYPE: PRT
<213> ORGANISM: Mus musculus

<400> SEQUENCE: 36

Asp Ile Gln Met Ile Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Arg Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys
                100                 105

<210> SEQ ID NO 37
<211> LENGTH: 11
<212> TYPE: PRT
<213> ORGANISM: Mus musculus

<400> SEQUENCE: 37

Arg Ala Ser Gln Asp Ile Ser Asn Tyr Leu Asn
1               5                   10

<210> SEQ ID NO 38

<210> SEQ ID NO 38
<211> LENGTH: 7
<212> TYPE: PRT
<213> ORGANISM: Mus musculus

<400> SEQUENCE: 38

Tyr Thr Ser Arg Leu His Ser
1               5

<210> SEQ ID NO 39
<211> LENGTH: 9
<212> TYPE: PRT
<213> ORGANISM: Mus musculus

<400> SEQUENCE: 39

Gln Gln Gly Asn Thr Leu Pro Leu Thr
1               5

<210> SEQ ID NO 40
<211> LENGTH: 321
<212> TYPE: DNA
<213> ORGANISM: Mus musculus

<400> SEQUENCE: 40

```
gacatccaga tgattcagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagag gcagtgggtc tggaacagat tattctctca ccattagcaa cctggagcaa     240
gaagatattg ccacttactt ttgccaacag ggtaatacgc ttccgctcac gttcggtgct     300
gggaccaagc tggagctgaa a                                               321
```

<210> SEQ ID NO 41
<211> LENGTH: 119
<212> TYPE: PRT
<213> ORGANISM: Mus musculus

<400> SEQUENCE: 41

Gln Val Gln Leu Gln Gln Ser Gly Thr Glu Leu Val Lys Pro Gly Ala
1               5                   10                  15

Ser Val Lys Met Ser Cys Lys Ala Ser Val Asn Thr Phe Thr Gly Tyr
            20                  25                  30

Asn Met His Trp Ile Lys Gln Thr Pro Gly Gln Gly Leu Glu Trp Ile
        35                  40                  45

Gly Gly Leu His Pro Gly Asn Gly Asp Ser Ser Tyr Asn Gln Lys Phe
    50                  55                  60

Lys Gly Arg Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Pro Tyr Trp Gly Gln Gly
            100                 105                 110

Thr Leu Val Thr Val Ser Ala
        115

<210> SEQ ID NO 42
<211> LENGTH: 5
<212> TYPE: PRT
<213> ORGANISM: Mus musculus

<400> SEQUENCE: 42

Gly Tyr Asn Met His
1               5

<210> SEQ ID NO 43
<211> LENGTH: 17
<212> TYPE: PRT
<213> ORGANISM: Mus musculus

<400> SEQUENCE: 43

Gly Leu His Pro Gly Asn Gly Asp Ser Ser Tyr Asn Gln Lys Phe Lys
1               5                   10                  15

Gly

<210> SEQ ID NO 44
<211> LENGTH: 8
<212> TYPE: PRT
<213> ORGANISM: Mus musculus

<400> SEQUENCE: 44

Thr Thr Ala Gly Arg Ala Trp Phe
1               5

<210> SEQ ID NO 45
<211> LENGTH: 357
<212> TYPE: DNA
<213> ORGANISM: Mus musculus

<400> SEQUENCE: 45
caggtccagc tgcagcagtc tgggactgag ctggtgaagc ctggggcctc agtgaagatg      60
tcctgcaagg cttctgtcaa cacatttacc ggttacaata tgcactggat aaaacagaca     120
cctggacagg gcctggaatg gattggaggt cttcatccag gaaatggtga ttcttcctac     180
aatcagaagt tcaaaggcag ggccacattg actgcagaca atcctccaa cactgcctac      240 atgcagctca gcagcctgac atctgaggac tctgcggtct attactgtgc ccttactacg     300
gctggccggg cctggtttcc ttactggggc caagggactc tggtcactgt ctctgca       357

<210> SEQ ID NO 46
<211> LENGTH: 107
<212> TYPE: PRT
<213> ORGANISM: Mus musculus

<400> SEQUENCE: 46

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 47

<210> SEQ ID NO 47
<211> LENGTH: 11
<212> TYPE: PRT
<213> ORGANISM: Mus musculus

<400> SEQUENCE: 47

Arg Ala Ser Gln Asp Ile Ser Asn Tyr Leu Asn
1               5                   10

<210> SEQ ID NO 48
<211> LENGTH: 7
<212> TYPE: PRT
<213> ORGANISM: Mus musculus

<400> SEQUENCE: 48

Tyr Thr Ser Arg Leu His Ser
1               5

<210> SEQ ID NO 49
<211> LENGTH: 9
<212> TYPE: PRT
<213> ORGANISM: Mus musculus

<400> SEQUENCE: 49

Gln Gln Gly Asn Thr Leu Pro Trp Thr
1               5

<210> SEQ ID NO 50
<211> LENGTH: 320
<212> TYPE: DNA
<213> ORGANISM: Mus musculus

<400> SEQUENCE: 50

```
gacatccaga tgacccagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaagc tggaaatcaa                                                 320
```

<210> SEQ ID NO 51
<211> LENGTH: 119
<212> TYPE: PRT
<213> ORGANISM: Mus musculus

<400> SEQUENCE: 51

Gln Val Gln Leu Gln Gln Ser Gly Ala Glu Leu Val Lys Pro Gly Ala
1               5                   10                  15

Ser Val Lys Met Ser Cys Thr Ala Ser Gly Asn Ile Phe Ser Gly Tyr
                20                  25                  30

Asn Met His Trp Ile Lys Gln Thr Pro Gly Gln Gly Leu Glu Trp Ile
            35                  40                  45

Gly Gly Leu His Pro Gly Asn Gly Asp Thr Ser Tyr Asn Gln Lys Phe
        50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
                100                 105                 110

Thr Leu Val Thr Val Ser Ala
        115

<210> SEQ ID NO 52
<211> LENGTH: 5
<212> TYPE: PRT
<213> ORGANISM: Mus musculus

<400> SEQUENCE: 52

Gly Tyr Asn Met His
1               5

<210> SEQ ID NO 53
<211> LENGTH: 17
<212> TYPE: PRT
<213> ORGANISM: Mus musculus

<400> SEQUENCE: 53

Gly Leu His Pro Gly Asn Gly Asp Thr Ser Tyr Asn Gln Lys Phe Lys
1               5                   10                  15

Gly

<210> SEQ ID NO 54
<211> LENGTH: 8
<212> TYPE: PRT
<213> ORGANISM: Mus musculus

<400> SEQUENCE: 54

Thr Thr Ala Gly Arg Ala Trp Phe
1               5

<210> SEQ ID NO 55
<211> LENGTH: 357
<212> TYPE: DNA
<213> ORGANISM: Mus musculus

<400> SEQUENCE: 55
caggtccagc tgcagcagtc tggggctgag ctggtgaagc ctggggcctc agtgaagatg      60
tcctgcacgg cttcaggcaa tatatttagt ggttataata tgcactggat aaagcagaca     120
cctggacagg gcctggaatg gattggaggt cttcatccag gaaatggtga tacttcctac     180
aatcagaagt tcaaaggcaa ggccacattg actgcagaca atcctccaa cacagcctac     240 atgcaactca gcagcctgac atctgaggac tctgcggtct attactgtgc ccttactacg     300
gctggccggg cctggtttgc ttactggggc caaggactc tggtcactgt ctctgca         357

<210> SEQ ID NO 56
<211> LENGTH: 107
<212> TYPE: PRT
<213> ORGANISM: Mus musculus

<400> SEQUENCE: 56

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

```
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Leu Lys
            100                 105

<210> SEQ ID NO 57
<211> LENGTH: 11
<212> TYPE: PRT
<213> ORGANISM: Mus musculus

<400> SEQUENCE: 57

Arg Ala Ser Gln Asp Ile Ser Asn Tyr Leu Asn
1               5                   10

<210> SEQ ID NO 58
<211> LENGTH: 7
<212> TYPE: PRT
<213> ORGANISM: Mus musculus

<400> SEQUENCE: 58

Tyr Thr Ser Arg Leu His Ser
1               5

<210> SEQ ID NO 59
<211> LENGTH: 9
<212> TYPE: PRT
<213> ORGANISM: Mus musculus

<400> SEQUENCE: 59

Gln Gln Gly Asn Thr Leu Pro Trp Thr
1               5

<210> SEQ ID NO 60
<211> LENGTH: 321
<212> TYPE: DNA
<213> ORGANISM: Mus musculus

<400> SEQUENCE: 60
gatatccaga tgacacagac tacatcctcc ctgtctgcct ctctgggaga cagagtcacc        60
atcagttgca gggcaagtca ggacattagc aattatttaa actggtatca gcagaaacca       120
gatggaactg ttaaactcct gatctactac acatcaagat tacactcagg agtcccatca       180
aggttcagtg gcagtgggtc tggaacagat tattctctca ccattagcaa cctggagcaa       240
gaagatattg ccacttactt ttgccaacag ggtaatacgc ttccgtggac gttcggtgga       300
ggcaccaagc tggagctgaa a                                                 321

<210> SEQ ID NO 61
<211> LENGTH: 119
<212> TYPE: PRT
<213> ORGANISM: Mus musculus

<400> SEQUENCE: 61

Glu Val Gln Leu Gln Gln Ser Gly Ala Glu Leu Val Lys Pro Gly Ala
1               5                   10                  15

Ser Val Lys Met Ser Cys Lys Ala Ser Val Asn Ile Phe Thr Gly Tyr
            20                  25                  30

Asn Met His Trp Val Lys Gln Thr Pro Gly Gln Gly Leu Glu Trp Ile
        35                  40                  45
```

Gly Gly Leu His Pro Gly Asn Gly Asp Thr Ser Tyr Asn Gln Lys Phe
        50                  55                  60

Lys Asp Lys Ala Thr Leu Thr Ala Asp Arg Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 62
<211> LENGTH: 5
<212> TYPE: PRT
<213> ORGANISM: Mus musculus

<400> SEQUENCE: 62

Gly Tyr Asn Met His
1               5

<210> SEQ ID NO 63
<211> LENGTH: 17
<212> TYPE: PRT
<213> ORGANISM: Mus musculus

<400> SEQUENCE: 63

Gly Leu His Pro Gly Asn Gly Asp Thr Ser Tyr Asn Gln Lys Phe Lys
1               5                   10                  15

Asp

<210> SEQ ID NO 64
<211> LENGTH: 8
<212> TYPE: PRT
<213> ORGANISM: Mus musculus

<400> SEQUENCE: 64

Thr Thr Ala Gly Arg Ala Trp Phe
1               5

<210> SEQ ID NO 65
<211> LENGTH: 357
<212> TYPE: DNA
<213> ORGANISM: Mus musculus

<400> SEQUENCE: 65
gaggttcaac tgcagcagtc tggggctgag ctggtgaagc ctggggcctc agtgaagatg     60
tcctgcaagg cttctgtcaa catatttacc ggttacaata tgcactgggt aaaacagaca    120
cctggacagg gcctggaatg gattggaggt cttcatccag gaaatggtga tacttcctac    180
aatcagaagt tcaaagacaa ggccacattg actgcagaca atcctccaa cactgcctac    240 atgcagctta gcagcctgac atctgaggac tctgcggtct attactgtgc ccttactacg    300
gctggccggg cctggttttgc ttactggggc caagggactc tggtcactgt ctctgca      357

<210> SEQ ID NO 66
<211> LENGTH: 107
<212> TYPE: PRT
<213> ORGANISM: Mus musculus

<400> SEQUENCE: 66

Asp Ile Gln Met Thr Gln Thr Thr Ser Ser Leu Ser Ala Ser Leu Gly

```
                1               5                  10                 15
            Asp Arg Val Thr Ile Ser Cys Arg Ala Ser Gln Asp Ile Ser Asn Tyr
                            20                  25                  30

Leu Asn Trp Tyr Gln Gln Lys Pro Asp Gly Thr Val Lys Leu Leu Ile
                        35                  40                  45

Tyr Tyr Thr Ser Arg Leu His Ser Gly Val Pro Ser Arg Phe Ser Gly
                    50                  55                  60

Ser Gly Ser Gly Thr Asp Tyr Ser Leu Thr Ile Ser Asn Leu Glu Gln
            65                  70                  75                  80

Glu Asp Ile Ala Thr Tyr Phe Cys Gln Gln Gly Asn Thr Leu Pro Trp
                            85                  90                  95

Thr Phe Gly Gly Gly Thr Lys Leu Glu Ile Lys
                            100                 105

<210> SEQ ID NO 67
<211> LENGTH: 11
<212> TYPE: PRT
<213> ORGANISM: Mus musculus

<400> SEQUENCE: 67

Arg Ala Ser Gln Asp Ile Ser Asn Tyr Leu Asn
1               5                   10

<210> SEQ ID NO 68
<211> LENGTH: 7
<212> TYPE: PRT
<213> ORGANISM: Mus musculus

<400> SEQUENCE: 68

Tyr Thr Ser Arg Leu His Ser
1               5

<210> SEQ ID NO 69
<211> LENGTH: 9
<212> TYPE: PRT
<213> ORGANISM: Mus musculus

<400> SEQUENCE: 69

Gln Gln Gly Asn Thr Leu Pro Trp Thr
1               5

<210> SEQ ID NO 70
<211> LENGTH: 321
<212> TYPE: DNA
<213> ORGANISM: Mus musculus

<400> SEQUENCE: 70
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcagg agtcccatca      180 aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaagc tggaaatcaa a                                               321

<210> SEQ ID NO 71
<211> LENGTH: 119
<212> TYPE: PRT
<213> ORGANISM: Mus musculus
```

<400> SEQUENCE: 71

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Asn Tyr Ser Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Lys Ser Glu Asp Ser Ala Met Tyr Tyr Cys
                85                  90                  95

Ala Arg Ala Thr Ala Arg Ala Thr Glu Phe Ala Tyr Trp Gly Gln Gly
            100                 105                 110

Thr Leu Val Thr Val Ser Ala
        115

<210> SEQ ID NO 72
<211> LENGTH: 5
<212> TYPE: PRT
<213> ORGANISM: Mus musculus

<400> SEQUENCE: 72

Arg Tyr Ala Met Ser
1               5

<210> SEQ ID NO 73
<211> LENGTH: 17
<212> TYPE: PRT
<213> ORGANISM: Mus musculus

<400> SEQUENCE: 73

Thr Ile Ser Ser Gly Gly Ser Tyr Thr Asn Tyr Ser Asp Ser Val Lys
1               5                   10                  15

Gly

<210> SEQ ID NO 74
<211> LENGTH: 8
<212> TYPE: PRT
<213> ORGANISM: Mus musculus

<400> SEQUENCE: 74

Ala Thr Ala Arg Ala Thr Glu Phe
1               5

<210> SEQ ID NO 75
<211> LENGTH: 357
<212> TYPE: DNA
<213> ORGANISM: Mus musculus

<400> SEQUENCE: 75
gaggtgaagc tggtggaatc tgggggaggc ttagtgaagc ctggagggtc cctgaaactt     60
tcctgtgcag cctctggatt cactttcagt aggtatgcca tgtcttgggt tcgccagact    120
ccggagaaga ggctggagtg ggtcgcaacc attagtagtg gtggtagtta taccaactat    180
tcagacagtg tgaaggggcg attcaccatc tccagagaca atgtcaagaa caccctgtat    240
ctgcaaatga gcagtctgaa gtctgaggac tcggccatgt attactgtgc aagggcgaca    300

```
gctcgggcta cagagtttgc ttactggggc caagggactc tggtcactgt ctctgca      357
```

<210> SEQ ID NO 76
<211> LENGTH: 106
<212> TYPE: PRT
<213> ORGANISM: Mus musculus

<400> SEQUENCE: 76

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile
            100                 105

<210> SEQ ID NO 77
<211> LENGTH: 11
<212> TYPE: PRT
<213> ORGANISM: Mus musculus

<400> SEQUENCE: 77

Arg Ala Ser Gln Asp Ile Ser Asn Tyr Leu Asn
1               5                   10

<210> SEQ ID NO 78
<211> LENGTH: 7
<212> TYPE: PRT
<213> ORGANISM: Mus musculus

<400> SEQUENCE: 78

Tyr Thr Ser Arg Leu Tyr Ser
1               5

<210> SEQ ID NO 79
<211> LENGTH: 9
<212> TYPE: PRT
<213> ORGANISM: Mus musculus

<400> SEQUENCE: 79

Gln Gln Gly Asn Thr Leu Pro Pro Thr
1               5

<210> SEQ ID NO 80
<211> LENGTH: 320
<212> TYPE: DNA
<213> ORGANISM: Mus musculus

<400> SEQUENCE: 80

```
gacatccaga tgacacagtc tacatcctcc ctgtctgcct ctctgggaga cagagtcacc      60
atcagctgca gggcaagtca ggacattagc aattatttaa actggtatca gcagaaacca     120
gatggaactg ttaaactcct gatctactac acatcaagat tatactcagg agtcccatca     180
aggttcagtg gcagtgggtc tggaacagat tattctctca ccattagcaa cctggaacaa     240
```

```
gaagatattg ccacttactt ttgccaacag ggtaatacgc ttcctccgac gttcggtgga    300
ggcaccaagc tggaaatcaa                                                320
```

<210> SEQ ID NO 81
<211> LENGTH: 119
<212> TYPE: PRT
<213> ORGANISM: Mus musculus

<400> SEQUENCE: 81

```
Gln Val Gln Leu Gln Gln Ser Gly Ala Glu Leu Val Lys Pro Gly Ala
1               5                   10                  15

Ser Val Lys Met Ser Cys Lys Ala Ser Val Asn Thr Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115
```

<210> SEQ ID NO 82
<211> LENGTH: 5
<212> TYPE: PRT
<213> ORGANISM: Mus musculus

<400> SEQUENCE: 82

```
Gly Tyr Asn Met His
1               5
```

<210> SEQ ID NO 83
<211> LENGTH: 17
<212> TYPE: PRT
<213> ORGANISM: Mus musculus

<400> SEQUENCE: 83

```
Gly Leu His Pro Gly Asn Gly Asp Thr Ser Tyr Asn Gln Lys Phe Lys
1               5                   10                  15

Gly
```

<210> SEQ ID NO 84
<211> LENGTH: 8
<212> TYPE: PRT
<213> ORGANISM: Mus musculus

<400> SEQUENCE: 84

```
Thr Thr Ala Gly Arg Ala Trp Phe
1               5
```

<210> SEQ ID NO 85
<211> LENGTH: 358
<212> TYPE: DNA
<213> ORGANISM: Mus musculus

<400> SEQUENCE: 85

```
caggtccagc tgcagcagtc tggggctgaa ctggtgaagc ctggggcctc agtgaagatg    60
tcctgcaagg cttctgtcaa cacatttacc ggttacaata tgcactgggt aaagcagaca   120
cctggacagg gcctggaatg gattggaggt cttcatccag gaaatggtga tacttcctac   180
aatcagaagt tcaaaggcaa ggccacattg actgcagaca atcctccaa cactgcctac   240 atgcagctca gcagcctgac atctgaggac tctgcggtct attactgtgc ccttactacg   300
gctggccggg cctggtttgc ttactggggc caagggactc tggtcactgt ctctgcag    358
```

<210> SEQ ID NO 86
<211> LENGTH: 107
<212> TYPE: PRT
<213> ORGANISM: Mus musculus

<400> SEQUENCE: 86

```
Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 87
<211> LENGTH: 11
<212> TYPE: PRT
<213> ORGANISM: Mus musculus

<400> SEQUENCE: 87

```
Arg Ala Ser Gln Asp Ile Ser Asn Tyr Leu Asn
1               5                   10
```

<210> SEQ ID NO 88
<211> LENGTH: 7
<212> TYPE: PRT
<213> ORGANISM: Mus musculus

<400> SEQUENCE: 88

```
Tyr Thr Ser Arg Leu His Ser
1               5
```

<210> SEQ ID NO 89
<211> LENGTH: 9
<212> TYPE: PRT
<213> ORGANISM: Mus musculus

<400> SEQUENCE: 89

```
Gln Gln Gly Asn Thr Leu Pro Trp Thr
1               5
```

<210> SEQ ID NO 90
<211> LENGTH: 321
<212> TYPE: DNA

<213> ORGANISM: Mus musculus

<400> SEQUENCE: 90

```
gacatccaga tgacccagtc tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtggac gttcggtgga   300
ggcaccaagc tggaaatcaa a                                             321
```

<210> SEQ ID NO 91
<211> LENGTH: 119
<212> TYPE: PRT
<213> ORGANISM: Mus musculus

<400> SEQUENCE: 91

Glu Val Gln Leu Lys Glu Ser Gly Ala Glu Leu Val Lys Pro Gly Ala
1               5                   10                  15

Ser Val Lys Met Ser Cys Lys Ala Ser Val Asn Ile Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Asp Lys Ala Thr Leu Thr Ala Asp Arg Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 92
<211> LENGTH: 5
<212> TYPE: PRT
<213> ORGANISM: Mus musculus

<400> SEQUENCE: 92

Gly Tyr Asn Met His
1               5

<210> SEQ ID NO 93
<211> LENGTH: 17
<212> TYPE: PRT
<213> ORGANISM: Mus musculus

<400> SEQUENCE: 93

Gly Leu His Pro Gly Asn Gly Asp Thr Ser Tyr Asn Gln Lys Phe Lys
1               5                   10                  15

Asp

<210> SEQ ID NO 94
<211> LENGTH: 8
<212> TYPE: PRT
<213> ORGANISM: Mus musculus

<400> SEQUENCE: 94

Thr Thr Ala Gly Arg Ala Trp Phe
1               5

<210> SEQ ID NO 95
<211> LENGTH: 357
<212> TYPE: DNA
<213> ORGANISM: Mus musculus

<400> SEQUENCE: 95
gaggtgcagc tgaaggagtc tgggggctgag ctggtgaagc ctggggcctc agtgaagatg        60
tcctgcaagg cttctgtcaa catatttacc ggttacaata tgcactgggt aaaacagaca       120
cctggacagg gcctggaatg gattggaggt cttcatccag gaaatggtga tacttcctac       180
aatcagaagt tcaaagacaa ggccacattg actgcagaca gatcctccaa cactgcctac       240
atgcagctca gcagcctgac atctgaggac tctgcggtct attactgtgc ccttactacg       300
gctggccggg cctggtttgc ttactggggc caagggactc tggtcactgt ctctgca         357

<210> SEQ ID NO 96
<211> LENGTH: 107
<212> TYPE: PRT
<213> ORGANISM: Mus musculus

<400> SEQUENCE: 96

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Arg Leu Glu Ile Lys
            100                 105

<210> SEQ ID NO 97
<211> LENGTH: 11
<212> TYPE: PRT
<213> ORGANISM: Mus musculus

<400> SEQUENCE: 97

Arg Ala Ser Gln Asp Ile Ser Asn Tyr Leu Asn
1               5                   10

<210> SEQ ID NO 98
<211> LENGTH: 7
<212> TYPE: PRT
<213> ORGANISM: Mus musculus

<400> SEQUENCE: 98

Tyr Thr Ser Arg Leu His Ser
1               5

<210> SEQ ID NO 99
<211> LENGTH: 9
<212> TYPE: PRT

<213> ORGANISM: Mus musculus

<400> SEQUENCE: 99

Gln Gln Gly Asn Thr Leu Pro Trp Thr
1               5

<210> SEQ ID NO 100
<211> LENGTH: 321
<212> TYPE: DNA
<213> ORGANISM: Mus musculus

<400> SEQUENCE: 100

```
gacatccaga tgactcagtc tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat acactcagg  agtcccatca   180
aggttcagtg gcagtgggtc tggaacagat tattctctca ccattagcaa cctggagcaa   240
gaagatattg ccacttactt ttgccaacag ggtaatacgc ttccgtggac gttcggtgga   300
ggcaccagac tggaaataaa a                                             321
```

<210> SEQ ID NO 101
<211> LENGTH: 119
<212> TYPE: PRT
<213> ORGANISM: Mus musculus

<400> SEQUENCE: 101

Gln Val Gln Leu Lys Gln Ser Gly Ala Glu Leu Val Lys Pro Gly Ala
1               5                   10                  15

Ser Val Lys Met Ser Cys Thr Ala Ser Gly Asn Ile Phe Ser Gly Tyr
            20                  25                  30

Asn Met His Trp Ile Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 102
<211> LENGTH: 5
<212> TYPE: PRT
<213> ORGANISM: Mus musculus

<400> SEQUENCE: 102

Gly Tyr Asn Met His
1               5

<210> SEQ ID NO 103
<211> LENGTH: 17
<212> TYPE: PRT
<213> ORGANISM: Mus musculus

<400> SEQUENCE: 103

Gly Leu His Pro Gly Asn Gly Asp Thr Ser Tyr Asn Gln Lys Phe Lys 1               5                   10                  15

Gly

<210> SEQ ID NO 104
<211> LENGTH: 8
<212> TYPE: PRT
<213> ORGANISM: Mus musculus

<400> SEQUENCE: 104

Thr Thr Ala Gly Arg Ala Trp Phe
1               5

<210> SEQ ID NO 105
<211> LENGTH: 357
<212> TYPE: DNA
<213> ORGANISM: Mus musculus

<400> SEQUENCE: 105
caggtccagc tgaagcagtc tggggctgag ctggtgaagc ctggggcctc agtgaagatg      60
tcctgcacgg cttcaggcaa tatatttagt ggttataata tgcactggat aaagcagaca     120
cctggacagg gcctggaatg gattggaggt cttcatccag gaaatggtga tacttcctac     180
aatcagaagt tcaaaggcaa ggccacattg actgcagaca atcctccaa cacagcctac      240 atgcaactca gcagcctgac atctgaggac tctgcggtct attactgtgc ccttactacg     300
gctggccggg cctggtttgc ttactggggc caagggactc tggtcactgt ctctgca        357

<210> SEQ ID NO 106
<211> LENGTH: 107
<212> TYPE: PRT
<213> ORGANISM: Mus musculus

<400> SEQUENCE: 106

Asp Ile Gln Met Asn Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Ile Lys Leu Leu Ile
            35                  40                  45

Tyr Tyr Thr Ser Arg Leu Tyr Ser Gly Val Pro Ser Arg Phe Ser Gly
        50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Asn Thr Ile Pro Tyr
                85                  90                  95

Thr Phe Gly Gly Gly Thr Lys Leu Glu Ile Lys
            100                 105

<210> SEQ ID NO 107
<211> LENGTH: 11
<212> TYPE: PRT
<213> ORGANISM: Mus musculus

<400> SEQUENCE: 107

Arg Ala Ser Gln Asp Ile Ser Asn Tyr Leu Asn
1               5                   10

<210> SEQ ID NO 108
<211> LENGTH: 7
<212> TYPE: PRT

<213> ORGANISM: Mus musculus

<400> SEQUENCE: 108

Tyr Thr Ser Arg Leu Tyr Ser
1               5

<210> SEQ ID NO 109
<211> LENGTH: 9
<212> TYPE: PRT
<213> ORGANISM: Mus musculus

<400> SEQUENCE: 109

Gln Gln Gly Asn Thr Ile Pro Tyr Thr
1               5

<210> SEQ ID NO 110
<211> LENGTH: 321
<212> TYPE: DNA
<213> ORGANISM: Mus musculus

<400> SEQUENCE: 110

```
gacatccaga tgaaccagtc tacatcctcc ctgtctgcct ctctgggaga cagagtcacc    60
atcagttgca gggcaagtca ggacattagc aattatttaa actggtatca gcagaaacca   120
gatggaacca ttaaactcct gatctactac acatcaagat tatactcagg agtcccatca   180
aggttcagtg gcagtgggtc tggaacagat tattctctca ccattagcaa cctggaggaa   240
gaagatattg ccacttattt ttgccaacag ggtaatacga ttccgtacac gttcggaggg   300
gggaccaagc tggaaatcaa a                                             321
```

<210> SEQ ID NO 111
<211> LENGTH: 119
<212> TYPE: PRT
<213> ORGANISM: Mus musculus

<400> SEQUENCE: 111

Glu Val Gln Leu Gln Gln Ser Gly Ala Glu Leu Val Lys Pro Gly Ala
1               5                   10                  15

Ser Val Lys Met Ser Cys Lys Ala Ser Val Asn Ile Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Asp Lys Ala Thr Leu Thr Ala Asp Arg Ser Ser Asn Thr Ala Tyr
65                  70                  75                  80

Met Gln Leu Ser Ser Leu Thr Ser Glu Asp Ser Ala Val Tyr Tyr Cys
            85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 112
<211> LENGTH: 5
<212> TYPE: PRT
<213> ORGANISM: Mus musculus

<400> SEQUENCE: 112

Gly Tyr Asn Met His

-continued

```
<210> SEQ ID NO 113
<211> LENGTH: 17
<212> TYPE: PRT
<213> ORGANISM: Mus musculus

<400> SEQUENCE: 113

Gly Leu His Pro Gly Asn Gly Asp Thr Ser Tyr Asn Gln Lys Phe Lys
1               5                   10                  15

Asp

<210> SEQ ID NO 114
<211> LENGTH: 8
<212> TYPE: PRT
<213> ORGANISM: Mus musculus

<400> SEQUENCE: 114

Thr Thr Ala Gly Arg Ala Trp Phe
1               5

<210> SEQ ID NO 115
<211> LENGTH: 357
<212> TYPE: DNA
<213> ORGANISM: Mus musculus

<400> SEQUENCE: 115
gaggttcaac tgcagcagtc tggggctgag ctggtgaagc ctggggcctc agtgaagatg     60
tcctgcaagg cttctgtcaa catatttacc ggttacaata tgcactgggt aaaacagaca    120
cctggacagg gcctggaatg gattggaggt cttcatccag gaaatggtga tacttcctac    180
aatcagaagt tcaagacaa  ggccacattg actgcagaca atcctccaa  cactgcctac    240 atgcagctca gcagcctgac atctgaggac tctgcggtct attactgtgc ccttactacg    300
gctggccggg cctggtttgc ttactggggc caagggactc tggtcactgt ctctgca      357

<210> SEQ ID NO 116
<211> LENGTH: 107
<212> TYPE: PRT
<213> ORGANISM: Mus musculus

<400> SEQUENCE: 116

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 117
<211> LENGTH: 11
<212> TYPE: PRT
```

<210> SEQ ID NO 117
<211> LENGTH: 11
<212> TYPE: PRT
<213> ORGANISM: Mus musculus

<400> SEQUENCE: 117

Arg Ala Ser Gln Asp Ile Ser Asn Tyr Leu Asn
1               5                   10

<210> SEQ ID NO 118
<211> LENGTH: 7
<212> TYPE: PRT
<213> ORGANISM: Mus musculus

<400> SEQUENCE: 118

Tyr Thr Ser Arg Leu His Ser
1               5

<210> SEQ ID NO 119
<211> LENGTH: 9
<212> TYPE: PRT
<213> ORGANISM: Mus musculus

<400> SEQUENCE: 119

Gln Gln Gly Asn Thr Leu Pro Trp Thr
1               5

<210> SEQ ID NO 120
<211> LENGTH: 321
<212> TYPE: DNA
<213> ORGANISM: Mus musculus

<400> SEQUENCE: 120
gacatccaga tgacacagtc tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccttggac gttcggtgga   300
ggcaccaagc tggaaataaa a                                              321

<210> SEQ ID NO 121
<211> LENGTH: 119
<212> TYPE: PRT
<213> ORGANISM: Mus musculus

<400> SEQUENCE: 121

Glu Val Gln Leu Gln Gln Ser Gly Ala Glu Leu Val Lys Pro Gly Ala
1               5                   10                  15

Ser Val Lys Met Ser Cys Lys Ala Ser Val Asn Ile Phe Thr Ser Tyr
                20                  25                  30

Asn Met His Trp Val Lys Gln Thr Pro Gly Gln Gly Leu Glu Trp Ile
            35                  40                  45

Gly Gly Leu His Pro Gly Asn Gly Asp Thr Ser Tyr Asn Gln Asn Phe
        50                  55                  60

Lys Gly Lys Ala Thr Leu Thr Ala Asp Lys Ser Ser Ser Thr Ala Tyr
65                  70                  75                  80

Met Gln Val Ser Asn Leu Thr Ser Glu Asp Ser Ala Val Tyr Tyr Cys
                85                  90                  95

Val Leu Thr Thr Ala Gly Arg Ala Trp Phe Ala Tyr Trp Gly Gln Gly
                100                 105                 110

Thr Leu Val Thr Val Ser Ala

<210> SEQ ID NO 122
<211> LENGTH: 5
<212> TYPE: PRT
<213> ORGANISM: Mus musculus

<400> SEQUENCE: 122

Ser Tyr Asn Met His
1               5

<210> SEQ ID NO 123
<211> LENGTH: 17
<212> TYPE: PRT
<213> ORGANISM: Mus musculus

<400> SEQUENCE: 123

Gly Leu His Pro Gly Asn Gly Asp Thr Ser Tyr Asn Gln Asn Phe Lys
1               5                   10                  15

Gly

<210> SEQ ID NO 124
<211> LENGTH: 8
<212> TYPE: PRT
<213> ORGANISM: Mus musculus

<400> SEQUENCE: 124

Thr Thr Ala Gly Arg Ala Trp Phe
1               5

<210> SEQ ID NO 125
<211> LENGTH: 357
<212> TYPE: DNA
<213> ORGANISM: Mus musculus

<400> SEQUENCE: 125
gaggttcaac tgcagcagtc tggggctgag ctggtgaagc ctggggcctc agtgaagatg      60
tcttgcaagg cttctgtcaa catatttacc agttacaata tgcactgggt aaaacagaca     120
cctggacagg gcctggaatg gattggaggt cttcatccag gaaatggtga tacttcctac     180
aatcagaact tcaaaggcaa ggccacattg actgcagaca atcctccag cactgcctac      240 atgcaggtca gcaacctgac atctgaggac tctgcggtct attactgtgt ccttactacg     300
gctggccggg cctggtttgc ttactggggc caagggactc tggtcactgt ctctgca       357

<210> SEQ ID NO 126
<211> LENGTH: 107
<212> TYPE: PRT
<213> ORGANISM: Mus musculus

<400> SEQUENCE: 126

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 127
<211> LENGTH: 11
<212> TYPE: PRT
<213> ORGANISM: Mus musculus

<400> SEQUENCE: 127

Arg Ala Ser Gln Asp Ile Ser Asn Tyr Leu Asn
1               5                   10

<210> SEQ ID NO 128
<211> LENGTH: 7
<212> TYPE: PRT
<213> ORGANISM: Mus musculus

<400> SEQUENCE: 128

Tyr Thr Ser Arg Leu His Ser
1               5

<210> SEQ ID NO 129
<211> LENGTH: 9
<212> TYPE: PRT
<213> ORGANISM: Mus musculus

<400> SEQUENCE: 129

Gln Gln Gly Asn Thr Leu Pro Trp Thr
1               5

<210> SEQ ID NO 130
<211> LENGTH: 321
<212> TYPE: DNA
<213> ORGANISM: Mus musculus

<400> SEQUENCE: 130
gacatccaga tgacacagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcagg agtcccatca      180 aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaagc tggaaatcaa a                                               321

<210> SEQ ID NO 131
<211> LENGTH: 119
<212> TYPE: PRT
<213> ORGANISM: Mus musculus

<400> SEQUENCE: 131

Gln Val Gln Leu Gln Glu Ser Gly Ala Glu Leu Val Lys Pro Gly Ala
1               5                   10                  15

Ser Val Lys Met Ser Cys Lys Ala Ser Val Asn Thr Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

```
Lys Gly Lys Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 132
<211> LENGTH: 5
<212> TYPE: PRT
<213> ORGANISM: Mus musculus

<400> SEQUENCE: 132

Gly Tyr Asn Met His
1               5

<210> SEQ ID NO 133
<211> LENGTH: 17
<212> TYPE: PRT
<213> ORGANISM: Mus musculus

<400> SEQUENCE: 133

Gly Leu His Pro Gly Asn Gly Asp Thr Ser Tyr Asn Gln Lys Phe Lys
1               5                   10                  15

Gly

<210> SEQ ID NO 134
<211> LENGTH: 8
<212> TYPE: PRT
<213> ORGANISM: Mus musculus

<400> SEQUENCE: 134

Thr Thr Ala Gly Arg Ala Trp Phe
1               5

<210> SEQ ID NO 135
<211> LENGTH: 357
<212> TYPE: DNA
<213> ORGANISM: Mus musculus

<400> SEQUENCE: 135
caggtgcagc tgcaggagtc tggggctgaa ctggtgaagc ctggggcctc agtgaagatg      60
tcctgcaagg cttctgtcaa cacatttacc ggttacaata tgcactgggt aaagcagaca     120
cctggacagg gcctggaatg gattggaggt cttcatccag gaaatggtga tacttcctac     180
aatcagaagt tcaaaggcaa ggccacattg actgcagaca atcctccaa cactgcctac      240 atgcagctca gcagcctgac atctgaggac tctgcggtct attactgtgc ccttactacg     300
gctggccggg cctggttttgc ttactggggc caagggactc tggtcactgt ctctgca       357

<210> SEQ ID NO 136
<211> LENGTH: 107
<212> TYPE: PRT
<213> ORGANISM: Mus musculus

<400> SEQUENCE: 136

Asp Ile Gln Met Thr Gln Thr Thr Ser Ser Leu Ser Ala Ser Leu Gly
1               5                   10                  15
```

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Val Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 137
<211> LENGTH: 11
<212> TYPE: PRT
<213> ORGANISM: Mus musculus

<400> SEQUENCE: 137

Arg Ala Ser Gln Asp Ile Ser Asn Tyr Leu Asn
1               5                   10

<210> SEQ ID NO 138
<211> LENGTH: 7
<212> TYPE: PRT
<213> ORGANISM: Mus musculus

<400> SEQUENCE: 138

Tyr Thr Ser Arg Leu His Ser
1               5

<210> SEQ ID NO 139
<211> LENGTH: 9
<212> TYPE: PRT
<213> ORGANISM: Mus musculus

<400> SEQUENCE: 139

Gln Gln Gly Asn Thr Leu Pro Trp Thr
1               5

<210> SEQ ID NO 140
<211> LENGTH: 321
<212> TYPE: DNA
<213> ORGANISM: Mus musculus

<400> SEQUENCE: 140
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatgttg ccacttactt ttgccaacag ggtaatacgc ttccgtggac gttcggtgga     300
ggcaccaagc tggaaataaa a                                               321

<210> SEQ ID NO 141
<211> LENGTH: 119
<212> TYPE: PRT
<213> ORGANISM: Mus musculus

<400> SEQUENCE: 141

Gln Val Gln Leu Lys Gln Ser Gly Ala Glu Leu Val Lys Pro Gly Ala
1               5                   10                  15

Ser Val Lys Met Ser Cys Lys Ala Ser Val Asn Thr Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 142
<211> LENGTH: 5
<212> TYPE: PRT
<213> ORGANISM: Mus musculus

<400> SEQUENCE: 142

Gly Tyr Asn Met His
1               5

<210> SEQ ID NO 143
<211> LENGTH: 17
<212> TYPE: PRT
<213> ORGANISM: Mus musculus

<400> SEQUENCE: 143

Gly Leu His Pro Gly Asn Gly Asp Thr Ser Tyr Asn Gln Lys Phe Lys
1               5                   10                  15

Gly

<210> SEQ ID NO 144
<211> LENGTH: 8
<212> TYPE: PRT
<213> ORGANISM: Mus musculus

<400> SEQUENCE: 144

Thr Thr Ala Gly Arg Ala Trp Phe
1               5

<210> SEQ ID NO 145
<211> LENGTH: 357
<212> TYPE: DNA
<213> ORGANISM: Mus musculus

<400> SEQUENCE: 145
caggtccagc tgaagcagtc tggggctgaa ctggtgaagc ctggggcctc agtgaagatg      60
tcctgcaagg cttctgtcaa cacatttacc ggttacaata tgcactgggt aaagcagaca     120
cctggacagg gcctggaatg gattggaggt cttcatccag gaaatggtga tacttcctac     180
aatcagaagt tcaaaggcaa ggccacattg actgcagaca atcctccaa cactgcctac      240 atgcagctca gcagcctgac atctgaggac tctgcggtct attactgtgc ccttactacg     300
gctggccggg cctggtttgc ttactggggc caagggactc tggtcactgt ctctgca        357

<210> SEQ ID NO 146
<211> LENGTH: 107
<212> TYPE: PRT
<213> ORGANISM: Mus musculus

<400> SEQUENCE: 146

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 147
<211> LENGTH: 11
<212> TYPE: PRT
<213> ORGANISM: Mus musculus

<400> SEQUENCE: 147

Arg Ala Ser Gln Asp Ile Ser Asn Tyr Leu Asn
1               5                   10

<210> SEQ ID NO 148
<211> LENGTH: 7
<212> TYPE: PRT
<213> ORGANISM: Mus musculus

<400> SEQUENCE: 148

Tyr Thr Ser Arg Leu His Ser
1               5

<210> SEQ ID NO 149
<211> LENGTH: 9
<212> TYPE: PRT
<213> ORGANISM: Mus musculus

<400> SEQUENCE: 149

Gln Gln Gly Asn Thr Leu Pro Trp Thr
1               5

<210> SEQ ID NO 150
<211> LENGTH: 321
<212> TYPE: DNA
<213> ORGANISM: Mus musculus

<400> SEQUENCE: 150
gacatccaga tgacacagtc tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtggac gttcggtgga     300
ggcaccaagc tggaaatcaa a                                              321

<210> SEQ ID NO 151
<211> LENGTH: 119
<212> TYPE: PRT
<213> ORGANISM: Mus musculus

<400> SEQUENCE: 151

Gln Val Gln Leu Lys Gln Ser Gly Ala Glu Leu Val Lys Pro Gly Ala
1               5                   10                  15

Ser Val Lys Met Ser Cys Thr Ala Ser Gly Asn Ile Phe Ser Gly Tyr
            20                  25                  30

Asn Met His Trp Ile Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115

<210> SEQ ID NO 152
<211> LENGTH: 5
<212> TYPE: PRT
<213> ORGANISM: Mus musculus

<400> SEQUENCE: 152

Gly Tyr Asn Met His
1               5

<210> SEQ ID NO 153
<211> LENGTH: 17
<212> TYPE: PRT
<213> ORGANISM: Mus musculus

<400> SEQUENCE: 153

Gly Leu His Pro Gly Asn Gly Asp Thr Ser Tyr Asn Gln Lys Phe Lys
1               5                   10                  15

Gly

<210> SEQ ID NO 154
<211> LENGTH: 8
<212> TYPE: PRT
<213> ORGANISM: Mus musculus

<400> SEQUENCE: 154

Thr Thr Ala Gly Arg Ala Trp Phe
1               5

<210> SEQ ID NO 155
<211> LENGTH: 357
<212> TYPE: DNA
<213> ORGANISM: Mus musculus

<400> SEQUENCE: 155
caggtccagc tgaagcagtc tggggctgag ctggtgaagc ctggggcctc agtgaagatg    60

```
tcctgcacgg cttcaggcaa tatatttagt ggttataata tgcactggat aaagcagaca      120
cctggacagg gcctggaatg gattggaggt cttcatccag gaaatggtga tacttcctac      180
aatcagaagt tcaaaggcaa ggccacattg actgcagaca atcctccaa cacagcctac       240 atgcaactca gcagcctgac atctgaggac tctgcggtct attactgtgc ccttactacg      300
gctggccggg cctggtttgc ttactggggc caagggactc tggtcactgt ctctgca         357
```

```
<210> SEQ ID NO 156
<211> LENGTH: 107
<212> TYPE: PRT
<213> ORGANISM: Mus musculus

<400> SEQUENCE: 156
```

Asp Ile Gln Met Asn Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Ile Lys Leu Leu Ile
            35                  40                  45

Tyr Tyr Thr Ser Arg Leu Tyr Ser Gly Val Pro Ser Arg Phe Ser Gly
50                  55                  60

Ser Gly Ser Gly Thr Asp Tyr Ser Leu Thr Ile Ser Asn Leu Glu Glu
65                  70                  75                  80

Glu Asp Ile Ala Thr Tyr Phe Cys Gln Gln Gly Asn Thr Ile Pro Tyr
                85                  90                  95

Thr Phe Gly Gly Gly Thr Lys Leu Glu Ile Lys
            100                 105

```
<210> SEQ ID NO 157
<211> LENGTH: 11
<212> TYPE: PRT
<213> ORGANISM: Mus musculus

<400> SEQUENCE: 157
```

Arg Ala Ser Gln Asp Ile Ser Asn Tyr Leu Asn
1               5                   10

```
<210> SEQ ID NO 158
<211> LENGTH: 7
<212> TYPE: PRT
<213> ORGANISM: Mus musculus

<400> SEQUENCE: 158
```

Tyr Thr Ser Arg Leu Tyr Ser
1               5

```
<210> SEQ ID NO 159
<211> LENGTH: 9
<212> TYPE: PRT
<213> ORGANISM: Mus musculus

<400> SEQUENCE: 159
```

Gln Gln Gly Asn Thr Ile Pro Tyr Thr
1               5

```
<210> SEQ ID NO 160
<211> LENGTH: 321
<212> TYPE: DNA
<213> ORGANISM: Mus musculus
```

-continued

<400> SEQUENCE: 160

```
gacatccaga tgaaccagtc tacatcctcc ctgtctgcct ctctgggaga cagagtcacc      60
atcagttgca gggcaagtca ggacattagc aattatttaa actggtatca gcagaaacca     120
gatggaacca ttaaactcct gatctactac acatcaagat tatactcagg agtcccatca     180
aggttcagtg gcagtgggtc tggaacagat tattctctca ccattagcaa cctggaggaa     240
gaagatattg ccacttattt ttgccaacag ggtaatacga ttccgtacac gttcggaggg     300
gggaccaagc tggaaatcaa a                                                321
```

<210> SEQ ID NO 161
<211> LENGTH: 119
<212> TYPE: PRT
<213> ORGANISM: Mus musculus

<400> SEQUENCE: 161

```
Gln Val Gln Leu Gln Gln Ser Gly Ala Glu Leu Val Lys Pro Gly Ala
1               5                   10                  15

Ser Val Lys Met Ser Cys Lys Ala Ser Val Asn Ile Phe Thr Gly Tyr
            20                  25                  30

Asn Met His Trp Val Lys Gln Thr Pro Gly Gln Gly Leu Glu Trp Ile
        35                  40                  45

Gly Gly Leu His Pro Gly Asn Gly Asp Thr Ser Tyr Asn Gln Lys Phe
    50                  55                  60

Lys Asp Lys Ala Thr Leu Thr Ala Asp Arg Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ala
        115
```

<210> SEQ ID NO 162
<211> LENGTH: 5
<212> TYPE: PRT
<213> ORGANISM: Mus musculus

<400> SEQUENCE: 162

```
Gly Tyr Asn Met His
1               5
```

<210> SEQ ID NO 163
<211> LENGTH: 17
<212> TYPE: PRT
<213> ORGANISM: Mus musculus

<400> SEQUENCE: 163

```
Gly Leu His Pro Gly Asn Gly Asp Thr Ser Tyr Asn Gln Lys Phe Lys
1               5                   10                  15

Asp
```

<210> SEQ ID NO 164
<211> LENGTH: 8
<212> TYPE: PRT
<213> ORGANISM: Mus musculus

<400> SEQUENCE: 164

```
Thr Thr Ala Gly Arg Ala Trp Phe
1               5
```

```
<210> SEQ ID NO 165
<211> LENGTH: 358
<212> TYPE: DNA
<213> ORGANISM: Mus musculus

<400> SEQUENCE: 165
caggtccagc tgcagcagtc tggggctgag ctggtgaagc ctggggcctc agtgaagatg      60
tcctgcaagg cttctgtcaa catatttacc ggttacaata tgcactgggt aaaacagaca     120
cctggacagg gcctggaatg gattggaggt cttcatccag gaaatggtga tacttcctac     180
aatcagaagt tcaaagacaa ggccacattg actgcagaca tcctccaa cactgcctac       240 atgcagctca gcagcctgac atctgaggac tctgcggtct attactgtgc ccttactacg     300
gctggccggg cctggtttgc ttactggggc caagggactc tggtcactgt ctctgcag      358

<210> SEQ ID NO 166
<211> LENGTH: 108
<212> TYPE: PRT
<213> ORGANISM: Mus musculus

<400> SEQUENCE: 166

Asp Ile Lys Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Trp Thr Phe Gly Gly Gly Thr Lys Leu Glu Ile Lys
            100                 105

<210> SEQ ID NO 167
<211> LENGTH: 11
<212> TYPE: PRT
<213> ORGANISM: Mus musculus

<400> SEQUENCE: 167

Arg Ala Ser Gln Asp Ile Ser Asn Tyr Leu Asn
1               5                   10

<210> SEQ ID NO 168
<211> LENGTH: 7
<212> TYPE: PRT
<213> ORGANISM: Mus musculus

<400> SEQUENCE: 168

Tyr Thr Ser Arg Leu His Ser
1               5

<210> SEQ ID NO 169
<211> LENGTH: 10
<212> TYPE: PRT
<213> ORGANISM: Mus musculus
```

<400> SEQUENCE: 169

Gln Gln Gly Asn Thr Leu Pro Pro Trp Thr
1               5                   10

<210> SEQ ID NO 170
<211> LENGTH: 324
<212> TYPE: DNA
<213> ORGANISM: Mus musculus

<400> SEQUENCE: 170

```
gacatcaaga tgacccagtc tacatcctcc ctgtctgcct ctctgggaga cagagtcacc     60
atcagttgca gggcaagtca ggacattagc aattatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttcctccgtg gacgttcggt    300
ggaggcacca agctggaaat caaa                                           324
```

<210> SEQ ID NO 171
<211> LENGTH: 119
<212> TYPE: PRT
<213> ORGANISM: Homo sapiens

<400> SEQUENCE: 171

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Asn Tyr Ala Asp Ser Val
    50                  55                  60

Lys Gly Arg Phe Thr Ile Ser Arg Asp Asn Val Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Ala Arg Ala Thr Glu Phe Ala Tyr Trp Gly Gln Gly
            100                 105                 110

Thr Leu Val Thr Val Ser Ser
        115

<210> SEQ ID NO 172
<211> LENGTH: 5
<212> TYPE: PRT
<213> ORGANISM: Homo sapiens

<400> SEQUENCE: 172

Arg Tyr Ala Met Ser
1               5

<210> SEQ ID NO 173
<211> LENGTH: 17
<212> TYPE: PRT
<213> ORGANISM: Homo sapiens

<400> SEQUENCE: 173

Thr Ile Ser Ser Gly Gly Ser Tyr Thr Asn Tyr Ala Asp Ser Val Lys
1               5                   10                  15

<210> SEQ ID NO 174
<211> LENGTH: 8
<212> TYPE: PRT
<213> ORGANISM: Homo sapiens

<400> SEQUENCE: 174

Ala Thr Ala Arg Ala Thr Glu Phe
1               5

<210> SEQ ID NO 175
<211> LENGTH: 357
<212> TYPE: DNA
<213> ORGANISM: Homo sapiens

<400> SEQUENCE: 175

```
gaggtgcagc tggttgaatc tggcggagga ctggttaagc ctggcggctc tctgagactg      60
tcttgtgccg cttctggctt caccttcagc agatacgcca tgagctgggt ccgacaggct     120
cctggcaaag gactggaatg ggtgtccaca atcagcagcg gcggcagcta cacaaactac     180
gccgatagcg tgaagggcag attcaccatc tccagagaca cgtgaagaa cacccctgtac     240 ctgcagatga acagcctgag agccgaggac accgccgtgt actactgtgc cagagccaca     300
gccagagcta ccgagtttgc ttactggggc cagggcacac tggtcaccgt ttcttct       357
```

<210> SEQ ID NO 176
<211> LENGTH: 119
<212> TYPE: PRT
<213> ORGANISM: Homo sapiens

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Asn Tyr Ala Asp Ser Val
    50                  55                  60

Lys Gly Arg Phe Thr Ile Ser Arg Asp Asn Val Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Ala Arg Ala Thr Glu Phe Ala Tyr Trp Gly Gln Gly
            100                 105                 110

Thr Leu Val Thr Val Ser Ser
        115

<210> SEQ ID NO 177
<211> LENGTH: 5
<212> TYPE: PRT
<213> ORGANISM: Homo sapiens

<400> SEQUENCE: 177

Arg Tyr Ala Met Ser
1               5

<210> SEQ ID NO 178
<211> LENGTH: 17

<212> TYPE: PRT
<213> ORGANISM: Homo sapiens

<400> SEQUENCE: 178

Thr Ile Ser Ser Gly Gly Ser Tyr Thr Asn Tyr Ala Asp Ser Val Lys
1               5                   10                  15

Gly

<210> SEQ ID NO 179
<211> LENGTH: 8
<212> TYPE: PRT
<213> ORGANISM: Homo sapiens

<400> SEQUENCE: 179

Ala Thr Ala Arg Ala Thr Glu Phe
1               5

<210> SEQ ID NO 180
<211> LENGTH: 357
<212> TYPE: DNA
<213> ORGANISM: Homo sapiens

<400> SEQUENCE: 180

```
gaagtgcagc tgctggaatc tggcggagga ctggttcaac ctggcggctc tctgagactg      60
tcttgtgccg cttctggctt caccttcagc agatacgcca tgagctgggt ccgacaggct     120
cctggcaaag gactggaatg ggtgtccaca atcagcagcg gcggcagcta cacaaactac     180
gccgatagcg tgaagggcag attcaccatc tccagagaca cgtgaagaa caccctgtac      240 ctgcagatga acagcctgag agccgaggac accgccgtgt actactgtgc cagagccaca     300
gccagagcta ccgagtttgc ttactggggc cagggcacac tggtcaccgt ttcttct        357
```

<210> SEQ ID NO 181
<211> LENGTH: 119
<212> TYPE: PRT
<213> ORGANISM: Homo sapiens

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Gly Tyr
                20                  25                  30

Asn Met His Trp Ile Gln Gln Ser Pro Gly Gln Gly Leu Glu Trp Met
            35                  40                  45

Gly Gly Leu His Pro Gly Asn Gly Asp Ser Ser Tyr Asn Gln Lys Phe
        50                  55                  60

Gln Gly Arg Val Thr Leu Thr Asp Lys Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ala Leu Thr Thr Ala Gly Arg Ala Trp Phe Pro Tyr Trp Gly Gln Gly
                100                 105                 110

Thr Leu Val Thr Val Ser Ser
        115

<210> SEQ ID NO 182
<211> LENGTH: 5
<212> TYPE: PRT
<213> ORGANISM: Homo sapiens

```
<400> SEQUENCE: 182

Gly Tyr Asn Met His
1               5

<210> SEQ ID NO 183
<211> LENGTH: 17
<212> TYPE: PRT
<213> ORGANISM: Homo sapiens

<400> SEQUENCE: 183

Gly Leu His Pro Gly Asn Gly Asp Ser Ser Tyr Asn Gln Lys Phe Gln
1               5                   10                  15

Gly

<210> SEQ ID NO 184
<211> LENGTH: 8
<212> TYPE: PRT
<213> ORGANISM: Homo sapiens

<400> SEQUENCE: 184

Thr Thr Ala Gly Arg Ala Trp Phe
1               5

<210> SEQ ID NO 185
<211> LENGTH: 357
<212> TYPE: DNA
<213> ORGANISM: Homo sapiens

<400> SEQUENCE: 185
caggttcagc tggttcagtc tggcgccgaa gtgaagaaac ctggcgcctc tgtgaaggtg      60
tcctgcaagg ctagcggcaa cacattcacc ggctacaaca tgcattggat ccagcagagc     120
cctggacagg gcctcgaatg gatgggagga ctgcatcctg caacggcga cagcagctac      180 aaccagaaat tccagggcag agtgaccctg accgccgaca gtctagcaa caccgcctac      240 atggaactga gcagcctgag aagcgaggac accgccgtgt actactgtgc ccttacaaca     300
gccggcagag cctggtttcc ttactgggga cagggaaccc tggtcaccgt tagctct       357

<210> SEQ ID NO 186
<211> LENGTH: 119
<212> TYPE: PRT
<213> ORGANISM: Homo sapiens

<400> SEQUENCE: 186

Gln Val Gln Leu Val Gln Ser Gly Ala Glu Val Lys Lys Pro Gly Ala
1               5                   10                  15

Ser Val Lys Met Ser Cys Lys Ala Ser Val Tyr Thr Phe Thr Gly Tyr
                20                  25                  30

Asn Met His Trp Ile Gln Gln Ser Pro Gly Gln Gly Leu Glu Trp Ile
            35                  40                  45

Gly Gly Leu His Pro Gly Asn Gly Asp Ser Ser Tyr Asn Gln Lys Phe
        50                  55                  60

Lys Gly Arg Ala Thr Leu Thr Ala Asp Lys Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ala Leu Thr Thr Ala Gly Arg Ala Trp Phe Pro Tyr Trp Gly Gln Gly
                100                 105                 110

Thr Leu Val Thr Val Ser Ser
```

115

<210> SEQ ID NO 187
<211> LENGTH: 5
<212> TYPE: PRT
<213> ORGANISM: Homo sapiens

<400> SEQUENCE: 187

Gly Tyr Asn Met His
1               5

<210> SEQ ID NO 188
<211> LENGTH: 17
<212> TYPE: PRT
<213> ORGANISM: Homo sapiens

<400> SEQUENCE: 188

Gly Leu His Pro Gly Asn Gly Asp Ser Ser Tyr Asn Gln Lys Phe Lys
1               5                   10                  15

Gly

<210> SEQ ID NO 189
<211> LENGTH: 8
<212> TYPE: PRT
<213> ORGANISM: Homo sapiens

<400> SEQUENCE: 189

Thr Thr Ala Gly Arg Ala Trp Phe
1               5

<210> SEQ ID NO 190
<211> LENGTH: 357
<212> TYPE: DNA
<213> ORGANISM: Homo sapiens

<400> SEQUENCE: 190
caggttcagc tggttcagtc tggcgccgaa gtgaagaaac tggcgcctc cgtgaagatg      60 agctgcaagg ctagcgtgta caccttcacc ggctacaaca tgcattggat ccagcagagc     120
cctggacagg gcctcgaatg gattggagga ctgcaccctg caacggcga cagctcttac     180 aaccagaagt tcaagggcag agccacactg accgccgaca gtctagcaa caccgcctac     240 atggaactga gcagcctgag aagcgaggac accgccgtgt actactgtgc cttacaaca     300 gccggcagag cctggtttcc ttactgggga cagggaaccc tggtcaccgt tagctct      357

<210> SEQ ID NO 191
<211> LENGTH: 119
<212> TYPE: PRT
<213> ORGANISM: Homo sapiens

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Asn Ile Phe Thr Gly Tyr
                20                  25                  30

Asn Met His Trp Val Arg Gln Ala Pro Gly Gln Gly Leu Glu Trp Met
            35                  40                  45

Gly Gly Leu His Pro Gly Asn Gly Asp Thr Ser Tyr Asn Gln Lys Phe
        50                  55                  60

Gln Gly Arg Val Thr Leu Thr Ala Asp Arg Ser Ser Asn Thr Ala Tyr
65                  70                  75                  80

```
Met Glu Leu Ser Ser Leu Arg Ser Glu Asp Thr Ala Val Tyr Tyr Cys
                85                  90                  95

Ala Leu Thr Thr Ala Gly Arg Ala Trp Phe Ala Tyr Trp Gly Gln Gly
            100                 105                 110

Thr Leu Val Thr Val Ser Ser
        115

<210> SEQ ID NO 192
<211> LENGTH: 5
<212> TYPE: PRT
<213> ORGANISM: Homo sapiens

<400> SEQUENCE: 192

Gly Tyr Asn Met His
1               5

<210> SEQ ID NO 193
<211> LENGTH: 17
<212> TYPE: PRT
<213> ORGANISM: Homo sapiens

<400> SEQUENCE: 193

Gly Leu His Pro Gly Asn Gly Asp Thr Ser Tyr Asn Gln Lys Phe Gln
1               5                   10                  15

Gly

<210> SEQ ID NO 194
<211> LENGTH: 8
<212> TYPE: PRT
<213> ORGANISM: Homo sapiens

<400> SEQUENCE: 194

Thr Thr Ala Gly Arg Ala Trp Phe
1               5

<210> SEQ ID NO 195
<211> LENGTH: 357
<212> TYPE: DNA
<213> ORGANISM: Homo sapiens

<400> SEQUENCE: 195
caggttcagc tggttcagtc tggcgccgaa gtgaagaaac ctggcgcctc tgtgaaggtg      60
tcctgcaagg ctagcggcaa catcttcacc ggctacaaca tgcactgggt ccgacaggct     120
ccaggacagg gacttgaatg gatgggagga ctgcaccctg gcaacggcga cacaagctac     180
aaccagaaat tccagggcag agtgaccctg accgccgaca gatctagcaa caccgcctac     240
atggaactga gcagcctgag aagcgaggac accgccgtgt actactgtgc cttacaaca      300 gccggcagag cttggttttgc ttactggggc cagggaaccc tggtcaccgt tcttct        357

<210> SEQ ID NO 196
<211> LENGTH: 119
<212> TYPE: PRT
<213> ORGANISM: Homo sapiens

<400> SEQUENCE: 196

Gln Val Gln Leu Val Gln Ser Gly Ala Glu Val Lys Lys Pro Gly Ala
1               5                   10                  15

Ser Val Lys Met Ser Cys Lys Ala Ser Val Tyr Thr Phe Thr Gly Tyr
            20                  25                  30
```

Asn Met His Trp Val Arg Gln Ala Pro Gly Gln Gly Leu Glu Trp Ile
            35                  40                  45

Gly Gly Leu His Pro Gly Asn Gly Asp Thr Ser Tyr Asn Gln Lys Phe
     50                  55                  60

Lys Asp Arg Ala Thr Leu Thr Ala Asp Arg Ser Ser Asn Thr Ala Tyr
 65                  70                  75                  80

Met Glu Leu Ser Ser Leu Arg Ser Glu Asp Thr Ala Val Tyr Tyr Cys
                 85                  90                  95

Ala Leu Thr Thr Ala Gly Arg Ala Trp Phe Ala Tyr Trp Gly Gln Gly
            100                 105                 110

Thr Leu Val Thr Val Ser Ser
        115

<210> SEQ ID NO 197
<211> LENGTH: 5
<212> TYPE: PRT
<213> ORGANISM: Homo sapiens

<400> SEQUENCE: 197

Gly Tyr Asn Met His
1               5

<210> SEQ ID NO 198
<211> LENGTH: 17
<212> TYPE: PRT
<213> ORGANISM: Homo sapiens

<400> SEQUENCE: 198

Gly Leu His Pro Gly Asn Gly Asp Thr Ser Tyr Asn Gln Lys Phe Lys
1               5                   10                  15

Asp

<210> SEQ ID NO 199
<211> LENGTH: 8
<212> TYPE: PRT
<213> ORGANISM: Homo sapiens

<400> SEQUENCE: 199

Thr Thr Ala Gly Arg Ala Trp Phe
1               5

<210> SEQ ID NO 200
<211> LENGTH: 357
<212> TYPE: DNA
<213> ORGANISM: Homo sapiens

<400> SEQUENCE: 200
caggttcagc tggttcagtc tggcgccgaa gtgaagaaac tggcgcctc cgtgaagatg      60 agctgcaagg ctagcgtgta caccttcacc ggctacaaca tgcactgggt ccgacaggct    120
ccaggacagg gacttgaatg gatcggagga ctgcaccctg gcaacggcga cacaagctac    180
aaccagaagt tcaaggacag agccacactg accgccgaca agcagcaa caccgcctac     240 atggaactga gcagcctgag aagcgaggac accgccgtgt actactgtgc ccttacaaca    300
gccggcagag cttggtttgc ttactggggc cagggaaccc tggtcaccgt ttcttct       357

<210> SEQ ID NO 201
<211> LENGTH: 119
<212> TYPE: PRT
<213> ORGANISM: Homo sapiens

<400> SEQUENCE: 201

Glu Val Gln Leu Val Gln Ser Gly Ala Glu Val Lys Lys Pro Gly Ala
1               5                  10                  15

Thr Val Lys Ile Ser Cys Lys Ala Ser Gly Asn Ile Phe Thr Ser Tyr
            20                  25                  30

Asn Met His Val Arg Gln Ala Pro Gly Gln Gly Leu Glu Trp Met
        35                  40                  45

Gly Gly Leu His Pro Gly Asn Gly Asp Thr Ser Tyr Asn Gln Lys Phe
    50                  55                  60

Gln Gly Arg Val Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Val Leu Thr Thr Ala Gly Arg Ala Trp Phe Ala Tyr Trp Gly Gln Gly
            100                 105                 110

Thr Leu Val Thr Val Ser Ser
        115

<210> SEQ ID NO 202
<211> LENGTH: 5
<212> TYPE: PRT
<213> ORGANISM: Homo sapiens

<400> SEQUENCE: 202

Ser Tyr Asn Met His
1               5

<210> SEQ ID NO 203
<211> LENGTH: 17
<212> TYPE: PRT
<213> ORGANISM: Homo sapiens

<400> SEQUENCE: 203

Gly Leu His Pro Gly Asn Gly Asp Thr Ser Tyr Asn Gln Lys Phe Gln
1               5                   10                  15

Gly

<210> SEQ ID NO 204
<211> LENGTH: 8
<212> TYPE: PRT
<213> ORGANISM: Homo sapiens

<400> SEQUENCE: 204

Thr Thr Ala Gly Arg Ala Trp Phe
1               5

<210> SEQ ID NO 205
<211> LENGTH: 357
<212> TYPE: DNA
<213> ORGANISM: Homo sapiens

<400> SEQUENCE: 205
gaagtgcagc tggttcagtc tggcgccgaa gtgaagaaac ctggcgccac cgtgaagatc     60
agctgcaagg ctagcggcaa catcttcacc agctacaaca tgcactgggt ccgacaggcc    120
cctggacagg gacttgaatg gatgggagga ctgcaccctg gcaacggcga cacaagctac    180
aaccagaaat tccagggcag agtgaccctg accgccgaca gtctagcag caccgcctac    240 atggaactga gcagcctgag aagcgaggac accgccgtgt actactgtgt gctgacaaca    300

```
gccggcagag cttggtttgc ttactggggc cagggaaccc tggtcaccgt ttcttct      357
```

<210> SEQ ID NO 206
<211> LENGTH: 119
<212> TYPE: PRT
<213> ORGANISM: Homo sapiens

<400> SEQUENCE: 206

```
Glu Val Gln Leu Val Gln Ser Gly Ala Glu Val Lys Lys Pro Gly Ala
1               5                   10                  15

Thr Val Lys Met Ser Cys Lys Ala Ser Val Tyr Thr Phe Thr Ser Tyr
            20                  25                  30

Asn Met His Trp Val Arg Gln Ala Pro Gly Gln Gly Leu Glu Trp Ile
        35                  40                  45

Gly Gly Leu His Pro Gly Asn Gly Asp Thr Ser Tyr Asn Gln Asn Phe
    50                  55                  60

Lys Gly Arg Ala Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Val Leu Thr Thr Ala Gly Arg Ala Trp Phe Ala Tyr Trp Gly Gln Gly
            100                 105                 110

Thr Leu Val Thr Val Ser Ser
        115
```

<210> SEQ ID NO 207
<211> LENGTH: 5
<212> TYPE: PRT
<213> ORGANISM: Homo sapiens

<400> SEQUENCE: 207

```
Ser Tyr Asn Met His
1               5
```

<210> SEQ ID NO 208
<211> LENGTH: 17
<212> TYPE: PRT
<213> ORGANISM: Homo sapiens

<400> SEQUENCE: 208

```
Gly Leu His Pro Gly Asn Gly Asp Thr Ser Tyr Asn Gln Asn Phe Lys
1               5                   10                  15

Gly
```

<210> SEQ ID NO 209
<211> LENGTH: 8
<212> TYPE: PRT
<213> ORGANISM: Homo sapiens

<400> SEQUENCE: 209

```
Thr Thr Ala Gly Arg Ala Trp Phe
1               5
```

<210> SEQ ID NO 210
<211> LENGTH: 357
<212> TYPE: DNA
<213> ORGANISM: Homo sapiens

<400> SEQUENCE: 210

```
gaagtgcagc tggttcagtc tggcgccgaa gtgaagaaac ctggcgccac cgtgaagatg      60
```

| | |
|---|---|
| agctgcaagg ctagcgtgta caccttcacc agctacaaca tgcactgggt ccgacaggcc | 120 |
| cctggacagg gacttgaatg gatcggagga ctgcaccctg gcaacggcga cacaagctac | 180 |
| aaccagaact tcaagggcag agccacactg accgccgaca gtctagcag caccgcctac | 240 |
| atggaactga gcagcctgag aagcgaggac accgccgtgt actactgtgt gctgacaaca | 300 |
| gccggcagag cttggttttgc ttactggggc cagggaaccc tggtcaccgt ttcttct | 357 |

<210> SEQ ID NO 211
<211> LENGTH: 107
<212> TYPE: PRT
<213> ORGANISM: Homo sapiens

<400> SEQUENCE: 211

Asp Ile Gln Met Thr Gln Ser Pro Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Thr Phe Thr Ile Ser Ser Leu Gln Pro
65                  70                  75                  80
Glu Asp Ile Ala Thr Tyr Phe Cys Gln Gln Gly Asn Thr Leu Pro Trp
                85                  90                  95
Thr Phe Gly Gly Gly Thr Lys Val Glu Ile Lys
            100                 105

<210> SEQ ID NO 212
<211> LENGTH: 11
<212> TYPE: PRT
<213> ORGANISM: Homo sapiens

<400> SEQUENCE: 212

Gln Ala Ser Gln Asp Ile Ser Asn Tyr Leu Asn
1               5                   10

<210> SEQ ID NO 213
<211> LENGTH: 7
<212> TYPE: PRT
<213> ORGANISM: Homo sapiens

<400> SEQUENCE: 213

Tyr Thr Ser Arg Leu His Ser
1               5

<210> SEQ ID NO 214
<211> LENGTH: 9
<212> TYPE: PRT
<213> ORGANISM: Homo sapiens

<400> SEQUENCE: 214

Gln Gln Gly Asn Thr Leu Pro Trp Thr
1               5

<210> SEQ ID NO 215
<211> LENGTH: 321
<212> TYPE: DNA
<213> ORGANISM: Homo sapiens

<400> SEQUENCE: 215

```
gacatccaga tgacacagag ccctagcagc ctgtctgcca gcgtgggaga cagagtgacc      60
atcacctgtc aggccagcca ggacatcagc aactacctga actggtatca gcagaagccc     120
ggcaaggccc ctaagctgct gatctactac accagcagac tgcacagcgg cgtgccctct     180
agattttctg gcagcggctc tggcaccgac tacaccttca caatcagcag cctgcagcct     240
gaggatatcg ctacctactt ctgccagcaa ggcaacaccc tgccttggac atttggcgga     300
ggcaccaagg tggaaatcaa g                                               321
```

<210> SEQ ID NO 216
<211> LENGTH: 107
<212> TYPE: PRT
<213> ORGANISM: Homo sapiens

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys
            100                 105

<210> SEQ ID NO 217
<211> LENGTH: 11
<212> TYPE: PRT
<213> ORGANISM: Homo sapiens

<400> SEQUENCE: 217

Arg Ala Ser Gln Asp Ile Ser Asn Tyr Leu Asn
1               5                   10

<210> SEQ ID NO 218
<211> LENGTH: 7
<212> TYPE: PRT
<213> ORGANISM: Homo sapiens

<400> SEQUENCE: 218

Tyr Thr Ser Arg Leu His Ser
1               5

<210> SEQ ID NO 219
<211> LENGTH: 9
<212> TYPE: PRT
<213> ORGANISM: Homo sapiens

<400> SEQUENCE: 219

Gln Gln Gly Asn Thr Leu Pro Trp Thr
1               5

<210> SEQ ID NO 220
<211> LENGTH: 321
<212> TYPE: DNA

<213> ORGANISM: Homo sapiens

<400> SEQUENCE: 220

```
gacatccaga tgacacagag ccctagcagc ctgtctgcca gcgtgggaga cagagtgacc    60
atcacctgtc gggccagcca ggacatcagc aactacctga actggtatca gcagaagccc   120
ggcaaggccc ctaagctgct gatctactac accagcagac tgcacagcgg cgtgccctct   180
agatttctg gcagcggctc tggcaccgac tacaccctga caatctctag cctgcagcct   240
gaggacttcg ctacctactt ctgccagcaa ggcaacaccc tgccttggac atttggcgga   300
ggcaccaagg tggaaatcaa g                                              321
```

<210> SEQ ID NO 221
<211> LENGTH: 107
<212> TYPE: PRT
<213> ORGANISM: Homo sapiens

<400> SEQUENCE: 221

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Phe Cys Gln Gln Gly Asn Thr Leu Pro Leu
                85                  90                  95
Thr Phe Gly Gly Gly Thr Lys Val Glu Ile Lys
            100                 105

<210> SEQ ID NO 222
<211> LENGTH: 11
<212> TYPE: PRT
<213> ORGANISM: Homo sapiens

<400> SEQUENCE: 222

Gln Ala Ser Gln Asp Ile Ser Asn Tyr Leu Asn
1               5                   10

<210> SEQ ID NO 223
<211> LENGTH: 7
<212> TYPE: PRT
<213> ORGANISM: Homo sapiens

<400> SEQUENCE: 223

Tyr Thr Ser Arg Leu His Ser
1               5

<210> SEQ ID NO 224
<211> LENGTH: 9
<212> TYPE: PRT
<213> ORGANISM: Homo sapiens

<400> SEQUENCE: 224

Gln Gln Gly Asn Thr Leu Pro Leu Thr
1               5

```
<210> SEQ ID NO 225
<211> LENGTH: 321
<212> TYPE: DNA
<213> ORGANISM: Homo sapiens

<400> SEQUENCE: 225
gacatccaga tgacacagag ccctagcagc ctgtctgcca gcgtgggaga cagagtgacc      60
atcacctgtc aggccagcca ggacatcagc aactacctga actggtatca gcagaagccc     120
ggcaaggccc ctaagctgct gatctactac accagcagac tgcacagcgg cgtgccctct     180
agattttctg gcagcggctc tggcaccgac tacaccctga caatctctag cctgcagcct     240
gaggacttcg ctacctactt ctgccagcaa ggcaacaccc tgcctctgac atttggcgga     300
ggcaccaagg tggaaatcaa g                                               321

<210> SEQ ID NO 226
<211> LENGTH: 108
<212> TYPE: PRT
<213> ORGANISM: Homo sapiens

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Pro
                85                  90                  95

Trp Thr Phe Gly Gly Gly Thr Lys Val Glu Ile Lys
            100                 105

<210> SEQ ID NO 227
<211> LENGTH: 11
<212> TYPE: PRT
<213> ORGANISM: Homo sapiens

<400> SEQUENCE: 227

Gln Ala Ser Gln Asp Ile Ser Asn Tyr Leu Asn
1               5                   10

<210> SEQ ID NO 228
<211> LENGTH: 7
<212> TYPE: PRT
<213> ORGANISM: Homo sapiens

<400> SEQUENCE: 228

Tyr Thr Ser Arg Leu His Ser
1               5

<210> SEQ ID NO 229
<211> LENGTH: 10
<212> TYPE: PRT
<213> ORGANISM: Homo sapiens

<400> SEQUENCE: 229

Gln Gln Gly Asn Thr Leu Pro Pro Trp Thr
```

```
<210> SEQ ID NO 230
<211> LENGTH: 324
<212> TYPE: DNA
<213> ORGANISM: Homo sapiens

<400> SEQUENCE: 230
gacatccaga tgacacagag ccctagcagc ctgtctgcca gcgtgggaga cagagtgacc      60
atcacctgtc aggccagcca ggacatcagc aactacctga actggtatca gcagaagccc     120
ggcaaggccc ctaagctgct gatctactac accagcagac tgcacagcgg cgtgccctct     180
agattttctg gcagcggctc tggcaccgac tacaccctga caatctctag cctgcagcct     240
gaggacttcg ctacctactt ctgccagcaa ggcaacaccc tgcctccatg gacatttggc     300
ggaggcacca agtggaaat caag                                             324

<210> SEQ ID NO 231
<211> LENGTH: 33
<212> TYPE: DNA
<213> ORGANISM: Artificial Sequence
<220> FEATURE:
<223> OTHER INFORMATION: synthetic nucleic acid

<400> SEQUENCE: 231
ctgagaggtg ccagatgtat gaaggtgctg cag                                   33

<210> SEQ ID NO 232
<211> LENGTH: 33
<212> TYPE: DNA
<213> ORGANISM: Artificial Sequence
<220> FEATURE:
<223> OTHER INFORMATION: synthetic nucleic acid

<400> SEQUENCE: 232
tccgcctccg ccgctagcgt gctgctcgaa ggg                                   33
```

AUTOIMMUNE SUPPRESSOR AND APPLICATION THEREOF

CROSS-REFERENCE TO RELATED APPLICATIONS

This application is a U.S. national phase application of International Application No. PCT/CN2019/089031, filed on May 29, 2019, which claims the benefits of Chinese patent application No. 201810528489.8, filed on May 29, 2018, the disclosures of which are hereby incorporated by reference in their entireties.

FIELD OF THE INVENTION

The present disclosure relates to a dual inhibiting antibody that targets interleukin-4 and interleukin-13, a manufacturing method therefor and use thereof.

BACKGROUND OF THE INVENTION

Interleukin-4 (IL-4) is a key driving factor for Th2 helper cell-mediated immune responses. Eosinophilic granulocytes, basophilic granulocytes, mast cells, or innate lymphoid cells secrete IL-4 after being activated by immunogens, IL-4 can induce antigen-activated naïve T cells to differentiate into Th2 cells. Th2 cells express cytokines such as IL-4, IL-5 and IL-13, and IL-4 acts on Th2 cells themselves, which can form a loop amplifying and activating effect.

IL-4 and IL-13 exert biological activities by binding to specific receptors on the cell surface and transmitting signals to the interior of the cell. By acting on B cells, IL-4 and IL-13 can up-regulate the expression of MHC class II antigens and enhances the ability of B cells to present antigens, which makes the immune system produce an immune response to stimulation of small amounts of antigens, and induces a B-cell antibody class switching, producing IgG1 and IgE. The binding of IL-4 and IgE to mast cells results in an activation of the mast cells to release histamines, serotonins, etc. Eosinophilic granulocytes can be recruited and activated by IL-4, IL-5 and IL-13 secreted by Th2 cells. IL-13 acts on epithelial cells and smooth muscle cells, leading to airway epithelial goblet cell proliferation and smooth muscle contraction.

IL-4Rα (Uniprot P24394), a type-I transmembrane protein with a molecular weight of approximately 140 KDa, is a co-receptor for IL-4 and IL-13. IL-4 binds to IL-4Rα with a high affinity and forms a complex with γc on the cell surface, which complex transmits a signal via γc, and is referred to as a type-I receptor complex IL-4Rα/IL-4Rγc; in contrast to IL-4, IL-13 binds to IL-13Rα1 with a low affinity, and then binds to IL-4Rα to form a high-affinity receptor, which transmits a signal via IL-13Rα1, and is referred to as a type-II receptor complex IL-4Rα/IL-13Rα1. IL-4 can function through type-I receptors and type-II receptors, whereas IL-13 can only function through type-II receptors. Differences in the expression on effector cells between type-I receptors and type-II receptors result in IL-4 and IL-13 producing partial overlapping biological effects and their respective specific functions.

Interleukin (IL)-13 is considered to be a key mediator of helper T cell type 2 (Th2) inflammation, and the elevated level of IL-13 is associated with a variety of diseases including, but not limited to, asthma, inflammatory bowel disease, idiopathic pulmonary fibrosis (IPF), chronic obstructive pulmonary disease (COPD) and atopic dermatitis and others (Oh C K et al., Eur Respir Rev 19:46-54 (2010); Fahy J V et al., Nat Rev Immunol 15:57-65[2015]). IL-13 is produced by a number of cell types including Th2 cells, basophilic granulocytes, eosinophilic granulocytes, mast cells, airway epithelial cells and type 2 innate lymphoid cells. IL-13 binds to a heterodimeric receptor IL-4Rα/IL-13Rα1, which is also a receptor for IL-4, and activates the STAT-6 signaling pathway (Hershey G K, J Allergy Clin Immunol 111(4):677-90[2003]). In some cases, IL-13 is associated with clinical manifestations of asthma, including mucus production, subepidermal fibrosis, IgE production, smooth muscle hyperplasia, and recruitment and activation of inflammatory cells (Hershey G K, J Allergy Clin Immunol 111(4):677-90[2003]; Fahy J V et al., Nat Rev Immunol 15:57-65[2015]). Since Th2 inflammation involves the activity of several cell types other than Th2 cells, including type 2 innate lymphoid cells (ILC2s), "Th2 inflammation" has recently been referred to as "type 2 inflammation" in the scientific literature. In addition to Th2 cells, ILC2s have also been identified as an important source of cytokines such as IL-5 and IL-13. Therefore, cytokines such as IL-13 and IL-5, which have previously been identified as Th2 cytokines, are now also referred to as type 2 cytokines in the scientific literature. Similarly, disease states associated with such cytokines are now also referred to as type 2-driven diseases or type 2-related diseases. See, for example, Noonan et al., J. Allergy Clin Immunol., 132(3):567-574(2013); Hanania et al., Thorax 70(8):748-56(2015); and Cai et al., Bioanalysis 8(4):323-332(2016). For example, the term "type 2 asthma" used in the scientific literature reflects the evolutionary process of understanding of asthma, and is characterized by high levels of interleukins (including IL-5 and IL-13) in lung tissue. Therefore, "Th2" and "type 2" are used interchangeably herein.

Asthma is a chronic airway inflammatory disease. Patients with asthma have airway hyperresponsiveness and varying degrees of reversible airway obstruction, and long-term recurrent attacks cause airway remodeling (involving collagen fibers and smooth muscles), resulting in airway thickening and stenosis, and leading to obstructive emphysema. About 50% of patients with severe asthma have a Th2 cell-mediated type-II inflammatory response. Compared with the normal person, asthma patients have elevated levels of IL-4 and IL-13 in both serum or bronchial biopsies. After the stimulation with allergens, the levels of IL-4 and IL-13 are both found to increase in bronchoalveolar lavage fluid in patients with asthma. Inhalation of IL-4 in patients with allergic asthma can induce characteristic symptoms of asthma, such as airway hyperresponsiveness and increased eosinophilic granulocytes in sputum. Researches show that the onset of allergic asthma is closely related to the ratio imbalance of Th1/Th2 type cells, thus producing excessive cytokine IL-4. IL-4 is the only cytokine that determines the differentiation of Th1 into Th2 cells, and promotes the synthesis of IgE by B cells, whereas IL-13 is the dominant partner that triggers respiratory tract hyperresponsiveness, airway remodeling, and excessive mucus secretion (Annu Rev Immunol, Wynn et al. 2003).

Eosinophilic granulocytes are present in peripheral blood of patients with atopic dermatitis, and molecules associated with Th2 pathway activation are detected in non-lesional skin of patients with atopic dermatitis but not in normal skin of healthy controls. In addition, the level of thymus and activation-regulated chemokine CCL17 is elevated in serum of patients with atopic dermatitis, and CCL17 is an IL-4 and IL-13-induced chemokine that selectively induces T cell activation. Broad-spectrum therapies, such as topical corticosteroids and oral cyclosporin A, can induce a rapid decline in TARC levels, which is closely related to the severity of atopic dermatitis, demonstrating that a potential type-II inflammatory drives the atopic dermatitis in the disease. Atopic dermatitis is generally complicated with other allergic diseases such as allergic rhinitis and asthma.

The pathogenesis of atopic rhinitis is believed to be a Th2-mediated allergy to common allergens such as pollen, mold and house dust mites. Compared with the control group, younger groups with seasonal atopic rhinitis have an elevated level of IL-4 in the nasal lavage. Levels of IL-4 and IL-13 are up-regulated in nasal mast cells in patients with perennial atopic rhinitis compared with nasal mast cells in patients with chronic infectious rhinitis. IL-4 induces up-regulation of FcεRI mRNA and expression of cell surface protein in nasal mast cells. Atopic rhinitis can develop into chronic sinusitis accompanied with nasal polyps, and the nasal polyps also have a Th2-type response, which leads to elevated levels of eosinophilic granulocytes, IL-5, IgE, and tissue eosinophilic granulocyte chemokines. The mucosa of patients having chronic sinusitis with nasal polyps contains more innate lymphoid ILC2 cells than that of patients having chronic sinusitis without nasal polyps or having normal mucosa, wherein the innate lymphoid ILC2 cells secrete high levels of IL-13 under the stimulation of IL-33.

Chronic obstructive pulmonary disease is an obstructive pulmonary disease characterized by significant lung and systemic inflammation. In the patients, the inflammation in most of the airways of patients leads to chronic bronchitis and the inflammation in small airways, which results in reduced lumen and increased airflow resistance. In contrast to asthma, airflow limitation in chronic obstructive pulmonary disease is irreversible. Researches have shown that lymphocytes obtained from bronchoalveolar lavage in patients with chronic obstructive pulmonary disease have a mixed phenotype. Compared with patients with non-chronic obstructive pulmonary or controls, patients with chronic obstructive pulmonary disease have a higher proportion of IL-4$^+$CD4, IL-4$^+$CD8 and IL-13$^+$CD8 T cells. 30% of patients with acute exacerbation of chronic obstructive pulmonary disease have respiratory viruses, 77% of which are rhinoviruse, and rhinoviruse is an important reason causing the worsening of chronic obstructive pulmonary disease. Patients experiencing the worsening of chronic obstructive pulmonary disease have both Th1 and Th2 responses in the lungs and peripheral blood; IFNγ is not expressed ubiquitously in these patients, which has no significant difference compared with the patients in stable phase and the control group; on the contrary, IL-4 is expressed ubiquitously in these patients, which is up-regulated compared with the patients in stable phase and the control group. Researches have shown that controlling the levels of eosinophilic granulocytes may bring a very significant clinical benefit for patients with chronic obstructive pulmonary disease, reducing the worsening by 62%. The use of beralizumab in patients with eosinophilic granulocytes>200 per microliter can effectively remove the eosinophilic granulocytes in the patients, reduce symptoms of acute exacerbation of chronic obstructive pulmonary disease, and improve FEV1 and symptom scores (Brightling C E et al., Lancet Respir Med. 2014). Asthma/chronic obstructive pulmonary disease overlap syndrome is now recognized as a disease with two key aspects, asthma and chronic obstructive pulmonary disease.

In view of the effect and function of IL-4Rα and IL-13 in various related diseases, there remains a need in the art to develop improved anti-IL-4Rα specific antibodies suitable for treating patients.

SUMMARY OF THE INVENTION

Through extensive, in-depth research, and mass screening, the inventors have unexpectedly obtained an anti-IL-4Rα antibody having extremely excellent affinity and specificity, and a humanized antibody obtained based on the anti-IL-4Rα antibody. The antibody of the present invention is capable of binding IL-4Rα antigens with a high specificity and a high affinity, and significantly inhibits the binding of IL-4Rα to IL-4 and IL-4Rα to IL-13. Furthermore, the antibody of the present invention has no visible side effects on mammals. The present invention has been accomplished on the basis of the above.

In one aspect, the disclosure relates to an antibody or a functional fragment thereof that specifically binds to IL-4Rα.

An antibody or a functional fragment thereof according to the preceding aspect, comprising a heavy chain CDR selected from the amino acid sequences of SEQ ID NOs: 2-4, 12-14, 22-24, 32-34, 42-44, 52-54, 62-64, 72-74, 82-84, 92-94, 102-104, 112-114, 122-124, 132-134, 142-144, 152-154, 162-164, 172-174, 177-179, 182-184, 187-189, 192-194, 197-199, 202-204 and 207-209 or any variant thereof, and/or a light chain CDR selected from the amino acid sequences of SEQ ID NOs: 7-9, 17-19, 27-29, 37-39, 47-49, 57-59, 67-69, 77-79, 87-89, 97-99, 107-109, 117-119, 127-129, 137-139, 147-149, 157-159, 167-169, 212-214, 217-219, 222-224, 227-229 or any variant thereof.

The antibody or functional fragment thereof of any of the preceding aspects, comprising a heavy chain CDR1 selected from amino acid sequences SEQ ID NOs: 2, 12, 22, 32, 42, 52, 62, 72, 82, 92, 102, 112, 122, 132, 142, 152, 162, 172, 177, 182, 187, 192, 197, 202, 207 or any variant thereof, a heavy chain CDR2 selected from amino acid sequences SEQ ID NOs: 3, 13, 23, 33, 43, 53, 63, 73, 83, 93, 103, 113, 123, 133, 143, 153, 163, 173, 178, 183, 188, 193, 198, 203, 208 or any variant thereof, and a heavy chain CDR3 selected from amino acid sequences SEQ ID NOs: 4, 14, 24, 34, 44, 54, 64, 74, 84, 94, 104, 114, 124, 134, 144, 154, 164, 174, 179, 184, 189, 194, 199, 204, 209 or any variant thereof; and/or a light chain CDR1 selected from amino acid sequences SEQ ID NOs: 7, 17, 27, 37, 47, 57, 67, 77, 87, 97, 107, 117, 127, 137, 147, 157, 167, 212, 217, 222, 227 or any variant thereof, a light chain CDR2 selected from amino acid sequences SEQ ID NOs: 8, 18, 28, 38, 48, 58, 68, 78, 88, 98, 108, 118, 128, 138, 148, 158, 168, 213, 218, 223, 228 or any variant thereof, and a light chain CDR3 selected from amino acid sequences SEQ ID NOs: 9, 19, 29, 39, 49, 59, 69, 79, 89, 99, 109, 119, 129, 139, 149, 159, 169, 214, 219, 224, 229 or any variant thereof.

The antibody or functional fragment thereof of any of the preceding aspects, comprising a heavy chain variable region selected from amino acid sequences SEQ ID NOs: 1, 11, 21, 31, 41, 51, 61, 71, 81, 91, 101, 111, 121, 131, 141, 151, 161, 171, 176, 181, 186, 191, 196, 201, 206 or any variant thereof, and/or alight chain variable region selected from amino acid sequences SEQ ID NOs: 6, 16, 26, 36, 46, 56, 66, 76, 86, 96, 106, 116, 126, 136, 146, 156, 166, 211, 216, 221, 226 or any variant thereof.

The antibody or functional fragment thereof of any of the preceding aspects, comprising a heavy chain variable region selected form amino acid sequence SEQ ID NO: 171 or any variant thereof, and/or a light chain variable region selected from amino acid sequence SEQ ID NO: 221 or any variant thereof.

The antibody or functional fragment thereof of any of the preceding aspects, comprising a heavy chain variable region selected form amino acid sequence SEQ ID NO: 176 or any variant thereof, and/or a light chain variable region selected from amino acid sequence SEQ ID NO: 221 or any variant thereof.

The antibody or functional fragment thereof of any of the preceding aspects, comprising a heavy chain variable region selected form amino acid sequence SEQ ID NO: 196 or any variant thereof, and/or a light chain variable region selected from amino acid sequence SEQ ID NO: 211 or any variant thereof.

The antibody or functional fragment thereof of any of the preceding aspects, comprising a heavy chain variable region selected form amino acid sequence SEQ ID NO: 196 or any variant thereof, and/or a light chain variable region selected from amino acid sequence SEQ ID NO: 216 or any variant thereof.

The antibody or functional fragment thereof of any of the preceding aspects, wherein the antibody is an antibody fragment.

The antibody or functional fragment thereof of any of the preceding aspects, wherein the antibody or functional fragment thereof inhibits the interaction of hIL-4 with hIL-4Rα; preferably, the antibody or functional fragment thereof also inhibits the binding of hIL-4Rα to a complex hIL-13Rα/hIL-13.

The antibody or functional fragment thereof of any of the preceding aspects, wherein the antibody or functional fragment thereof is humanized.

The antibody or functional fragment thereof, having at least 60%, 65%, 70%, 75%, 80%, 85%, 90%, 95%, 96%, 97%, 98%, 99% or more sequence identity to the antibody or functional fragment thereof of any of the preceding aspects.

A nucleic acid molecule encoding the antibody or functional fragment thereof of any of the preceding aspects, or a nucleic acid molecule having at least 60%, 65%, 70%, 75%, 80%, 85%, 90%, 95%, 96%, 97%, 98%, 99% or more sequence identity thereto.

A vector comprising the nucleic acid of any of the preceding aspects.

A cell comprising the vector of any of the preceding aspects.

A pharmaceutical composition comprising the antibody or functional fragment thereof, or the nucleic acid encoding same of any of the preceding aspects, and a pharmaceutically acceptable carrier.

A method for treating allergic diseases in a mammal, comprising the step of administering to the mammal a therapeutically effective amount of the antibody or functional fragment thereof, or the nucleic acid molecule, or the vector, or the cell or the pharmaceutical composition of any of the preceding aspects.

A method for treating cancers, comprising the step of administering to the mammal a therapeutically effective amount of the antibody or functional fragment thereof, or the nucleic acid molecule, or the vector, or the cell or the pharmaceutical composition of any of the preceding aspects.

A method for treating asthma in a mammal, comprising the step of administering to the mammal a therapeutically effective amount of the antibody or functional fragment thereof, or the nucleic acid molecule, or the vector, or the cell or the pharmaceutical composition of any of the preceding aspects.

A method for treating chronic obstructive pulmonary disease in a mammal, comprising the step of administering to the mammal a therapeutically effective amount of the antibody or functional fragment thereof, or the nucleic acid molecule, or the vector, or the cell or the pharmaceutical composition of any of the preceding aspects.

A method for treating diseases associated with abnormal production of IL-4 and/or IL-13 in a mammal, comprising the step of administering to the mammal a therapeutically effective amount of the antibody or functional fragment thereof, or the nucleic acid molecule, or the vector, or the cell or the pharmaceutical composition of any of the preceding aspects.

A method for inhibiting a TH-2 mediated response in a mammal, comprising the step of administering to the mammal a therapeutically effective amount of the antibody or functional fragment thereof, or the nucleic acid molecule, or the vector, or the cell or the pharmaceutical composition of any of the preceding aspects.

Use of the antibody or functional fragment thereof, or the nucleic acid molecule, or the vector, or the cell or the pharmaceutical composition of any of the preceding aspects in the preparation of a drug for the treatment of allergic diseases in a mammal.

Use of the antibody or functional fragment thereof, or the nucleic acid molecule, or the vector, or the cell or the pharmaceutical composition of any of the preceding aspects in the preparation of a drug for the treatment of asthma in a mammal.

Use of the antibody or functional fragment thereof, or the nucleic acid molecule, or the vector, or the cell or the pharmaceutical composition of any of the preceding aspects in the preparation of a drug for the treatment of chronic obstructive pulmonary disease in a mammal.

Use of the antibody or functional fragment thereof, or the nucleic acid molecule, or the vector, or the cell or the pharmaceutical composition of any of the preceding aspects in the preparation of a drug for the treatment of diseases associated with abnormal production of IL-4 and/or IL-13.

Use of the antibody or functional fragment thereof, or the nucleic acid molecule, or the vector, or the cell or the pharmaceutical composition of any of the preceding aspects in the preparation of a drug for the treatment of a TH-2 mediated response in a mammal.

DETAILED DESCRIPTION OF THE INVENTION

Figure 1A:
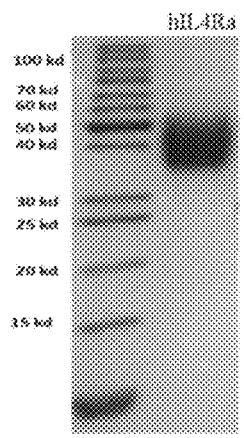
FIG. 1A shows that the protein of the extracellular region of human IL-4Rα has a size of approximately 40K Daltons.

In the present invention, all scientific and technical terms used herein have the meanings commonly understood by a person skilled in the art unless specified otherwise. In addition, terms and laboratory operation steps related to the protein and nucleic acid chemistry, molecular biology, cell and tissue culture, microbiology and immunology as used herein are terms and conventional steps that are widely used in the corresponding art. To better understand the present invention, definitions and explanations of related terms are provided below.

"Interleukin-4" (IL-4) relates to a naturally occurring or endogenous mammalian IL-4 protein or a protein having the same amino acid sequence as the corresponding naturally occurring or endogenous mammalian IL-4 protein (e.g., a recombinant protein and synthetic protein (i.e., a protein prepared by a chemical method of organic synthesis)). Accordingly, as defined herein, the term includes mature IL-4 protein, polymorphic or allelic variants, other isoforms of IL-4, and modified or unmodified forms of the foregoing (e.g., lipidated or glycosylated). The naturally occurring or endogenous IL-4 includes wild-type proteins such as mature IL-4, polymorphic or allelic variants, and other isoforms and mutant forms which occur naturally in mammals (e.g., humans and non-human primates). Such proteins can be recovered or isolated from, for example, a source which naturally produces IL-4. These proteins and proteins having the same amino acid sequence as the corresponding naturally occurring or endogenous IL-4 are referred to by the name of the corresponding mammal. For example, where the corresponding mammal is human, the protein is designated as human IL-4. There are several mutant IL-4 proteins known in the art, as disclosed in WO 03/038041.

"Interleukin-13" (IL-13) relates to a naturally occurring or endogenous mammalian IL-13 protein or a protein having the same amino acid sequence as the corresponding naturally occurring or endogenous mammalian IL-13 protein (e.g., a recombinant protein and synthetic protein (i.e., a protein prepared by a chemical method of organic synthesis)). IL-13 is a cytokine secreted by many cell types, including T helper cell type 2 (Th2) cells. Accordingly, as defined herein, the term includes mature IL-13 protein, polymorphic or allelic variants, other isoforms of IL-13 (e.g., those produced by alternative splicing or other cellular processes), and modified or unmodified forms of the foregoing (e.g., lipidated or glycosylated). The naturally occurring or endogenous IL-13 includes wild-type proteins such as mature IL-13, polymorphic or allelic variants, and other isoforms and mutant forms which occur naturally in mammals (e.g., humans and non-human primates). For example, IL-13 as used herein includes human IL-13 variants in which Arg at position 110 of mature human IL-13 is replaced by Gln (position 110 of mature IL-13 corresponds to position 130 of precursor protein) and Gln is associated with asthma (atopic and nonatopic asthma) and other variants of IL-13. (Heinzmann et al., Hum Mol Genet 9: 549-559(2000)). Such proteins can be recovered or isolated from, for example, a source which naturally produces IL-13. These proteins and proteins having the same amino acid sequence as the corresponding naturally occurring or endogenous IL-13 are referred to by the name of the corresponding mammal. For example, where the corresponding mammal is human, the protein is designated as human IL-13. There are several mutant IL-13 proteins known in the art, as disclosed in WO 03/035847. The amino acid sequence of an exemplary human IL-13 can be found, for example, under UniProtKB Accession No. P35225. IL-13 binds to an IL-13 receptor, wherein the IL-13 receptor may include IL-4 receptor alpha (IL4Rα) complexed with the IL-13 receptor subunit α1 (ILT3RA1) or the IL-13 receptor subunit α2 (IL13RA2). For example, IL-13 can bind to a complex of IL-4 receptor alpha and IL-13 receptor subunit alpha 1.

The phrase "substantially identical" with respect to an antibody chain polypeptide sequence may be construed as an antibody chain exhibiting at least 60%, 65%, 70%, 75%, 80%, 85%, 90%, 95%, 96%, 97%, 98%, 99% or more sequence identity to the reference polypeptide sequence. The term with respect to a nucleic acid sequence may be construed as a sequence of nucleotides exhibiting at least about 60%, 65%, 70%, 75%, 80%, 85%, 90%, 95%, 96%, 97%, 98%, 99% or more sequence identity to the reference nucleic acid sequence.

The terms, "identity" or "homology" may mean the percentage of nucleotide bases or amino acid residues in the candidate sequence that are identical to the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are readily available and well known in the art. Sequence identity may be measured using sequence analysis software.

The phrases and terms "functional fragment, variant, derivative or analog" and the like, as well as various forms thereof, of an antibody or antigen is a compound or molecule having qualitative biological activity in common with a full-length antibody or antigen of interest. For example, a functional fragment or analog of an anti-IL-4 antibody is one which can bind to an IL-4 molecule or one which can prevent or substantially reduce the ability of a ligand or an agonistic or antagonistic antibody, to bind to IL-4.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The multiple substitutions may be at consecutive sites. Also, one amino acid can be substituted with multiple residues, in which case such a variant comprises both a substitution and an insertion. "Insertional" variants are those with one or more amino acids inserted immediately adjacent to an amino acid at a particular position in a native sequence. Immediately adjacent to an amino acid means linked to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

As used herein, the term "antibodies" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. "Antibodies" can also refer to immunoglobulins and immunoglobulin fragments, whether produced naturally or partially or fully synthetically (e.g., recombinantly), including any fragment thereof which comprises at least a partial variable region of an immunoglobulin molecule and retains the binding specificity of the full length of the immunoglobulin molecule. Thus, antibodies include any protein having a binding domain which is homologous or substantially homologous to an immunoglobulin antigen binding domain (an antibody binding site). Antibodies include antibody fragments, such as anti-tumor stem cell antibody fragments. As used herein, the term antibody thus includes synthetic antibodies, recombinantly-produced antibodies, multispecific antibodies (e.g., bispecific antibodies), human antibodies, non-human antibodies, humanized antibodies, chimeric antibodies, intrabodies, and antibody fragments, for example without limitation, Fab fragments, Fab' fragments, F(ab')2 fragments, Fv fragments, disulfide-linked Fv (dsFv), Fd fragments, Fd' fragments, single-chain Fv (scFv), single-chain Fab (scFab), diabodies, anti-idiotypic (anti-Id) antibodies, or antigen-binding fragments of any of the above-mentioned antibodies. The antibodies provided herein include any immunoglobulin class (e.g., IgG, IgM, IgD, IgE, IgA, and IgY), and members of any type (e.g., IgG1, IgG2, IgG3, IgG4, IgA1, and IgA2) or subtype (e.g., IgG2a and IgG2b).

The antibodies of the present invention may be antibodies of any class (e.g., IgG, IgE, IgM, IgD, IgA, etc.), or subclass (e.g., $IgG_1$, $IgG_2$, $IgG_{2a}$, $IgG_3$, $IgG_4$, $IgA_1$, $IgA_2$, etc.) ("type" and "class", as well as "subtype" and "subclass" are used interchangeably herein). Native or wildtype (that is, obtained from a non-artificially manipulated member of a population) antibodies and immunoglobulins are usually heterotetrameric glycoproteins of about 150,000 daltons, which is composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end. By "non-artificially manipulated" is meant not treated to contain or express a foreign antigen binding molecule. Wild type can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-IL-4 antibody" means an antibody or polypeptide derived therefrom (a derivative) which binds specifically to IL-4 as defined herein, including, but not limited to, molecules which inhibit or substantially reduce the binding of IL-4 to its ligands or inhibit IL-4 activity.

The term "variable" in the context of a variable domain of antibodies, refers to certain portions of the pertinent molecules which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) or hypervariable regions, both in the light chain and the heavy chain variable domains. The more highly conserved portions of variable domains are called the framework (FR) regions or sequences. The variable domains of native heavy and light chains each comprise four FR regions, largely adopting a R-sheet configuration, linked by three CDRs, wherein the CDRs form loops connecting, and in some cases forming part of, the R-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, Md. (1987)). As used herein, numbering of immunoglobulin amino acid residues is done using the immunoglobulin amino acid residue numbering system of Kabat et al., unless otherwise indicated. One CDR can carry the ability to bind specifically to the cognate epitope.

The term "hinge" or "hinge region" as used herein refers to a flexible polypeptide comprising amino acids between the first and second constant domains of an antibody.

As used herein, "antibody fragments" or "antigen-binding fragments" of antibodies refer to any portion of a full length antibody that is less than the full length, but comprises at least a portion of the variable region of the antibody that binds to the antigen (e.g., one or more CDRs and/or one or more antibody binding sites), and thus retain binding specificity as well as at least partial specific binding ability of the full length antibody. Thus, antigen-binding fragments refer to antibody fragments comprising an antigen-binding portion that binds to the same antigen as the antibody from which the antibody fragments are derived. Antibody fragments include antibody derivatives produced by enzymatic treatment of full length antibodies, and derivatives produced by the synthesis, such as recombinantly-produced derivatives. Antibodies include antibody fragments. Examples of antibody fragments include, but not limited to, Fab, Fab', F(ab')2, single chain Fv (scFv), Fv, dsFv, diabodies, Fd and Fd' fragments, and other fragments, including modified fragments (see, for example, Methods in Molecular Biology, Vol 207: Recombinant Antibodies for Cancer Therapy Methods and Protocols (2003); Chapter 1; p 3-25, Kipriyanov). The fragments may comprise a plurality of chains joined together, for example via a disulfide bond and/or via a peptide linker. Antibody fragments usually comprise at least or about 50 amino acids, and typically at least or about 200 amino acids. Antigen-binding fragments include any antibody fragments, upon the antibody fragments are inserted into an antibody framework (e.g., by substitution of a corresponding region), an antibody that immunospecifically binds (i.e., exhibiting at least or at least about $10^7$-$10^8$ $M^1$ of Ka) antigens is obtained. "Functional fragments" or "analogs of anti-IL-4 and/or IL-13 antibodies" are fragments or analogs which prevents or substantially reduces the ability of the receptors to bind to ligands or initiate signal transduction. As used herein, functional fragments generally have the same meaning as "antibody fragments" and, in the case of antibodies, may refer to fragments which prevent or substantially reduce the ability of the receptors to bind to ligands or initiate signal transduction, such as $F_v$, $F_{ab}$ and $F_{(ab')2}$. "F" fragments consists of dimers ($V_H$-$V_L$ dimers) formed by a variable domain of a heavy chain and a variable domain of a light chain by non-covalent binding. It is in this configuration that the three CDRs of each variable domain interact to define a target binding site on the surface of the $V_H$-$V_L$ dimer, as is the case with an intact antibody. Collectively, the six CDRs confer antigen-binding specificity to the intact antibody. However, even a single variable domain (or half of an $F_v$ comprising only 3 CDRs specific for a target) has the ability to recognize and bind targets.

"Single-chain F", "sF$_v$" or "scab" antibody fragments comprise $V_H$ and $V_L$ domains of antibodies, wherein these domains are present in a single polypeptide chain. Generally, the $F_v$ polypeptide further comprises a polypeptide linker between the $V_H$ and $V_L$, which is typically a flexible molecule that enables the sFv to form the desired structure for target binding.

The term "diabody" refers to antibody fragments having two antigen-binding sites, the antibody fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain and create two antigen-binding sites.

$F_{ab}$ fragments comprise the variable and constant domains of the light chain as well as the variable and first constant domain ($C_{H1}$) of the heavy chain. $F_{ab'}$ fragments differ from $F_{ab}$ fragments by the addition of a few residues at the carboxyl terminus of the $C_{H1}$ domain to include one or more cysteines from the antibody hinge region. $F_{ab'}$ fragments can be produced by cleavage of the disulfide bond at the hinge cysteines of the pepsin digestion product of F(ab')2. Additional enzymatic and chemical treatments of antibodies can yield other functional fragments of interest.

The term "linear Fab" refers to a tetravalent antibody as described by Miller et al. (Miller et al. (2003), J Immunol. 170: 4854-4861). The "linear Fab" is composed of a tandem of the same CH1-VH domain, paired with the identical light chain at each CH1-VH position. These molecules have been developed in order to increase the valency of an antibody to enhance its functional affinity through the avidity effect, but they are monospecific.

As used herein, the "monoclonal antibody" refers to a population of identical antibodies, i.e., each individual antibody molecule in the population of the monoclonal antibody is identical to other antibody molecules. This property is in contrast to the property of a polyclonal population of antibodies, which comprises antibodies having a plurality of different sequences. Monoclonal antibodies can be prepared by many well-known methods (Smith et al. (2004) J. Clin. Pathol. 57, 912-917; and Nelson et al., J Clin Pathol (2000), 53, 111-117). For example, monoclonal antibodies can be prepared by immortalizing B cells, e.g., by fusion with myeloma cells to produce a hybridoma cell line or by infecting B cells with a virus such as EBV. Recombinant techniques can also be used to prepare antibodies from a clonal population of host cells by in vitro transforming the host cells with a plasmid carrying an artificial sequence of a nucleotide encoding the antibodies.

As used herein, the term "hybridoma" or "hybridoma cell" refers to a cell or cell line (typically a myeloma or lymphoma cell) produced by the fusion of antibody-producing lymphocytes and antibody-producing cancer cells. As is known to one of ordinary skill in the art, hybridomas can proliferate and continue to supply to produce specific monoclonal antibodies. Methods for producing hybridomas are known in the art (see, for example, Harlow & Lane, 1988). The term "hybridoma" or "hybridoma cell" when referred herein also includes subclones and progeny cells of the hybridoma.

As used herein, "conventional antibody" refers to an antibody comprising two heavy chains (which may be designated H and H') and two light chains (which may be designated L and L') and two antigen-binding sites, wherein each heavy chain can be a full length immunoglobulin heavy chain or any functional region thereof that retain the antigen binding ability (for example, the heavy chains include, but not limited to, VH chains, VH-CH1 chains, and VH-CH1-CH2-CH3 chains), and each light chain can be a full length light chain or any functional region (e.g., light chains include, but not limited to, VL chains and VL-CL chains). Each heavy chain (H and H') is paired with a light chain (L and L', respectively).

As used herein, a full length antibody is an antibody comprising two full length heavy chains (e.g., VH-CH1-CH2-CH3 or VH-CH1-CH2-CH3-CH4) and two full length light chains (VL-CL) and a hinge region, for example, an antibody naturally produced by secretion of the antibody by B cells, and a synthetically-produced antibody having the same domain.

As used herein, dsFv refers to an Fv having an engineered intermolecular disulfide bond which stabilizes the VH-VL pair.

As used herein, a Fab fragment is an antibody fragment that results from digestion of a full-length immunoglobulin with papain, or a fragment having the same structure, which is synthesized or produced, for example, by recombinant methods. The Fab fragment comprises a light chain (comprising VL and CL) and another chain comprising a variable domain (VH) of the heavy chain and a constant region domain (CH1) of the heavy chain.

As used herein, an F(ab')2 fragment is an antibody fragment that results from digestion of an immunoglobulin with pepsin at pH 4.0-4.5, or a fragment having the same structure, which is synthesized or produced, for example, by recombinant methods. A F(ab')2 fragment essentially comprises two Fab fragments, wherein each heavy chain portion comprises an additional few amino acids, including cysteines that forms a disulfide bond connecting the two fragments.

As used herein, a Fab' fragment is a fragment comprising half of a F(ab')2 fragment (comprising ne heavy chain and one light chain).

As used herein, a scFv fragment refers to an antibody fragment comprising a variable light chain (VL) and a variable heavy chain (VH) covalently linked by a polypeptide linker in any order. The linker is of a length such that the two variable domains are bridged without substantial interference. Exemplary linkers are (Gly-Ser)n residues with some Glu or Lys residues dispersed throughout to increase solubility.

The term "chimeric antibody" refers to an antibody in which the variable region sequence is derived from one species and the constant region sequence is derived from another species, for example, in which the variable region sequence is derived from a mouse antibody and the constant region sequence is derived from a human antibody.

"Humanized" antibody refers to a non-human (e.g., mouse) antibody form that is a chimeric immunoglobulin, immunoglobulin chain, or a fragment thereof (e.g., Fv, Fab, Fab', F(ab')2 or other antigen-binding subsequences of antibodies), and contains minimal sequences derived from non-human immunoglobulins. Preferably, the humanized antibody is a human immunoglobulin (recipient antibody) in which residues of the complementarity determining region (CDR) of the recipient antibody are replaced by residues of the CDR of a non-human species (donor antibody) having the desired specificity, affinity, and capacity, such as mouse, rat, rabbit.

Furthermore, it is also possible in humanization process to mutate amino acid residues within the CDR1, CDR2 and/or CDR3 regions of VH and/or VL, thereby improving one or more binding properties (e.g., affinity) of the antibody. Mutations can be introduced, for example, by PCR-mediation, the effect of the mutations on antibody binding or other functional properties can be assessed using in vitro or in vivo assays as described herein. Typically, conservative mutations are introduced. Such mutations may be amino acid substitutions, additions or deletions. In addition, the number of mutations within the CDRs is usually one or at most two. Thus, the humanized antibodies of the present invention also encompass antibodies comprising one or two amino acid mutations within the CDRs.

As used herein, the term "epitope" refers to any antigenic determinant on an antigen to which the paratope of an antibody binds. Epitopic determinants usually comprise chemically active surface groupings of molecules such as amino acids or sugar side chains, and typically have specific three dimensional structural characteristics, as well as specific charge characteristics.

As used herein, a variable domain or variable region is a specific Ig domain of the heavy or light chain of an antibody, comprising an amino acid sequence that varies between different antibodies. Each light chain and each heavy chain have a variable region domain VL and VH, respectively. The variable domain provides antigen specificity and is therefore responsible for antigen recognition. Each variable region comprises a CDR and a framework region (FR), wherein the CDR is a part of an antigen-binding site domain.

As used herein, "antigen-binding domain" and "antigen-binding site" are used synonymously to refer to a domain within an antibody that recognizes and physically interacts with a cognate antigen. Native conventional full length antibody molecules have two conventional antigen-binding sites, each comprising a heavy chain variable region portion and a light chain variable region portion. Conventional antigen-binding sites comprise a loop connecting the antiparallel beta strands within the variable region domain. The antigen-binding site may comprise other portions of the variable region domain. Each conventional antigen-binding site comprises 3 hypervariable regions from the heavy chain and 3 hypervariable regions from the light chain. The hypervariable regions are also referred to as complementarity determining regions (CDRs).

As used herein, "hypervariable region", "HV", "complementarity determining region" and "CDR" and "antibody CDR" are used interchangeably to refer to one of a plurality of portions within each variable region that together form an antigen binding site of the antibody. Each variable region domain contains 3 CDRs, designated as CDR1, CDR2 and CDR3. For example, the light chain variable region domain comprises 3 CDRs, designated as VL CDR1, VL CDR2 and VL CDR3; the heavy chain variable region domain comprises 3 CDRs, designated as VH CDR1, VH CDR2 and VH CDR3. 3 CDRs in the variable region are discontinuous along the linear amino acid sequence, but are in close proximity in the folded polypeptide. The CDRs are located within the loop connecting the parallel strand of the beta sheet of the variable domains. As described herein, a person skilled in the art are aware of and can identify CDRs based on Kabat or Chothia numbering (see, for example, Kabat, E. A. et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917).

As used herein, a framework region (FR) is a domain in an antibody variable region domain in a beta sheet; in terms of amino acid sequence, the FR region is relatively more conserved than the hypervariable region.

As used herein, a "constant region" domain is a domain in an antibody heavy or light chain that comprises an amino acid sequence that is relatively more conserved than the amino acid sequence of the variable region domain. In a conventional full length antibody molecule, each light chain has a single light chain constant region (CL) domain, and each heavy chain comprises one or more heavy chain constant region (CH) domains, including CH1, CH2, CH3 and CH4. The full length IgA, IgD and IgG isotypes comprise CH1, CH2, CH3 and the hinge region, whereas IgE and IgM comprise CH1, CH2, CH3 and CH4. The CH1 and CL domains extend the Fab arm of the antibody molecule, thus facilitating interaction with the antigen and rotation of the antibody arm. The constant region of an antibody can perform an effector function, for example, but not limited to, clearance of antigens, pathogens, and toxins to which the antibody specifically binds, such as by interaction with various cells, biomolecules, and tissues.

As used herein, a functional region of an antibody is an antibody portion comprising at least VH, VL, CH (e.g., CH1, CH2 or CH3), CL or a hinge region domain or at least a functional region thereof of the antibody.

As used herein, a functional region of a VH domain is at least a portion of an intact VH domain that retains at least part of the binding specificity of the entire VH domain (e.g., by retaining one or more CDRs of the entire VH domain), such that the functional region of the VH domain binds to the antigen either alone or in combination with another antibody domain (e.g., a VL domain) or a region thereof. The functional region of an exemplary VH domain is a region comprising CDR1, CDR2 and/or CDR3 of the VH domain.

As used herein, a functional region of a VL domain is at least a portion of an intact VL domain that retains at least part of the binding specificity of the entire VL domain (e.g., by retaining one or more CDRs of the entire VL domain), such that the functional region of the VL domain binds to the antigen either alone or in combination with another antibody domain (e.g., a VH domain) or a region thereof. The functional region of an exemplary VL domain is a region comprising CDR1, CDR2 and/or CDR3 of the VL domain.

As used herein, "specifically bind" or "immunospecifically binding" with respect to an antibody or antigen-binding fragment thereof is used interchangeably herein and refers to the ability of an antibody or antigen-binding fragment to form one or more non-covalent bonds with an alloantigen via non-covalent interactions between the antibody and the antibody-binding site of the antigen. The antigen can be an isolated antigen or present in a tumor cell. Typically, an antibody that immunospecifically binds (or specifically binds) to an antigen binds to the antigen with an affinity constant Ka of about $1\times10^7 M^{-1}$ or $1\times10^8 M^{-1}$ or more (or with a dissociation constant (Kd) of $1\times10^{-7} M$ or $1\times10^{-8} M$ or less). Affinity constants can be determined by standard kinetic methods of antibody responses, for example, immunoassays, surface plasmon resonance (SPR) (Rich and Myszka (2000) Curr. Opin. Biotechnol 11:54; Englebienne (1998) Analyst. 123:1599), isothermal titration calorimetry (ITC) or other kinetic interaction assays known in the art (see, for example, Paul, ed., Fundamental Immunology, 2nd ed., Raven Press, New York, pages 332-336 (1989); see also U.S. Pat. No. 7,229,619, which describes exemplary SPR and ITC methods for calculating the binding affinity of antibodies). Instruments and methods for detecting and monitoring the rate of binding in real time are known and commercially available (see, BiaCore 2000, Biacore AB, Upsala, Sweden and GE Healthcare Life Sciences; Malmqvist (2000) Biochem. Soc. Trans. 27:335).

As used herein, the term "competing" with respect to an antibody means that a first antibody or antigen-binding fragment thereof binds to an epitope in a manner sufficiently similar to a second antibody or antigen-binding fragment thereof, and thus the binding result of the first antibody to the associated epitope thereof is detectably reduced in the presence of the second antibody compared to that in the absence of the second antibody; alternatively, the binding of the second antibody to the associated epitope thereof may be, but not necessarily, detectably reduced in the presence of the first antibody compared to that in the absence of the first antibody. That is to say, the first antibody can inhibit the binding of the second antibody to the epitope thereof, however, the second antibody is not necessarily to inhibit the binding of the first antibody to the corresponding epitope thereof. However, in the case where each antibody can detectably inhibit the binding of another antibody to the associated epitope or ligand thereof, whether in an identical, higher or lower degree, the antibodies are referred to as "cross-competitively" binding to the corresponding epitope thereof. Both competing and cross-competing antibodies are encompassed by the present invention. Regardless of the mechanism of such competing or cross-competing (e.g., steric hindrance, conformational change, or binding to a common epitope or a fragment thereof), a person skilled in the art will recognize that, based on the teachings provided in the present invention, that such competing and/or cross-competing antibodies are encompassed by the present invention and can be used in the methods disclosed herein.

As used herein, "polypeptide" refers to two or more amino acids which are linked covalently. The terms "polypeptide" and "protein" are used interchangeably herein.

"Isolated protein", "isolated polypeptide" or "isolated antibody" refers to a protein, polypeptide or antibody: (1) is not associated with naturally associated components that accompany it in its native state; (2) is free of other proteins from the same species; (3) is expressed by a cell from a different species; or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, i.e., using the protein purification technique well known in the art.

Suitable conservative amino acid substitutions in peptides or proteins are known to a person skilled in the art and can generally be carried out without altering the biological activity of the resulting molecule. Typically, a person skilled in the art will recognize that a single amino acid substitution in a non-essential region of a polypeptide does not substantially alter the biological activity (see, for example, Watson et al., Molecular Biology of the Gene, 4th Edition, 1987, The Benjamin/Cummings Pub.co., p. 224).

As used herein, the terms "polynucleotide" and "nucleic acid molecule" refer to an oligomer or polymer comprising at least two linked nucleotides or nucleotide derivatives, including deoxyribonucleic acid (DNA) and ribonucleic acid (RNA), which are usually linked by a phosphodiester bond.

As used herein, an isolated nucleic acid molecule is a nucleic acid molecule which is isolated from other nucleic acid molecules present in the natural source of the nucleic acid molecule. An "isolated" nucleic acid molecule of, for example, a cDNA molecule, can be substantially free of other cellular material or culture medium when prepared by recombinant techniques, or substantially free of chemical precursors or other chemical components during the chemical synthesis. Exemplary isolated nucleic acid molecules provided herein include isolated nucleic acid molecules encoding the provided antibodies or antigen-binding fragments.

"identical" or "identity" with respect to a sequence has well-recognized meaning in the art, and the percentage of sequence identity between two nucleic acid or polypeptide molecules or regions can be calculated using the disclosed techniques. Sequence identity can be measured along the entire length of a polynucleotide or polypeptide or along a region of the molecule. (See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Although there are many methods for measuring the identity between two polynucleotides or polypeptides, the term "identity" is well known to a person skilled person (Carrillo, H. & Lipman, D., SIAM J Applied Math 48:1073(1988)).

As used herein, "operably linked" with respect to a nucleic acid sequence, region, element or domain means that the nucleic acid regions are functionally related to each other. For example, a promoter can be operably linked to a nucleic acid encoding a polypeptide which enables the promoter to regulate or mediate the transcription of the nucleic acid.

As used herein, "expression" refers to the process by which a polypeptide is produced by transcription and translation of a polynucleotide. The expression level of a polypeptide can be assessed using any method known in the art, including, for example, methods for determining the amount of polypeptides produced from a host cell. Such methods can include, but not limited to, quantification of polypeptides in cell lysates by ELISA, Coomassie blue staining after gel electrophoresis, Lowry protein assays, and Bradford protein assays.

As used herein, a "host cell" refers to a cell used to receive, maintain, replicate, and amplify a vector. Host cells can also be used to express the polypeptide encoded by the vector. The nucleic acid contained in the vector replicates when the host cell divides, thereby amplifying the nucleic acid. Host cells can be eukaryotic cells or prokaryotic cells.

Suitable host cells include, but not limited to, CHO cells, various COS cells, HeLa cells, HEK cells such as HEK 293 cells.

"Codon optimization" refers to a method for modifying a nucleic acid sequence for enhanced expression in a host cell of interest by replacing at least one codon (e.g., about or more than about 1, 2, 3, 4, 5, 10, 15, 20, 25, 50 or more codons) of the native sequence with codons that are more frequently or most frequently used in the genes of the host cell while maintaining the native amino acid sequence. Various species exhibit particular bias for certain codons of a particular amino acid. Codon preference (a difference in codon usage between organisms) usually correlates with the efficiency of translation of messenger RNA (mRNA), which is in turn believed to be dependent on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the Codon Usage Database available at www.kazusa.orjp/codon/, and these tables can be adapted in different ways. See, Nakamura Y et al., "Codon usage tabulated from the international DNA sequence databases: status for the year 2000. Nucl. Acids Res., 28:292(2000).

As used herein, a "vector" is a replicable nucleic acid and when a vector is transformed into a suitable host cell, one or more heterologous proteins can be expressed from the vector. The vector as used herein includes the vector into which a nucleic acid encoding a polypeptide or a fragment thereof can be introduced, typically, by restriction digestion and ligation. The vector as used herein also includes the vector comprising a nucleic acid encoding a polypeptide. The vector is used to introduce a nucleic acid encoding a polypeptide into a host cell, to amplify the nucleic acid, or to express/display a polypeptide encoded by a nucleic acid. The vector typically remains free, but can be designed to integrate the gene or a part thereof into the chromosome of the genome. The vectors of artificial chromosomes, such as yeast artificial vectors and mammalian artificial chromosomes, are also taken into consideration. The selection and use of such vehicles are well known to a person skilled in the art.

As used herein, vectors also include "viral vectors" or "vectors of viruses". The vector of virus is an engineered virus, which can be operably linked to an exogenous gene to transfer (as a vehicle or shuttle) the exogenous gene into a cell.

As used herein, an "expression vector" includes a vector capable of expressing DNA, which can be operably linked to a regulatory sequence, such as a promoter region, that is capable of affecting expression of such DNA fragments. Such additional fragments may include promoter and terminator sequences, and may optionally include one or more origins of replication, one or more selectable markers, an enhancer, a polyadenylation signal, etc. Expression vectors are generally derived from plasmid or viral DNA, or may contain elements of both. Thus, an expression vector refers to a recombinant DNA or RNA construct, such as a plasmid, phage, recombinant virus, or other vector which, when introduced into a suitable host cell, results in expression of the cloned DNA. Suitable expression vectors are well known to a person skilled in the art and include expression vectors which are replicable in eukaryotic cells and/or prokaryotic cells, and expression vectors which retain free or expression vectors which are integrated into the genome of a host cell.

As used herein, "treating" an individual having a disease or condition means that the symptoms of the individual are partially or totally relieved, or unchanged after treatment. Thus, treating includes preventing, treating, and/or curing. Preventing refers to the prevention of underlying diseases and/or prevention of worsening symptoms or disease progression. Treating also includes any pharmaceutical use of any of the provided antibodies or antigen-binding fragments thereof and the compositions provided herein.

As used herein, "therapeutic effect" refers to an effect caused by the treatment in an individual that alters, generally ameliorates or improves the symptoms of diseases or conditions, or cures diseases or conditions.

As used herein, "therapeutically effective amount" or "therapeutically effective dose" refers to an amount of a substance, compound, material, or composition comprising the compound which is at least sufficient to produce a therapeutic effect when administered to a subject. Thus, it is an amount essential for preventing, curing, ameliorating, blocking or partially blocking the symptoms of a disease or condition.

As used herein, "prophylactically effective amount" or "prophylactically effective dose" refers to an amount of a substance, compound, material or composition comprising the compound which exerts the desired prophylactic effect when administered to a subject, e.g., to prevent or delay the onset or recurrence of a disease or symptom, reduce the likelihood of the occurring or recurring of a disease or symptom. The complete prophylacti effective dose does not necessarily occur by administration of one dose and can occur upon administration of a series of doses. Thus, a prophylactically effective amount can be administered in one or more administrations.

As used herein, the term "patient" refers to a mammal, such as human.

In one aspect, the disclosure relates to an antibody or a functional fragment thereof, comprising a heavy chain CDR selected from the amino acid sequences SEQ ID NO: 2-4, 12-14, 22-24, 32-34, 42-44, 52-54, 62-64, 72-74, 82-84, 92-94, 102-104, 112-114, 122-124, 132-134, 142-144, 152-154, 162-164, 172-174, 177-179, 182-184, 187-189, 192-194, 197-199, 202-204, 207-209 or any variant thereof, and/or a light chain CDR selected from the amino acid sequences SEQ ID NO: 7-9, 17-19, 27-29, 37-39, 47-49, 57-59, 67-69, 77-79, 87-89, 97-99, 107-109, 117-119, 127-129, 137-139, 147-149, 157-159, 167-169, 212-214, 217-219, 222-224, 227-229 or any variant thereof.

In one aspect, the disclosure relates to an antibody or a functional fragment thereof, comprising a heavy chain CDR1 selected from the amino acid sequences SEQ ID NO: 2, 12, 22, 32, 42, 52, 62, 72, 82, 92, 102, 112, 122, 132, 142, 152, 162, 172, 177, 182, 187, 192, 197, 202, 207 or any variant thereof, a heavy chain CDR2 selected from the amino acid sequences SEQ ID NO: 3, 13, 23, 33, 43, 53, 63, 73, 83, 93, 103, 113, 123, 133, 143, 153, 163, 173, 178, 183, 188, 193, 198, 203, 208 or any variant thereof, and a heavy chain CDR3 selected from the amino acid sequences SEQ ID NO: 4, 14, 24, 34, 44, 54, 64, 74, 84, 94, 104, 114, 124, 134, 144, 154, 164, 174, 179, 184, 189, 194, 199, 204, 209 or any variant thereof, and/or a light chain CDR1 selected from the amino acid sequences SEQ ID NO: 7, 17, 27, 37, 47, 57, 67, 77, 87, 97, 107, 117, 127, 137, 147, 157, 167, 212, 217, 222, 227 or any variant thereof, a light chain CDR2 selected from the amino acid sequences SEQ ID NO:

8, 18, 28, 38, 48, 58, 68, 78, 88, 98, 108, 118, 128, 138, 148, 158, 168, 213, 218, 223, 228 or any variant thereof, and a light chain CDR3 selected from the amino acid sequences SEQ ID NO: 9, 19, 29, 39, 49, 59, 69, 79, 89, 99, 109, 119, 129, 139, 149, 159, 169, 214, 219, 224, 229 or any variant thereof.

In one aspect, the disclosure relates to an antibody or a functional fragment thereof, comprising a heavy chain variable region selected from the amino acid sequences SEQ ID NO: 1, 11, 21, 31, 41, 51, 61, 71, 81, 91, 101, 111, 121, 131, 141, 151, 161, 171, 176, 181, 186, 191, 196, 201, 206 or any variant thereof, and/or a light chain variable region selected from the amino acid sequences SEQ ID NO: 6, 16, 26, 36, 46, 56, 66, 76, 86, 96, 106, 116, 126, 136, 146, 156, 166, 211, 216, 221, 226 or any variant thereof.

In one aspect, the disclosure relates to an antibody or a functional fragment thereof, comprising a heavy chain CDR1 selected from the amino acid sequence SEQ ID NO: 2, a heavy chain CDR2 selected from the amino acid sequence SEQ ID NO: 3, and a heavy chain CDR3 selected from the amino acid sequence SEQ ID NO: 4; and/or a light chain CDR1 selected from the amino acid sequence SEQ ID NO: 7, a light chain CDR2 selected from the amino acid sequence SEQ ID NO: 8, and a light chain CDR3 selected from the amino acid sequence SEQ ID NO: 9.

In one aspect, the disclosure relates to an antibody or a functional fragment thereof, comprising a heavy chain CDR1 selected from the amino acid sequence SEQ ID NO: 12, a heavy chain CDR2 selected from the amino acid sequence SEQ ID NO: 13, and a heavy chain CDR3 selected from the amino acid sequence SEQ ID NO: 14; and/or a light chain CDR1 selected from the amino acid sequence SEQ ID NO: 17, a light chain CDR2 selected from the amino acid sequence SEQ ID NO: 18, and a light chain CDR3 selected from the amino acid sequence SEQ ID NO: 19.

In one aspect, the disclosure relates to an antibody or a functional fragment thereof, comprising a heavy chain CDR1 selected from the amino acid sequence SEQ ID NO: 22, a heavy chain CDR2 selected from the amino acid sequence SEQ ID NO: 23, and a heavy chain CDR3 selected from the amino acid sequence SEQ ID NO: 24; and/or a light chain CDR1 selected from the amino acid sequence SEQ ID NO: 27, a light chain CDR2 selected from the amino acid sequence SEQ ID NO: 28, and a light chain CDR3 selected from the amino acid sequence SEQ ID NO: 29.

In one aspect, the disclosure relates to an antibody or a functional fragment thereof, comprising a heavy chain CDR1 selected from the amino acid sequence SEQ ID NO: 32, a heavy chain CDR2 selected from the amino acid sequence SEQ ID NO: 33, and a heavy chain CDR3 selected from the amino acid sequence SEQ ID NO: 34; and/or a light chain CDR1 selected from the amino acid sequence SEQ ID NO: 37, a light chain CDR2 selected from the amino acid sequence SEQ ID NO: 38, and a light chain CDR3 selected from the amino acid sequence SEQ ID NO: 39.

In one aspect, the disclosure relates to an antibody or a functional fragment thereof, comprising a heavy chain CDR1 selected from the amino acid sequence SEQ ID NO: 42, a heavy chain CDR2 selected from the amino acid sequence SEQ ID NO: 43, and a heavy chain CDR3 selected from the amino acid sequence SEQ ID NO: 44; and/or a light chain CDR1 selected from the amino acid sequence SEQ ID NO: 47, a light chain CDR2 selected from the amino acid sequence SEQ ID NO: 48, and a light chain CDR3 selected from the amino acid sequence SEQ ID NO: 49.

In one aspect, the disclosure relates to an antibody or a functional fragment thereof, comprising a heavy chain CDR1 selected from the amino acid sequence SEQ ID NO: 52, a heavy chain CDR2 selected from the amino acid sequence SEQ ID NO: 53, and a heavy chain CDR3 selected from the amino acid sequence SEQ ID NO: 54; and/or a light chain CDR1 selected from the amino acid sequence SEQ ID NO: 57, a light chain CDR2 selected from the amino acid sequence SEQ ID NO: 58, and a light chain CDR3 selected from the amino acid sequence SEQ ID NO: 59.

In one aspect, the disclosure relates to an antibody or a functional fragment thereof, comprising a heavy chain CDR1 selected from the amino acid sequence SEQ ID NO: 62, a heavy chain CDR2 selected from the amino acid sequence SEQ ID NO: 63, and a heavy chain CDR3 selected from the amino acid sequence SEQ ID NO: 64; and/or a light chain CDR1 selected from the amino acid sequence SEQ ID NO: 67, a light chain CDR2 selected from the amino acid sequence SEQ ID NO: 68, and a light chain CDR3 selected from the amino acid sequence SEQ ID NO: 69.

In one aspect, the disclosure relates to an antibody or a functional fragment thereof, comprising a heavy chain CDR1 selected from the amino acid sequence SEQ ID NO: 72, a heavy chain CDR2 selected from the amino acid sequence SEQ ID NO: 73, and a heavy chain CDR3 selected from the amino acid sequence SEQ ID NO: 74; and/or a light chain CDR1 selected from the amino acid sequence SEQ ID NO: 77, a light chain CDR2 selected from the amino acid sequence SEQ ID NO: 78, and a light chain CDR3 selected from the amino acid sequence SEQ ID NO: 79.

In one aspect, the disclosure relates to an antibody or a functional fragment thereof, comprising a heavy chain CDR1 selected from the amino acid sequence SEQ ID NO: 82, a heavy chain CDR2 selected from the amino acid sequence SEQ ID NO: 83, and a heavy chain CDR3 selected from the amino acid sequence SEQ ID NO: 84; and/or a light chain CDR1 selected from the amino acid sequence SEQ ID NO: 87, a light chain CDR2 selected from the amino acid sequence SEQ ID NO: 88, and a light chain CDR3 selected from the amino acid sequence SEQ ID NO: 89.

In one aspect, the disclosure relates to an antibody or a functional fragment thereof, comprising a heavy chain CDR1 selected from the amino acid sequence SEQ ID NO: 92, a heavy chain CDR2 selected from the amino acid sequence SEQ ID NO: 93, and a heavy chain CDR3 selected from the amino acid sequence SEQ ID NO: 94; and/or a light chain CDR1 selected from the amino acid sequence SEQ ID NO: 97, a light chain CDR2 selected from the amino acid sequence SEQ ID NO: 98, and a light chain CDR3 selected from the amino acid sequence SEQ ID NO: 99.

In one aspect, the disclosure relates to an antibody or a functional fragment thereof, comprising a heavy chain CDR1 selected from the amino acid sequence SEQ ID NO: 102, a heavy chain CDR2 selected from the amino acid sequence SEQ ID NO: 103, and a heavy chain CDR3 selected from the amino acid sequence SEQ ID NO: 104; and/or a light chain CDR1 selected from the amino acid sequence SEQ ID NO: 107, a light chain CDR2 selected from the amino acid sequence SEQ ID NO: 108, and a light chain CDR3 selected from the amino acid sequence SEQ ID NO: 109.

In one aspect, the disclosure relates to an antibody or a functional fragment thereof, comprising a heavy chain CDR1 selected from the amino acid sequence SEQ ID NO: 112, a heavy chain CDR2 selected from the amino acid sequence SEQ ID NO: 113, and a heavy chain CDR3 selected from the amino acid sequence SEQ ID NO: 114; and/or a light chain CDR1 selected from the amino acid sequence SEQ ID NO: 117, a light chain CDR2 selected from the amino acid sequence SEQ ID NO: 118, and a light chain CDR3 selected from the amino acid sequence SEQ ID NO: 119.

In one aspect, the disclosure relates to an antibody or a functional fragment thereof, comprising a heavy chain CDR1 selected from the amino acid sequence SEQ ID NO: 122, a heavy chain CDR2 selected from the amino acid sequence SEQ ID NO: 123, and a heavy chain CDR3 selected from the amino acid sequence SEQ ID NO: 124; and/or a light chain CDR1 selected from the amino acid sequence SEQ ID NO: 127, a light chain CDR2 selected from the amino acid sequence SEQ ID NO: 128, and a light chain CDR3 selected from the amino acid sequence SEQ ID NO: 129.

In one aspect, the disclosure relates to an antibody or a functional fragment thereof, comprising a heavy chain CDR1 selected from the amino acid sequence SEQ ID NO: 132, a heavy chain CDR2 selected from the amino acid sequence SEQ ID NO: 133, and a heavy chain CDR3 selected from the amino acid sequence SEQ ID NO: 134; and/or a light chain CDR1 selected from the amino acid sequence SEQ ID NO: 137, a light chain CDR2 selected from the amino acid sequence SEQ ID NO: 138, and a light chain CDR3 selected from the amino acid sequence SEQ ID NO: 139.

In one aspect, the disclosure relates to an antibody or a functional fragment thereof, comprising a heavy chain CDR1 selected from the amino acid sequence SEQ ID NO: 142, a heavy chain CDR2 selected from the amino acid sequence SEQ ID NO: 143, and a heavy chain CDR3 selected from the amino acid sequence SEQ ID NO: 144; and/or a light chain CDR1 selected from the amino acid sequence SEQ ID NO: 147, a light chain CDR2 selected from the amino acid sequence SEQ ID NO: 148, and a light chain CDR3 selected from the amino acid sequence SEQ ID NO: 149.

In one aspect, the disclosure relates to an antibody or a functional fragment thereof, comprising a heavy chain CDR1 selected from the amino acid sequence SEQ ID NO: 152, a heavy chain CDR2 selected from the amino acid sequence SEQ ID NO: 153, and a heavy chain CDR3 selected from the amino acid sequence SEQ ID NO: 154; and/or a light chain CDR1 selected from the amino acid sequence SEQ ID NO: 157, a light chain CDR2 selected from the amino acid sequence SEQ ID NO: 158, and a light chain CDR3 selected from the amino acid sequence SEQ ID NO: 159.

In one aspect, the disclosure relates to an antibody or a functional fragment thereof, comprising a heavy chain CDR1 selected from the amino acid sequence SEQ ID NO: 162, a heavy chain CDR2 selected from the amino acid sequence SEQ ID NO: 163, and a heavy chain CDR3 selected from the amino acid sequence SEQ ID NO: 164; and/or a light chain CDR1 selected from the amino acid sequence SEQ ID NO: 167, a light chain CDR2 selected from the amino acid sequence SEQ ID NO: 168, and a light chain CDR3 selected from the amino acid sequence SEQ ID NO: 169.

In one aspect, the disclosure relates to an antibody or a functional fragment thereof, comprising a heavy chain CDR1 selected from the amino acid sequence SEQ ID NO: 172, a heavy chain CDR2 selected from the amino acid sequence SEQ ID NO: 173, and a heavy chain CDR3 selected from the amino acid sequence SEQ ID NO: 174; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 182, a heavy chain CDR2 selected from the amino acid sequence SEQ ID NO: 183, and a heavy chain CDR3 selected from the amino acid sequence SEQ ID NO: 184; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 187, a heavy chain CDR2 selected from the amino acid sequence SEQ ID NO: 188, and a heavy chain CDR3 selected from the amino acid sequence SEQ ID NO: 189; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 192, a heavy chain CDR2 selected from the amino acid sequence SEQ ID NO: 193, and a heavy chain CDR3 selected from the amino acid sequence SEQ ID NO: 194; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 197, a heavy chain CDR2 selected from the amino acid sequence SEQ ID NO: 198, and a heavy chain CDR3 selected from the amino acid sequence SEQ ID NO: 199; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 202, a heavy chain CDR2 selected from the amino acid sequence SEQ ID NO: 203, and a heavy chain CDR3 selected from the amino acid sequence SEQ ID NO: 204; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 207, a heavy chain CDR2 selected from the amino acid sequence SEQ ID NO: 208, and a heavy chain CDR3 selected from the amino acid sequence SEQ ID NO: 209; and/or a light chain CDR1 selected from the amino acid sequence SEQ ID NO: 212, a light chain CDR2 selected from the amino acid sequence SEQ ID NO: 213, and a light chain CDR3 selected from the amino acid sequence SEQ ID NO: 214.

In one aspect, the disclosure relates to an antibody or a functional fragment thereof, comprising a heavy chain CDR1 selected from the amino acid sequence SEQ ID NO: 172, a heavy chain CDR2 selected from the amino acid sequence SEQ ID NO: 173, and a heavy chain CDR3 selected from the amino acid sequence SEQ ID NO: 174; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 177, a heavy chain CDR2 selected from the amino acid sequence SEQ ID NO: 178, and a heavy chain CDR3 selected from the amino acid sequence SEQ ID NO: 179; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 182, a heavy chain CDR2 selected from the amino acid sequence SEQ ID NO: 183, and a heavy chain CDR3 selected from the amino acid sequence SEQ ID NO: 184; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 187, a heavy chain CDR2 selected from the amino acid sequence SEQ ID NO: 188, and a heavy chain CDR3 selected from the amino acid sequence SEQ ID NO: 189; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 192, a heavy chain CDR2 selected from the amino acid sequence SEQ ID NO: 193, and a heavy chain CDR3 selected from the amino acid sequence SEQ ID NO: 194; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 197, a heavy chain CDR2 selected from the amino acid sequence SEQ ID NO: 198, and a heavy chain CDR3 selected from the amino acid sequence SEQ ID NO: 199; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 202, a heavy chain CDR2 selected from the amino acid sequence SEQ ID NO: 203, and a heavy chain CDR3 selected from the amino acid sequence SEQ ID NO: 204; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 207, a heavy chain CDR2 selected from the amino acid sequence SEQ ID NO: 208, and a heavy chain CDR3 selected from the amino acid sequence SEQ ID NO: 209; and/or a light chain CDR1 selected from the amino acid sequence SEQ ID NO: 217, a light chain CDR2 selected from the amino acid sequence SEQ ID NO: 218, and a light chain CDR3 selected from the amino acid sequence SEQ ID NO: 219.

In one aspect, the disclosure relates to an antibody or a functional fragment thereof, comprising a heavy chain CDR1 selected from the amino acid sequence SEQ ID NO: 172, a heavy chain CDR2 selected from the amino acid sequence SEQ ID NO: 173, and a heavy chain CDR3 selected from the amino acid sequence SEQ ID NO: 174; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 177, a heavy chain CDR2 selected from the amino acid sequence SEQ ID NO: 178, and a heavy chain CDR3 selected from the amino acid sequence SEQ ID NO: 179; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 182, a heavy chain CDR2 selected from the amino acid sequence SEQ ID NO: 183, and a heavy chain CDR3 selected from the amino acid sequence SEQ ID NO: 184; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 187, a heavy chain CDR2 selected from the amino acid sequence SEQ ID NO: 188, and a heavy chain CDR3 selected from the amino acid sequence SEQ ID NO: 189; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 192, a heavy chain CDR2 selected from the amino acid sequence SEQ ID NO: 193, and a heavy chain CDR3 selected from the amino acid sequence SEQ ID NO: 194; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 197, a heavy chain CDR2 selected from the amino acid sequence SEQ ID NO: 198, and a heavy chain CDR3 selected from the amino acid sequence SEQ ID NO: 199; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 202, a heavy chain CDR2 selected from the amino acid sequence SEQ ID NO: 203, and a heavy chain CDR3 selected from the amino acid sequence SEQ ID NO: 204; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 207, a heavy chain CDR2 selected from the amino acid sequence SEQ ID NO: 208, and a heavy chain CDR3 selected from the amino acid sequence SEQ ID NO: 209; and/or a light chain CDR1 selected from the amino acid sequence SEQ ID NO: 222, a light chain CDR2 selected from the amino acid sequence SEQ ID NO: 223, and a light chain CDR3 selected from the amino acid sequence SEQ ID NO: 224.

In one aspect, the disclosure relates to an antibody or a functional fragment thereof, comprising a heavy chain CDR1 selected from the amino acid sequence SEQ ID NO: 172, a heavy chain CDR2 selected from the amino acid sequence SEQ ID NO: 173, and a heavy chain CDR3 selected from the amino acid sequence SEQ ID NO: 174; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 177, a heavy chain CDR2 selected from the amino acid sequence SEQ ID NO: 178, and a heavy chain CDR3 selected from the amino acid sequence SEQ ID NO: 179; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 182, a heavy chain CDR2 selected from the amino acid sequence SEQ ID NO: 183, and a heavy chain CDR3 selected from the amino acid sequence SEQ ID NO: 184; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 187, a heavy chain CDR2 selected from the amino acid sequence SEQ ID NO: 188, and a heavy chain CDR3 selected from the amino acid sequence SEQ ID NO: 189; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 192, a heavy chain CDR2 selected from the amino acid sequence SEQ ID NO: 193, and a heavy chain CDR3 selected from the amino acid sequence SEQ ID NO: 194; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 197, a heavy chain CDR2 selected from the amino acid sequence SEQ ID NO: 198, and a heavy chain CDR3 selected from the amino acid sequence SEQ ID NO: 199; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 202, a heavy chain CDR2 selected from the amino acid sequence SEQ ID NO: 203, and a heavy chain CDR3 selected from the amino acid sequence SEQ ID NO: 204; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain CDR1 selected from the amino acid sequence SEQ ID NO: 207, a heavy chain CDR2 selected from the amino acid sequence SEQ ID NO: 208, and a heavy chain CDR3 selected from the amino acid sequence SEQ ID NO: 209; and/or a light chain CDR1 selected from the amino acid sequence SEQ ID NO: 227, a light chain CDR2 selected from the amino acid sequence SEQ ID NO: 228, and a light chain CDR3 selected from the amino acid sequence SEQ ID NO: 229.

In one aspect, the disclosure relates to an antibody or a functional fragment thereof, comprising a heavy chain variable region selected from the amino acid sequence SEQ ID NO: 1 or any variant thereof, and/or a light chain variable region selected from the amino acid sequence SEQ ID NO: 6 or any variant thereof.

In one aspect, the disclosure relates to an antibody or a functional fragment thereof, comprising a heavy chain variable region selected from the amino acid sequence SEQ ID NO: 11 or any variant thereof, and/or a light chain variable region selected from the amino acid sequence SEQ ID NO: 16 or any variant thereof.

In one aspect, the disclosure relates to an antibody or a functional fragment thereof, comprising a heavy chain variable region selected from the amino acid sequence SEQ ID NO: 21 or any variant thereof, and/or a light chain variable region selected from the amino acid sequence SEQ ID NO: 26 or any variant thereof.

In one aspect, the disclosure relates to an antibody or a functional fragment thereof, comprising a heavy chain variable region selected from the amino acid sequence SEQ ID NO: 31 or any variant thereof, and/or a light chain variable region selected from the amino acid sequence SEQ ID NO: 36 or any variant thereof.

In one aspect, the disclosure relates to an antibody or a functional fragment thereof, comprising a heavy chain variable region selected from the amino acid sequence SEQ ID NO: 41 or any variant thereof, and/or a light chain variable region selected from the amino acid sequence SEQ ID NO: 46 or any variant thereof.

In one aspect, the disclosure relates to an antibody or a functional fragment thereof, comprising a heavy chain variable region selected from the amino acid sequence SEQ ID NO: 51 or any variant thereof, and/or a light chain variable region selected from the amino acid sequence SEQ ID NO: 56 or any variant thereof.

In one aspect, the disclosure relates to an antibody or a functional fragment thereof, comprising a heavy chain variable region selected from the amino acid sequence SEQ ID NO: 61 or any variant thereof, and/or a light chain variable region selected from the amino acid sequence SEQ ID NO: 66 or any variant thereof.

In one aspect, the disclosure relates to an antibody or a functional fragment thereof, comprising a heavy chain variable region selected from the amino acid sequence SEQ ID NO: 71 or any variant thereof, and/or a light chain variable region selected from the amino acid sequence SEQ ID NO: 76 or any variant thereof.

In one aspect, the disclosure relates to an antibody or a functional fragment thereof, comprising a heavy chain variable region selected from the amino acid sequence SEQ ID NO: 81 or any variant thereof, and/or a light chain variable region selected from the amino acid sequence SEQ ID NO: 86 or any variant thereof.

In one aspect, the disclosure relates to an antibody or a functional fragment thereof, comprising a heavy chain variable region selected from the amino acid sequence SEQ ID NO: 91 or any variant thereof, and/or a light chain variable region selected from the amino acid sequence SEQ ID NO: 96 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 106 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 116 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 116 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 126 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 136 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 146 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 161 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 171 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 176 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 181 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 186 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 191 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 196 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 201 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 206 or any variant thereof, and/or a light chain variable region selected from the amino acid sequence SEQ ID NO: 211 or any variant thereof.

In one aspect, the disclosure relates to an antibody or a functional fragment thereof, comprising a heavy chain variable region selected from the amino acid sequence SEQ ID NO: 171 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 176 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 181 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 186 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 191 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 196 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 201 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 206 or any variant thereof, and/or a light chain variable region selected from the amino acid sequence SEQ ID NO: 216 or any variant thereof.

In one aspect, the disclosure relates to an antibody or a functional fragment thereof, comprising a heavy chain variable region selected from the amino acid sequence SEQ ID NO: 171 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 176 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 181 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 186 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 191 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 196 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 201 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 206 or any variant thereof, and/or a light chain variable region selected from the amino acid sequence SEQ ID NO: 221 or any variant thereof.

In one aspect, the disclosure relates to an antibody or a functional fragment thereof, comprising a heavy chain variable region selected from the amino acid sequence SEQ ID NO: 171 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 176 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 181 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 186 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 191 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 196 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 201 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequence SEQ ID NO: 206 or any variant thereof, and/or a light chain variable region selected from the amino acid sequence SEQ ID NO: 226 or any variant thereof.

In one aspect, the disclosure relates to an antibody or a functional fragment thereof, comprising a heavy chain variable region selected from the amino acid sequences SEQ ID NO: 1, 11, 21, 31, 41, 51, 61, 71, 81, 91, 101, 111, 121, 131, 141, 151, 161, 171, 176, 181, 186, 191, 196, 201, 206 or any variant thereof, and/or a light chain variable region selected from the amino acid sequences SEQ ID NO: 6, 16, 26, 36, 46, 56, 66, 76, 86, 96, 106, 116, 126, 136, 146, 156, 166, 211, 216, 221, 226 or any variant thereof.

In one aspect, the disclosure relates to an isolated nucleic acid sequence encoding the antibody or the functional fragment or variant thereof as disclosed herein, a vector construct comprising a nucleotide sequence encoding the antibody or an IL-4 and/or IL-13 binding portion of the functional fragment of the antibody of the present invention, a host cell containing the vector and a recombinant technology for producing polypeptides.

In one aspect, the disclosure further includes kits, e.g., the kits comprises the antibodies and fragments, homologs, and derivatives thereof, etc. of the disclosure, such as labeled or cytotoxic conjugates, and instructions for use of the antibody, conjugates that kills certain types of cells, etc. The instructions may comprise guidance for in vitro, in vivo, or ex vivo use of the antibodies and the conjugates, etc. The antibody may be in a liquid form or in a solid form, typically in a lyophilized form. The kit may contain other suitable agents such as buffers, reconstitution solutions, and other essential ingredients for the intended use. The packaged combination with predetermined amounts of agents and instructions for use are contemplated, wherein the use is, for example, for therapeutic use or for performing diagnostic assays. Where the antibody is labeled, for example, labeled with an enzyme, the kit may comprise a substrate and a cofactor required for the enzyme (e.g., a substrate precursor which provides a detectable chromophore or fluorophore). In addition, other additives such as stabilizers and buffers (e.g., blocking buffers or lysis buffers) may also be comprised. The relative amounts of the various agents can be varied to provide a concentrate of the agent solution, which provides user flexibility, space savings, agent savings, etc. These agents may also be provided in a dry powder form, typically in a lyophilized form, including excipients which, when dissolved, provide a agent solution with an appropriate concentration.

The antibodies of the present invention are useful in the treatment of mammals. In one embodiment, for example, an antibody of interest or an equivalent is administered to a non-human mammal for the purpose of obtaining preclinical data. Exemplary non-human mammals to be treated include non-human primates, dogs, cats, rodents, and other mammals, on which preclinical studies are performed. Such mammals may be used to establish animal models for a disease to be treated with the antibody or may be used to study toxicity of the antibody of interest. In each of these embodiments, dose escalation studies may be performed on the mammal.

The antibody, whether or not with a second component (such as a therapeutic agent component conjugated thereto), can be used as a therapeutic agent, either alone or in combination with a cytotoxic factor. The present invention relates to antibody-based therapies which comprise administering the antibodies of the present invention to an animal, mammal or human to treat an IL-4 and/or IL-13 mediated disease, disorder or condition.

The term "treating/treatment/treat" as used in the present invention refers to therapeutic treatment and prophylactic or preventive measures. It refers to preventing, curing, reversing, attenuating, ameliorating, minimizing, inhibiting or stopping the harmful effects of the disease state, disease progression, disease-causing factors (e.g., bacteria or viruses) or other abnormal conditions.

Accordingly, the present invention also encompasses multivalent antibodies, including bispecific anti-IL-4/IL-13 antibodies having attached effector molecules, atoms or other substances with diagnostic or therapeutic functions. For example, an antibody may have a radiodiagnostic tag or a radioactive cytotoxic atom or a metal or cytotoxic substance such as a ricin chain, which are attached to the antibody for in vivo diagnosis or treatment of cancer.

Furthermore, the antibodies of the present invention may also be used in immunoassays, purification methods, and other methods in which immunoglobulins or fragments thereof are used. Such uses are well known in the art.

Accordingly, the present invention also provides compositions comprising the anti-IL-13 and/or anti-IL-4 antibody or a fragment thereof of the present invention, wherein the antibody is conveniently combined with pharmaceutically acceptable carriers, diluents or excipients, which is a common means in the art.

The term "pharmaceutical composition" as used herein refers to formulations of various preparations. Formulations containing therapeutically effective amounts of multivalent antibodies are sterile liquid solutions, liquid suspensions or lyophilized forms, and optionally contain stabilizers or excipients.

As used herein, the term "disorder" refers to any condition that would benefit from treatment with the antibody of the present invention. This includes chronic and acute disorders or diseases including those pathological conditions that predispose a mammal, especially a human to the disorder. Examples of non-limiting disorders to be treated herein include cancer, inflammation, autoimmune diseases, infections, cardiovascular diseases, respiratory diseases, neurological diseases, and metabolic diseases.

The antibodies of the present invention can be used to treat, inhibit or prevent diseases such as allergic diseases, Th2-mediated diseases, IL-13 mediated diseases, IL-4 mediated diseases and/or IL-4/IL-13-mediated diseases. Examples of such diseases include Hodgkin's disease, asthma, allergic asthma, atopic dermatitis, atopic allergy, ulcerative colitis, scleroderma, allergic rhinitis, COPD3 idiopathic pulmonary fibrosis, chronic transplant rejection, bleomycin-induced pulmonary fibrosis, radiation-induced pulmonary fibrosis, pulmonary granuloma, progressive systemic sclerosis, schistosomiasis, liver fibrosis, kidney cancer, Burkitt's lymphoma, Hodgkin disease, non-Hodgkin disease, Sezary syndrome, asthma, septic arthritis, herpes-like dermatitis, chronic idiopathic urticaria, ulcerative colitis, scleroderma, hypertrophic scar, Whipple's disease, benign prostatic hyperplasia, a pulmonary disorder in which the IL-4 receptor acts, a condition in which the IL-4 receptor mediates epithelial barrier disruption, a disorder of digestive system in which the IL-4 receptor acts, allergic responses to drugs, Kawasaki disease, sickle cell disease, Churg-Strauss syndrome, Grave's disease, preeclampsia, Sjogren's syndrome, autoimmune lymphoproliferative syndrome, autoimmune hemolytic Anemia, Barrett's esophagus, autoimmune uveitis, tuberculosis, cystic fibrosis, allergic bronchopulmonary fungal disease, chronic obstructive pulmonary disease, bleomycin-induced lung disease and fibrosis, pulmonary alveolar proteinosis, adult respiratory distress syndrome, sarcoidosis, hyper IgE syndrome, idiopathic hypereosinophil syndrome, autoimmune blistering disease, pemphigus vulgaris, bullous pemphigoid, myasthenia gravis, chronic fatigue syndrome and kidney disease.

The term "allergic disease" refers to a pathological condition in which a patient is hypersensitive and has an immune response to a substance that is normally non-immunogenic. A general characteristic of allergic diseases is that IgE activates mast cells and causes inflammatory responses (e.g., local responses, systemic responses), wherein these responses may lead to benign symptoms such as runny nose, and may also lead to life-threatening anaphylactic shock and death. Examples of allergic diseases include, but not limited to, allergic rhinitis (e.g., pollinosis), asthma (e.g., allergic asthma), allergic dermatitis (e.g., eczema), contact dermatitis, food allergy, and urticaria (hive).

As used herein, "Th2 mediated disease" refers to a disease, the pathology of which is (in whole or in part) caused by an immune response (Th2 type immune response) regulated by CD4+Th2T lymphoid cells, and which is characterized by the formation of IL-4, IL-5, IL-9 and IL-13. Th2-type immune responses are associated with the production of certain cytokines (e.g., IL-4, IL-13) and certain classes of antibodies (e.g., IgE), and humoral immunity. Th2-mediated diseases are characterized by the presence of elevated levels of Th2 cytokines (e.g., IL-4, IL-13) and/or certain classes of antibodies (e.g., IgE), and include, for example, allergic diseases (e.g., allergic rhinitis, idiopathic dermatitis, asthma (such as idiopathic asthma), allergic airway disease (AAD), anaphylactic shock and conjunctivitis), autoimmune disorders associated with elevated levels of IL-4 and/or IL-13 (e.g., rheumatoid arthritis, host-vs-graft disease, kidney disease (e.g., nephrotic syndrome, lupus nephritis)), and infections associated with elevated levels of IL-4 and/or IL-13 (e.g., viruses, parasites, fungi (such as $C.$ $albicans$) infection). Some cancers are associated with elevated levels of IL-4 and/or IL-13, or with IL-4-induced and/or IL-13-induced cancer cell proliferation (e.g., B-cell lymphoma, T-cell lymphoma, multiple myeloma, head and neck cancer, breast cancer and ovarian cancer). These cancers can be treated, inhibited or prevented with the Ii gaud of the present invention.

The term "cancer" as used in the present invention refers to or describes the physiological condition of a mammal, especially human, which is typically characterized by the uncontrolled and unregulated growth of cells. Examples of cancer include, but not limited to, carcinoma, lymphoma, blastoma, sarcoma, and leukemia.

The term "autoimmune disease(s)" as used herein refers to a non-malignant disease or disorder arising from and directed against an individual's own tissues. Examples of autoimmune diseases or disorders include, but not limited to, inflammatory responses such as inflammatory dermatosis, including psoriasis and dermatitis; allergic conditions such as eczema and asthma; other symptoms involving T cell infiltration and chronic inflammatory responses; atherosclerosis, diabetes mellitus (e.g., diabetes mellitus type I or insulin-dependent diabetes mellitus); multiple sclerosis and central nervous system inflammatory disorders.

The antibodies of the present invention may be used as compositions for administration alone or may be used in combination with other active agents. The antibodies can be used in a combination therapy with existing IL-13 therapies (e.g., existing IL-13 active agents such as anti-IL-13Rα1, IL-4/13Trap, anti-IL-13) plus anti-IL-4 antibodies, as well as existing IL-4 active agents (e.g., anti-IL-4R, IL-4 mutant protein, IL-4/13Trap) plus anti-IL-13 antibody and IL-4 antibody (e.g., WO 05/0076990 (CAT), WO 03/092610 (Regeneron), WO 00/64944 (Genetic Inst.) and WO 2005/062967 (Tanox)).

A nucleic acid encoding the antibody or functional fragment thereof of any of the preceding aspects.

A vector comprising the nucleic acid of any of the preceding aspects.

A cell comprising the vector of any of the preceding aspects.

A pharmaceutical composition comprising the antibody or functional fragment thereof, or the nucleic acid encoding same of any of the preceding aspects, and a pharmaceutically acceptable carrier.

A method for treating allergic diseases in a mammal, comprising the step of administering to the mammal a therapeutically effective amount of the antibody or functional fragment thereof, or the nucleic acid encoding same of any of the preceding aspects.

A method for treating allergic diseases in a mammal, comprising the step of administering to the mammal a therapeutically effective amount of the antibody or functional fragment thereof, or the nucleic acid encoding same of any of the preceding aspects.

A method for treating cancers, comprising the step of administering to the mammal a therapeutically effective amount of the antibody or functional fragment thereof, or the nucleic acid encoding same of any of the preceding aspects.

A method for treating asthma in a mammal, comprising the step of administering to the mammal a therapeutically effective amount of the antibody or functional fragment thereof, or the nucleic acid encoding same of any of the preceding aspects.

A method for treating diseases associated with abnormal production of IL-4 and/or IL-13 in a mammal, comprising the step of administering to the mammal a therapeutically effective amount of the antibody or functional fragment thereof, or the nucleic acid encoding same of any of the preceding aspects.

A method for inhibiting a TH-2 mediated response in a mammal, comprising the step of administering to the mammal a therapeutically effective amount of the antibody or functional fragment thereof, or the nucleic acid encoding same of any of the preceding aspects.

As used herein, the term "pharmaceutically acceptable carrier" is intended to include any and all solvents, dispersion media, coatings, antibacterial and antifungal agents, isotonic and absorption delaying agents, etc., which are compatible with pharmaceutical administration. Suitable carriers are described in the most recent edition of Remington's Pharmaceutical Sciences, a standard reference text in the field, which is incorporated herein by reference. Preferred examples of such carriers or diluents include, but not limited to, water, saline, Ringer's solutions, dextrose solution, and 5% human serum albumin. Liposomes and non-aqueous carriers such as fixed oils may also be used. The use of such media and agents with pharmaceutically active substances is well known in the art. Except insofar as any conventional media or agent is incompatible with the antibody, use thereof in the compositions is contemplated.

The formulations to be used for in vivo administration must be sterile. This is readily accomplished by filtration through sterile filtration membranes.

The pharmaceutical compositions of the embodiments are formulated to be compatible with their intended route of administration. Examples of routes of administration include parenteral, such as intravenous, intradermal, subcutaneous, oral (e.g., inhalation), transdermal (i.e., topical), transmucosal, and rectal administration. Solutions or suspensions used for parenteral, intradermal or subcutaneous administration may include the following components: sterile diluents for injection such as water, saline solution, fixed oil, polyethylene glycols, glycerol, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates and phosphates; and agents for the adjustment of osmotic pressure such as sodium chloride or dextrose. The pH can be adjusted with an acid or a base such as hydrochloric acid or sodium hydroxide. The parenteral formulation can be enclosed in ampoules, disposable syringes or multiple dose vials made of glass or plastic.

Pharmaceutical compositions suitable for injectable use include sterile aqueous solutions (water soluble herein) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It should be stable under the conditions of manufacture and storage and must be preserved against the contaminating action of microorganisms such as bacteria and fungi. The carrier may be a solvent or dispersion medium containing, for example, water, ethanol, polyol (e.g., glycerol, propylene glycol, liquid polyethylene glycol, etc.), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, etc. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody or antibodies in the required amount in an appropriate solvent with one or a combination of ingredients enumerated above, as required, followed by filtered sterilization. Generally, dispersions are prepared by incorporating the antibody or antibodies into a sterile carrier which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a sterile-filtered solution of the above ingredients.

For administration by inhalation, the compound is delivered in the form of an aerosol spray from a pressurized container or dispenser or nebulizer, which contains a suitable propellant such as carbon dioxide.

Systemic administration can also be performed by transmucosal or transdermal means. For transmucosal or transdermal administration, penetrants appropriate for barrier permeation are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, one or more of the antibodies can be formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the antibodies can be prepared with carriers that will protect the antibodies against rapid elimination from the body, such as a sustained release/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to a person skilled in the art.

For example, these active ingredients can be encapsulated in microcapsules prepared, for example, by coacervation techniques or by interfacial polymerization methods, for example hydroxymethylcellulose or gelatin microcapsules and poly(methylmethacrylate) microcapsules, respectively in colloidal drug delivery systems (e.g., liposomes, albumin microspheres, microemulsions, nanoparticles, and nanocapsules) or in macroemulsions.

A sustained release formulation can be prepared. Examples of suitable sustained release formulations include semipermeable matrices of solid hydrophobic polymers containing the antibodies, which matrices are in form of shaped articles, e.g., films, or microcapsules. Examples of sustained release matrices include polyesters, hydrogels (e.g., poly(2-hydroxyethyl-methylpropionate), or poly(vinyl alcohol)), polylactide (U.S. Pat. No. 3,773,919), copolymers of L-glutamic acid and γ ethyl-L-glutamate, non-degradable ethylene-vinyl acetate, degradable lactic acid-glycolic acid copolymers such as LUPRON DEPO™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Liposomal suspensions (including liposomes targeted to infected cells with monoclonal antibodies against viral antigens) can also be used as pharmaceutically acceptable carriers. These can be prepared according to methods known to a person skilled in the art, for example, methods described in U.S. Pat. No. 4,522,811.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of one or more of the antibodies calculated to produce the desired therapeutic effect in association with the required pharmaceutical carriers. The specifications for the dosage unit forms of the embodiments are dictated by and directly dependent on: the unique characteristics of the antibodies and the particular therapeutic effect to be achieved; and the limitations inherent in the art of formulating such antibodies for the treating individuals.

The pharmaceutical composition can be placed in a container, package, or dispenser together with instructions for administration.

The formulation herein may also contain more than one antibody as necessary for the particular indication being treated, preferably those with complementary activities that do not adversely affect each other. Alternatively, or in addition, the composition may comprise an agent that enhances its function, such as a cytotoxic agent, cytokine, chemotherapeutic agent, or growth-inhibitory agent. Such molecules are suitably present in combination in amounts that are effective for the purpose intended.

In one embodiment, one or more of the antibodies can be administered in a combination therapy, i.e., in combination with other agents, such as therapeutic agents (which can be used to treat pathological conditions or disorders, such as various forms of cancer, autoimmune disorders, and inflammatory disorders). The term "in combination with" as used herein refers to administrating agents substantially simultaneously, simultaneously or sequentially. If administered sequentially, the first compound of two compounds is still preferably detected at an effective concentration at the treatment site upon initiation of administration of the second compound.

For example, a combination therapy may comprise one or more antibodies described herein that are co-formulated and/or co-administered with one or more additional therapeutic agents (e.g., one or more cytokine and growth factor inhibitors, immunosuppressants, anti-inflammatory agents, metabolic inhibitors, enzyme inhibitors, and/or cytotoxin or cytostatic agents, as described in more detail below). Such combination therapies may advantageously utilize lower dosages of the administered therapeutic agents, thus avoiding possible toxicities or complications associated with the various monotherapies.

Preferred therapeutic agents for use in combination with the antibodies described herein are those that interfere with different stages of the inflammatory response. In one embodiment, one or more antibodies described herein can be co-formulated and/or co-administered with one or more additional agents such as other cytokines or growth factor antagonists (e.g., soluble receptors, peptide inhibitors, small molecules, ligand fusions); or antibodies or antigen-binding fragments which bind to other targets (e.g., antibodies which bind to other cytokines or growth factors, receptors thereof, or other cell surface molecules); and anti-inflammatory cytokines or agonists thereof.

In other embodiments, the antibodies described herein are used as vaccine adjuvants for autoimmune disorders, inflammatory diseases, etc. Combinations of adjuvants for treating these types of disorders are suitable for use in combination with various antigens, wherein the antigens are derived from the targeted autoantigens, i.e., autoantigens involved in autoimmunity, such as myelin basic protein; inflammatory autoantigens, such as amyloid peptide protein; or transplantation antigens, such as alloantigens. Antigens may include peptides or polypeptides derived from proteins and fragments of any of the following: sugars, proteins, polynucleotides or oligonucleotides, autoantigens, amyloid peptide proteins, transplantation antigens, allergens or other macromolecular components. In some examples, more than one antigen is comprised in an antigenic composition.

For the purpose of clarity and a concise description, features are described herein as part of the same or separate embodiments, however, it will be understood that the scope of the present invention may include some embodiments having combinations of all or some of the features described.

EMBODIMENTS

1. Recombinant Expression of the Protein of IL-4Rα Extracellular Region in Eukaryotic Cells A plasmid gene AgH01-pUC57-Amp (SynbioTech) containing a human IL-4Rα extracellular region (Uniprot P24394, 26-232) is synthesized. Using this plasmid as a template, 5'-ctgagaggtgccagatgtatgaaggtgctgcag-3' (SEQ ID NO: 231) as the upstream primer and 5'-tccgcctccgccgctagcgtgctgctcgaaggg-3' (SEQ ID NO: 232) as the downstream primer, the human IL-4Rα extracellular fragment is amplified by PCR. The amplified products are ligated using NEBuilder HiFi DNA Assembly Master Mix (NEB, Cat: M0530L) and cloned into an in house-constructed eukaryotic expression plasmid system (a fusion protein with a c-terminal 6×his tag). Similarly, the DNA sequence encoding a cynomolgus IL-4Rα extracellular region (Uniprot Q6JHZ9, 24-231) is cloned into the eukaryotic expression plasmid system using a synthetic plasmid AgC01-pUC57-Amp as a template. The gene encoding human IL-4 (Uniprot P05112, 25-153) is cloned into the eukaryotic expression plasmid system using a synthetic Ag1104-PUC57-Amp plasmid as a template. The gene encoding human IL13Rα1 (Uniprot P78552, 27-343) is cloned into the eukaryotic expression plasmid system using a purchased IL13Rα1 cDNA cloning plasmid (Sino Biological, Cat: HG10943-M) as a template. After transfecting HEK293-6E cells with these plasmids for 7 days, the culture supernatant is collected and purified by a nickel-chelate column to obtain recombinant proteins of human IL-4Rα extracellular region (hIL-4Rα), cynomolgus IL-4Rα extracellular region (cynoIL-4Rα), human IL-13Rα1 extracellular region (hIL-13Rα1) and human IL-4 (hIL-4).

Figure 1B:
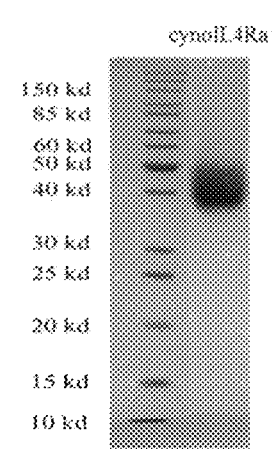
FIG. 1B shows that the protein of the extracellular region of cynomolgus monkey IL-4Rα has a size of approximately 40K Daltons.
Figure 1C:
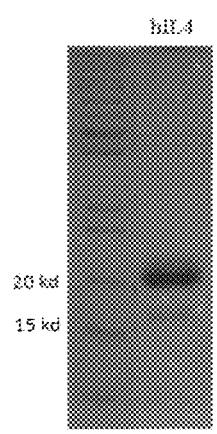
FIG. 1C shows that the human IL-4 protein has a size of approximately 20K Daltons.
Figure 1D:
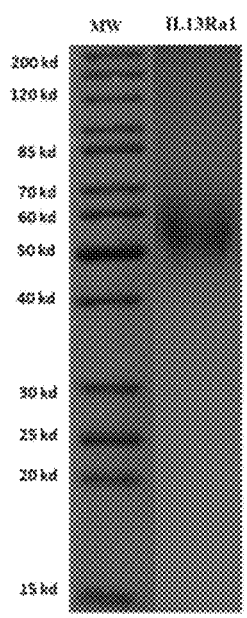
FIG. 1D shows that the protein of the extracellular region of human IL-13Rα1 has a size of approximately 55K Daltons.

The results are as shown in FIGS. 1A, 1B, IC and ID, showing that the size of the proteins of human and cynomolgus IL-4Rα extracellular regions is around 40K Daltons; the size of the protein of human IL-13Rα1 extracellular region is around 55K Daltons; and the size of the protein of human IL-4 is around 20K Daltons.

2. Obtaining Stably Transfected Cell Line of HEK293-hIL-4Rα

The expression plasmid containing the full-length sequence of hIL-4Rα is mixed with PEI at a ratio of 1:3 in Opti-MEM medium, and allowed to stand at room temperature for 20 minutes. The cells inoculated in a 6-well plate the day before are taken out, and the cell confluence is observed under a microscope to be about 80%. DMEM medium (Gibco) is aspirated and 4.5 ml of pre-warmed Opti-MEM medium (Gibco) is added. The plasmid-PEI mixture was then added dropwisely into the cells, gently shaken, and cultured in a carbon dioxide incubator at 37° C.; 24 hours later, an eukaryotic screening substance puromycin (Gibco) at a concentration of 1 ug/ml is added for screening culture. The cells grown in the screening medium are observed under a microscope, and subclones are obtained by screening via limited dilution. FACS analysis are performed after monoclonal cells are confluent in the wells.

Figure 2:
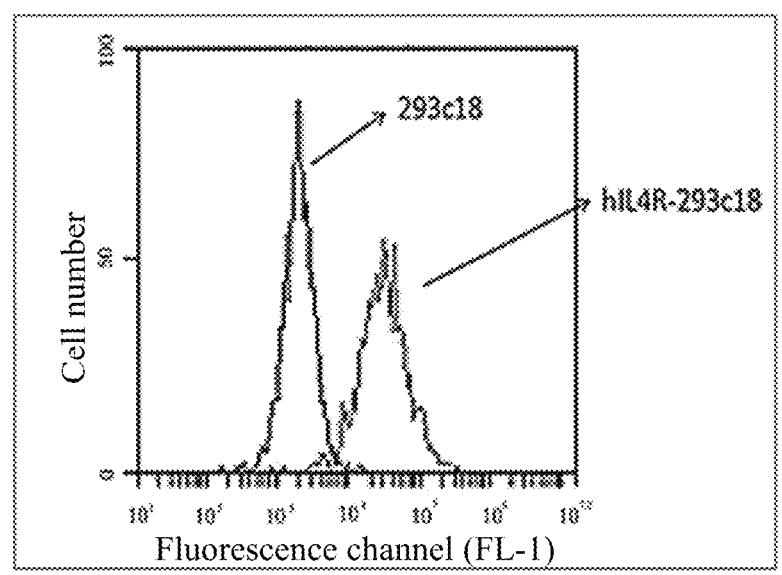
FIG. 2 shows the monoclonal HEK293 cells stably expressing hIL-4Rα.

The medium is aspirated, the cells are washed with PBS buffer, 200 ul of trypsin is added for digestion for a short time, and 700 ul of complete medium is added to terminate the digestion. 300 ul of the cell suspension is taken for staining, and the remaining cells are placed in an incubator at 37° C. to continue the culture. 500 ul of 0.5% BSA/PBS is added to the cells used for staining in each tube, and same is centrifuged at 200*g for 3 minutes, and washed twice. 2 ul of a control antibody (Sino Biological, Cat: 10402-R209) is added as a primary antibody to 800 ul of 1% BSA/PBS solution to a final concentration of 10 ug/ml; 100 ul of same is added to each tube, and incubated on ice and in the dark for 1 hour. Similarly, 500 ul of 0.5% BSA/PBS is added to each tube, centrifuged at 200*g for 3 minutes, and washed twice. A secondary antibody FITC-conjugated goat anti-rabbit IgG (BD Biosciences, Cat: 554020) is added at a dilution of 1:200, 100 ul of same is added to each tube, and incubated on ice for 1 hour in the dark. Similarly, 500 ul of 0.5% BSA/PBS is added to each tube, centrifuged at 200*g for 3 minutes, and washed three times. The cells are resuspended with addition of 300 ul of PBS solution and detected on a flow cytometer. The results are as shown in FIG. 2, showing that monoclonal HEK293 cells stably expressing hIL-4Rα are obtained.

3. Preparation of Anti-hIL-4Rα Antibody 3.1 Animal Immunization

The hIL-4Rα recombinant protein is mixed as an antigen with an equal amount of immunological adjuvant (Freund's adjuvant), and five 6-week-old female Balb/c mice are immunized by subcutaneous injection at abdominal region. After the prime immunization, a boost immunization is performed every two weeks. After four immunizations, blood is taken from the tail, and the titer of serum and the inhibition of binding to ligand hIL-4 of 5 mice are detected by ELISA, respectively.

Figure 3A:
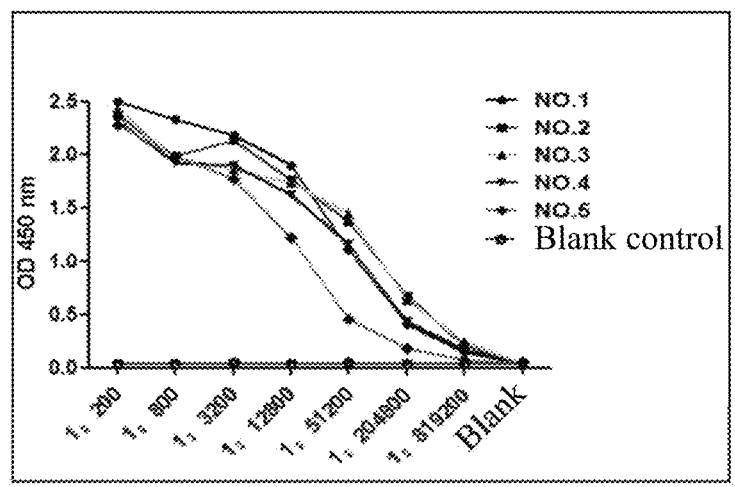
FIG. 3A shows that the titers of antibodies in the serum of 5 immunized mice can all reach 1: 819200.
Figure 3B:
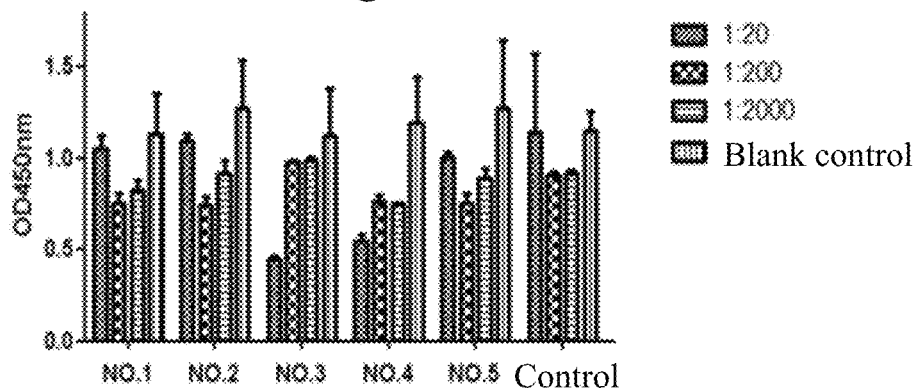
FIG. 3B shows that the antibodies in the serum of immunized mice #3 and #4 can inhibit the binding of human IL-4 and IL-4 receptors.

One 96-well ELISA plate (Thermo Maxisorp) is taken, and 100 μl of PBS (ZSGB-BIO, Item No. ZLI-9063) is added to each well, and incubated at room temperature for 10 min. 5 ul of 1 mg/ml IL-4Rα recombinant protein is taken out, added to 5 ml of 0.05 M carbonate coating buffer (pH 9.5), and mixed upside down to obtain 1 ug/ml antigen coating solution. The PBS solution in the wells of the plate is discarded, and 100 ul of the antigen coating solution is added to each well, and incubated at 4° C. overnight. The coating solution is discarded from the coated wells of the plate, which is then washed 3 times with PBS-T, and an additional 200 ul of 2% milk/PBS is added to each well and then blocked at room temperature for 2 hours; and the blocking solution is discarded, and the wells are washed three times with PBS for use. For serum titer experiments, serum samples from the 5 mice are diluted according to series of 1:200, 1:800, 1:3200, 1:12800, 1:51200, 1:204800, and 1:81200, and 100 ul of each diluent is added to the wells of the plate and incubated at 37° C. for 1.5 hours. The wells are washed three times with PBS-T and PBS, respectively, and spin-dried. The secondary antibody anti-mIgG Fc-HRP (Jackson, Cat: 115035071) is diluted at 1:4000 with 0.5% BSA, and 100 ul of same is added to each well, and incubated for 30 minutes at room temperature. For the serum blocking experiment, serum samples of the 5 mice are diluted at 1:20, 1:200, and 1:2000, and 50 ul of same is added to each well, and incubated for 30 minutes at room temperature. A 5 ml blocked EP tube is taken, the blocking solution is discarded, 3 ml of 0.5% BSA is added, and 1.1 ul of biotin-labeled human IL-4 is further added to a final concentration of 625 ng/ml; 50 ul of same is added to each well, and incubated at 37° C. for 1 hour. The wells are washed three times with PBS-T and PBS, respectively, and spin-dried. The secondary antibody SA-HRP (BD bioscience, Cat: 6222697) is diluted at 1:8000 with 0.5% BSA, and 100 ul of same is added to each well, and incubated for 30 minutes at room temperature. The wells are washed three times with PBS-T and PBS, respectively, and spin-dried. 100 ul of TMB (Sigma, Cat: T2885) substrate solution is added to each well, and the reaction is carried out at 37° C. in the dark; the substrate is moderately colored, 50 ul of $H_2SO_4$ is then added to each well to terminate the reaction, and the OD 450 nm is measured using a microplate reader (BioTek, Synergy HT) within 15 minutes; and data is collected and the results are calculated using Graph Pad Prism 5 software. The results are as shown in FIG. 3A, showing that the antibody titer in the serum of the 5 immunized mice can reach 1:819200. The results are as shown in FIG. 3B, showing antibodies in the serum of #3 and #4 immunized mice can inhibit the binding of human IL-4 to the IL-4 receptor.

3.2 Preparation of Antibody Phage Display Library

Three days after the tail vein challenging, the #3 and #4 immunized mice as stated above are sacrificed by cervical dislocation, and the spleen and peripheral lymph nodes of the mice are collected; after milling same in PBS buffer, a B cell-rich suspension is taken and B cells are collected by centrifugation. Total RNA is extracted from B cells using a Trizol RNA extraction kit, and an antibody heavy chain cDNA library is obtained by reverse transcription using a heavy chain-specific primer with a reverse transcription kit (SuperScript™ First-Strand Synthesis System, Cat: 18080051). Using the cDNA as a template, an antibody heavy chain variable region fragment is amplified by PCR using a set of heavy chain variable region primers; after double digestion with NcoI and NheI, the amplified antibody heavy chain variable region fragment is cloned into a in house-constructed phagemid pDS-mHC. Similarly, a light chain cDNA library is obtained by reverse transcription using a light chain-specific primer. Using the cDNA as a template, an antibody light chain variable region fragment is amplified by PCR using a set of light chain variable region primers; after double digestion with NcoI and Bsiw3.I, the antibody light chain variable region fragment is cloned into a in house-constructed phagemid pDS-LC. A mouse Fab phage display library based on filamentous phage M13 is then constructed with a library capacity of $6\times10^9$.

3.3. ELISA Screening for Antibodies that Bind to hIL-4Rα

A Fab antibody with specificity against IL-4Rα is isolated from the phage display library using a routine biopanning of a series of recombinant human IL-4R proteins. Briefly, 25 ul of 1 mg/ml IL-4Rα recombinant protein is taken out, added to 5 ml of PBS (ZSGB-BIO, Item No. ZLI-9063) coating solution, and mixed upside down to obtain 5 ug/ml antigen coating solution. IL-4Rα formulated in 0.05 M carbonate coating buffer (pH 9.5) is coated onto an immunotube (Immunotube Maxisorp, Nunc) at 4° C. overnight. The immunotube is washed with PBS and then blocked with 5% BSA for 2 hours. Purified Fan phage prepared with BSA at a final concentration of 1% is added to the immunotube and allowed to bind to the coated antigen for 1 hour. Multiple rounds of washing are performed with PBS-Tween (0.5% v/v) and PBS to remove unbound phage, and the bound phage particles are eluted with 100 mM triethylamine; after being neutralized with 1 M Tris-HCl (pH 7.4), the eluted phage particles are infected into *E. coli* TG1 bacteria and rescued for the next round of enrichment screening. After the two rounds of biopanning, single colonies are picked to 96-well U-type plates for IPTG-induced expression, and the supernatant is taken for ELISA screening.

10 ul of 1 mg/ml hIL-4Rα solution is taken out, added to 10 ml of 0.05 M carbonate coating buffer (pH 9.5), and mixed upside down to obtain 1 ug/ml antigen coating solution. The prepared antigen coating solution is added to a 96-well ELISA plate (Thermo Maxisorp) with 100 ul per well. The 96-well ELISA plate is wrapped with a sealing membrane and incubated overnight at 4° C. The next day, the ELISA plate is taken out, placed on a plate washer (BioTek, Synergy HT), and washed three times with PBS; PBS solution containing 2% BSA is added with 200 ul per well, and blocked at room temperature for 2 hours. The blocking solution is then discarded and the plate is washed three times with PBS. The induced supernatant is sequentially added to the corresponding wells with 50 ul per well, the wells are incubated for 1 hour at room temperature, the supernatant is discarded, and the wells are washed 3 times with PBS-T and PBS, respectively. TMB solution (Sigma, Cat No: T2885) is added to the 96-well ELISA plate row by row with 100 ul per well. After standing at 37° C. for 5 minutes, the reaction is immediately terminated by adding 50 ul of 2 M concentrated sulfuric acid solution to the 96-well ELISA plate. The 96-well ELISA plate is placed in a microplate reader (BioTek, Synergy HT), the OD450 value is read, and the data is collected and the results were calculated using GraphPad Prism 5 software. A total of 3100 single colonies are picked for IPTG induction, and 576 of them are detected by ELISA to bind to hIL-4Rα antigen.

3.3. ELISA Screening for Antibodies that Inhibit the Interaction Between Human IL-4 and hIL-4Rα

The 576 positive single colonies bound to hIL-4Rα antigen are re-induced by IPTG, and the supernatant is taken for screening by ELISA. Seven 96-well ELISA plates (Thermo Maxisorp) are taken, and 100 μl of PBS (ZSGB-BIO, Item No. ZLI-9063) is added to each well, and incubated at room temperature for 10 min. 35 ul of 1 mg/ml IL-4Rα recombinant protein is taken out, added to 35 ml of 0.05 M carbonate coating buffer (pH 9.5), and mixed upside down to obtain 1 ug/ml antigen coating solution. The PBS solution in the wells of the plate is discarded, and 100 ul of the antigen coating solution is added to each well, and incubated at 4° C. overnight. The coating solution is discarded from the coated wells of the plate, which is then washed three times with PBS-T, and an additional 200 ul of 2% milk/PBS is added to each well and then blocked at room temperature for 2 hours; and the blocking solution is discarded, and the wells are washed three times with PBS. 50 ul of antibody is pipetted from each well to induce supernatant, added to the ELISA plate with 50 ul per well, and incubated at room temperature for 30 minutes. A 5 ml blocked EP tube is taken, the blocking solution is discarded, 3 ml of 0.5% BSA is added, and 1.1 ul of biotin-labeled IL-4 is further added to a final concentration of 625 ng/ml; 50 ul of same is added to each well, and incubated at 37° C. for 1 hour. The wells are washed three times with PBS-T and PBS, respectively, and spin-dried. The secondary antibody SA-HRP (BD bioscience, Cat: 6222697) is diluted at a ratio of 1:8000 with 0.5% BSA, and 100 ul of same is added to each well, and incubated for 30 minutes at room temperature. The wells are washed three times with PBS-T and PBS, respectively, and spin-dried. 100 ul of TMB substrate solution is added to each well, and the reaction is carried out at 37° C. in the dark, the substrate is moderately colored, 50 ul of $H_2SO_4$ is then added to each well to terminate the reaction, and the OD 450 nm is measured using a enzyme-linked detector (BioTek, Synergy HT) within 15 minutes, and data is collected and the results are calculated using Graph Pad Prism 5 software. Among the positive colonies obtained in 3.2 ELISA, 120 single colonies inhibit the binding of human IL-4 to hIL-4Rα.

Figure 3C:
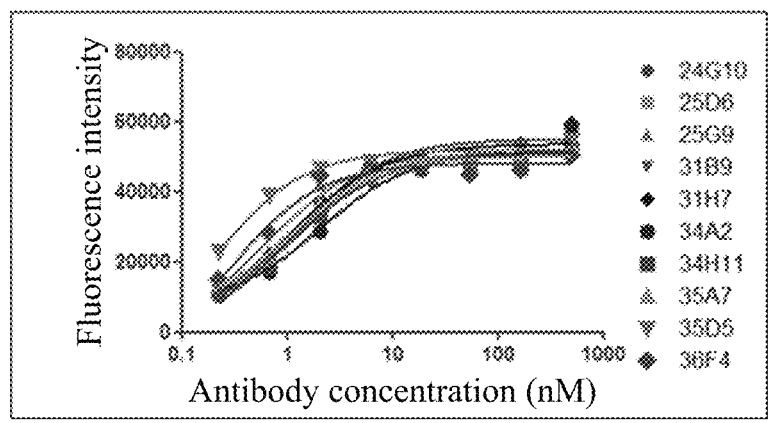
FIG. 3C shows that the antibodies pre-screened by ELISA all specifically bind to stably-transfected HEK293 cells expressing IL-4Rα.

3.4. FACS Analysis for Antibodies that Bind to hIL-4Rα Expressed on the Surface of Cell Membranes The supernatant of the above detected 120 positive single colonies which inhibit the binding of human IL-4 to human hIL-4Rα is taken for FACS analysis. HEK293 cells and stably transfected cell line of HEK293-hIL-4Rα are prepared with $5*10^4$ cells per well, and the amount of Cell Tracker Green CMFDA (Invitrogen, Cat: C2925) for cells staining is 100 μl of cell tracker green solution per $1*10^6$ cells, and incubation is performed for 30 minutes in an incubator at 37° C.; 5 ml of 0.5% BSA/PBS is added, and same is centrifuged at 1000 rpm for 3 minutes, and washed 3 times. Every $1*10^6$ cells corresponds to 100 μl of 3% BSA/PBS solution, and the solution is blocked at 4° C. for 20 minutes; the prepared cells are added to a 96-well U-type plate at a volume of 100 μl/well, and centrifuged at 1100 rpm for 3 minutes, and the supernatant is discarded; and the primary antibody solution is added and incubated for 1 hour on ice. Purified Fab antibodies are made into a 5-concentration series with a starting concentration of 500 nM (12.5 μg/ml), and diluted according to a series of 1: 5. After incubation with the primary antibody solution, additional 0.5% BSA/PBS is added to a volume of 150 μl, centrifuged at 1100 rpm for 3 minutes, and the supernatant is discarded; 150 μl of 0.5% BSA/PBS is further added, centrifuged at 1100 rpm for 3 minutes, and the supernatant is discarded; before adding a secondary antibody anti-human IgG, Fab'2-AF647 (Jackson), same is diluted at 1:300 with 1% BSA/PBS; 40 μl of the diluted secondary antibody solution is added to each well and incubated on ice for 45 minutes. After incubation with the secondary antibody solution, additional 0.5% BSA/PBS is added to a volume of 150 μl, centrifuged at 1100 rpm for 3 minutes, and the supernatant is discarded; 150 μl of 0.5% BSA/PBS is further added, centrifuged at 1100 rpm for 3 minutes, and the supernatant is discarded; 20-100 μl of PBS is added to resuspend the cells to $1*10^6$ cells per ml, and the obtained suspension is loaded onto a flow cytometer (I-Que screener). After opening the instrument and operating system according to the correct process, and setting the correct parameters, the cells are loaded to the test plate, and the fluorescent signal is detected; analysis is performed using Graph Pad Prism 5 software, and the results are as shown in FIG. 3C, showing that the antibodies screened by the pre-ELISA are specifically bound to HEK293 stably transfected cells expressing IL-4Rα.

3.5. FACS Analysis for Antibodies that Inhibit the Interaction Between Human IL-4 and hIL-4Rα

Figure 3D:
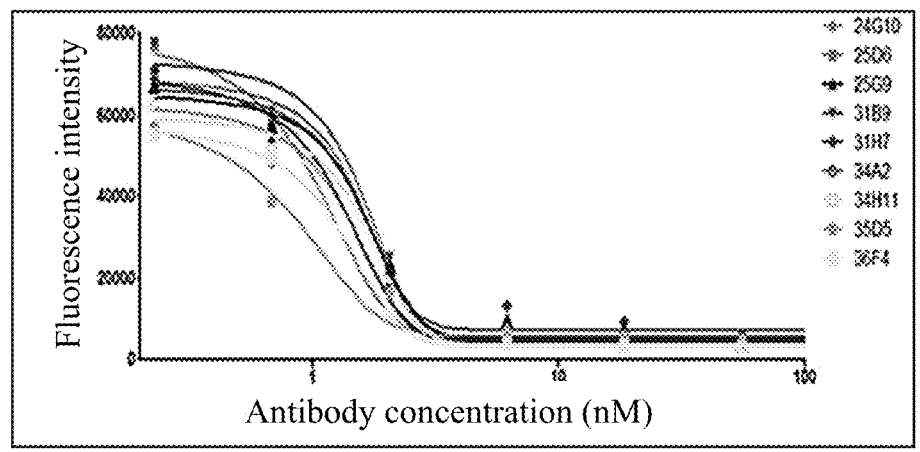
FIG. 3D shows 15 antibodies in the positive colonies pre-screened by ELISA can inhibit the binding of stably-transfected cells expressing hIL-4Rα to human IL-4.

The supernatant of the FACS analyzed first 100 positive single colonies with strong binding to hIL-4Rα is taken for inhibiting experiments of receptors expressed on cell surface. HEK293 cells and HEK293-hIL-4Rα stably transfected cells are prepared with 3*10⁴ cells per well, and the amount of Cell Tracker™ Green CMFDA (Invitrogen, Cat: C2925) for cells staining is 100 µl of cell tracker green solution per 1*10⁶ cells, and incubation is performed for 30 minutes in an incubator at 37° C.; additional 5 ml of 0.5% BSA/PBS is then added, and same is centrifuged at 1000 rpm for 3 minutes, and washed 3 times. Every 1*10⁶ cells corresponds to 100 µl of 3% BSA/PBS solution, and the solution is blocked at 4° C. for 20 minutes. The prepared cells are added to a 96-well U-type plate at a volume of 100 µl/well, and centrifuged at 1100 rpm for 3 minutes, and the supernatant is discarded; and the primary antibody solution is added and incubated for 1 hour on ice. Purified Fab antibodies are made into a 5-concentration series with a starting concentration of 100 nM, and diluted according to a series of 1:5. After incubation with the primary antibody solution, additional 0.5% BSA/PBS is added to a volume of 150 µl, centrifuged at 1100 rpm for 3 minutes, and the supernatant is discarded; 150 µl of 0.5% BSA/PBS is further added, centrifuged at 1100 rpm for 3 minutes, and the supernatant is discarded; biotin-labeled human IL-4-mIgG2a Fc at a final concentration of 0.15 ug/ml is added and incubated on ice for 45 minutes. The secondary antibody SA-PE is diluted at 1:300 with 1% BSA/PBS; 40 µl of the secondary antibody solution is added to each well and incubated on ice for 45 minutes. After incubation with the secondary antibody solution, additional 0.5% BSA/PBS is added to a volume of 150 µl, centrifuged at 1100 rpm for 3 minutes, and the supernatant is discarded; 150 µl of 0.5% BSA/PBS is further added, centrifuged at 1100 rpm for 3 minutes, and the supernatant is discarded; 20-100 µl of PBS is added to resuspend the cells to 1*10⁶ cells per ml, and the obtained suspension is loaded onto a flow cytometer (I-Que screener). After opening the instrument and operating system according to the correct process, and setting the correct parameters, the cells are loaded to the test plate, and the fluorescent signal is detected; analysis is performed using Graph Pad Prism 5 software. The results are as shown in FIG. 3D, showing that 15 antibodies out of the positive single colonies screened by the pre-ELISA can inhibit the binding of stably transfected cells expressing hIL-4Rα to human IL-4.

4. Screening for Fab Antibodies that Inhibit the Binding of hIL-4Rα to the Complex hIL-13Rα/hIL-13 by Fortebio 4.1 Detection of the Binding of hIL-4Rα to the Complex hIL-13Rα/hIL-13

Figure 4A:
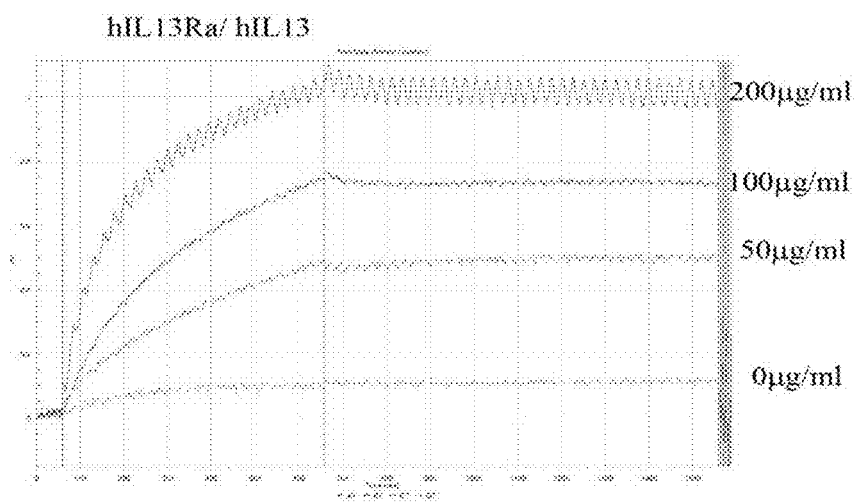
FIG. 4A shows that hIL-4Rα can bind to the complex hIL-13Rα/hIL-13.

1 ml of hIL-13Rα (at a concentration of 400 ng/ml) and 1 ml of hIL-13 (Sino Biological, Item No. 10369-HNAC, at a concentration of 400 ng/ml) are taken, and mixed at a ratio of 1:1 to a working concentration of 200 ng/ml, and is allowed to stand, incubate, and bind at room temperature for 2 hours. The hIL-13Rα/hIL-13 complex has an initial concentration of 200 ng/ml and is diluted according to a series of 1:1; three concentration series are set: 200 ng/ml, 100 ng/ml, and 50 ng/ml, with 100 ul per well in the 96-well plate, and blank control groups are set. Firstly, the biotin-labeled hIL-4Rα is immobilized by and bound to SA probe (at a working concentration of 10 ng/ml), 100 ul of same is added to each well, and the binding to hIL-13Rα/hIL-13 is detected by Fortebio; an experimental method is edited to run, and the experimental results are analyzed in Fortebio software. The results are as shown in FIG. 4A, showing that hIL-4Rα can bind to the complex hIL-13Rα/hIL-13.

4.2 Detection of Antibodies that Inhibit the Binding of hIL-4Rα to the Complex hIL-13Rα/hIL-13

Figure 4B:
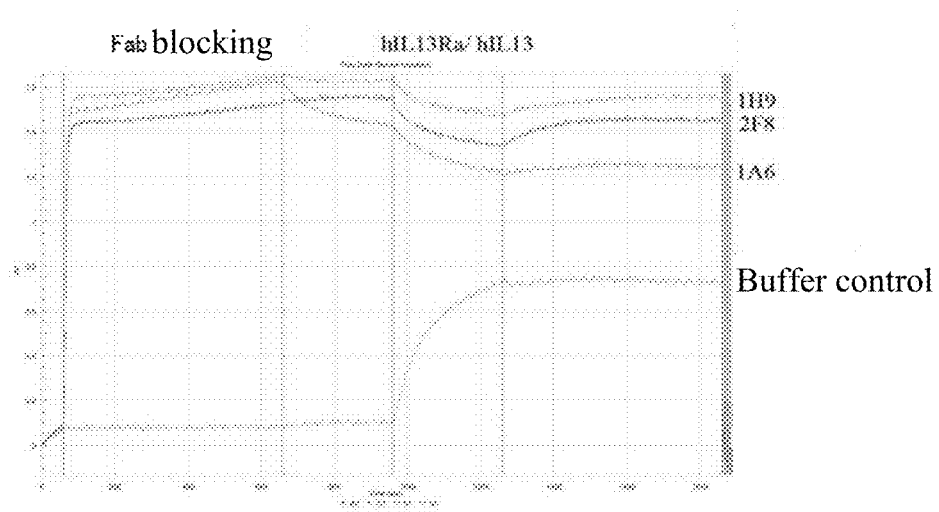
FIG. 4B shows that the candidate antibody can inhibit the binding of hIL-4Rα to the complex hIL-13Rα/hIL-13.

The above experiments demonstrate that hIL-4Rα can bind to the complex hIL-13Rα/hIL-13, and on this basis, Fab antibodies that inhibit the binding of hIL-4Rα to the complex hIL-13Rα/hIL-13 are further screened, the inhibitory effect of the candidate Fab antibodies screened in the previous period is compared, and the working buffer is set as the negative control group. The biotin-labeled hIL-4Rα is immobilized by a probe (at a concentration of 10 ng/ml), and the working concentrations of the candidate Fab antibodies are adjusted to 100 ug/ml, and the concentration of the complex hIL-13Rα/hIL-13 is 200 ng/ml; firstly, the biotin-labeled hIL-4Rα is immobilized by SA probe (at a working concentration of 10 ng/ml), 100 ul of same is added to each well, and the inhibiting effect of candidate Fab antibodies on hIL-4Rα and complex hIL-13Rα/hIL-13 is detected by Fortebio; an experimental method is edited to run, and the experimental results are analyzed in Fortebio software. The results are as shown in FIG. 4B, showing that the candidate antibodies can inhibit the binding of hIL-4Rα to the complex hIL-13Rα/hIL-13.

5. Variable Region Sequence of the Candidate Positive Monoclonal Antibody

The positive monoclonal plasmids are extracted and sequenced to obtain the sequences of the heavy chain and light chain variable regions of the candidate positive colonies: Clone 1A6:

(SEQ ID NO: 1-4)

```
Heavy chain
<-------------FR1------------>  CDR1<----FR2---->      CDR2      <----
QVQLQQSGTELVKPGASVKMSCKASVNTFTGYNMHWIKQTPGQGLEWIGGLHPGNGDSSYNQKFKGRATLT --------FR3--------------->    CDR3  <----FR3---->
ADKSSNTAYMQLSSLTSEDSAVYYCALTTAGRAWFPYWGQGTLVTVSA
```

(SEQ ID NO: 5)

```
Nucleic acid sequence
CAGGTTCAGCTGCAGCAGTCTGGGACTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA
```

Light chain (SEQ ID NO: 6-9)
```
<----------FR1-------->    CDR1      <-----FR2-----> CDR2   <---------------
DIQMTQTTSSLSASLGDRVTISCRASQDISNYLNWYQQKPDGTVKLLIYYTSRLHSGVPSRFSGSGSGTDY FR3------------->    CDR3 <---PR3--->
SLTISNLEQEDIATYFCQQGNTLPPTFGGGTKLEIK
```

(SEQ ID NO: 10)
Nucleic acid sequence
```
GATATCCAGATGACACAGACTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCCTCCGACGTTCGGTGGAGGCACCAAGCTGGAAATCAAA
```

(SEQ ID NO: 11-14)
Heavy chain
```
<-------------FR1------------->  CDR1<----FR2----->      CDR2       <----
QVQLQQSGTELVKPGASVKMSCKASVNTFTGYNMHWIKQTPGQGLEWIGGLHPGNGDSSYNQKFKGRATLT --------FR3--------------->   CDR3 <----PR3---->
ADKSSNTAYMQLSSLTSEDSAVYYCALTTAGRAWFAYWGQGTLVTVSA
```

(SEQ ID NO: 15)
Nucleic acid sequence
```
CAGGTTCAGCTGCAGCAGTCTGGGACTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA
```

(SEQ ID NO: 16-19)
Light chain
```
<----------FR1-------->    CDR1      <-----FR2-----> CDR2   <---------------
DIQMTQTTSSLSASLGDRVTISCRASQDISNYLNWYQQKPDGTVKLLIYYTSRLHSGVPSRFSGSGSGTDY FR3------------->    CDR3 <---PR3--->
SLTISNLEQEDIATYFCQQGNTLHTFGGGTKLEIK
```

(SEQ ID NO: 20)
Nucleic acid sequence
```
GATATCCAGATGACACAGACTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCACACGTTCGGAGGGGGGACCAAGCTGGAAATCAAA
``` clone 1H9:

(SEQ ID NO: 21-24)
Heavy chain
```
<-------------FR1------------->  CDR1<----FR2----->      CDR2       <----
QVQLQQSGAELVKPGASVKMSCKASVNTFAGYNMHWVKQTPGQGLEWIGGLHPGNGDTSYNQKFKGKATLT --------FR3--------------->   CDR3 <----PR3---->
ADKSSNTAYMQLSSLTSEDSAVYYCALTTAGRAWFAYWGQGTLVTVSA
```

(SEQ ID NO: 25)
Nucleic and sequence
```
CAGGTCCAGCTGCAGCAGTCTGGGGCTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA
```

(SEQ ID NO: 26-29)
Light chain
```
<----------FR1-------->    CDR1      <-----FR2-----> CDR2   <---------------
DIQMIQSTSSLSASLGDRVTISCRASQDISNYLNWYQQKPDGTVKLLIYYTSRLHSGVPSRFSGSGSGTDY FR3------------->    CDR3 <---PR3--->
SLTISNLEQEDIATYFCQQGNTLPWTFGGGTKLEIK
```

```
                                                     (SEQ ID NO: 30)
Nucleic acid sequence
GACATCCAGATGATTCAGACTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCACACGTTCGGAGGGGGGACCAAGCTGGAAATCAAA Clone 2H1:
                                                     (SEQ ID NO: 31-34)
Heavy chain
<-------------FR1-------------> CDR1<----FR2-----> CDR2     <----
QVQLQQSGAELVKPGASVKMSCKASVNTFTGYNMHWVKQTPGQGLEWIGGLHPGNGDTSYNQKFKGKATLT --------FR3----------------> CDR3 <----PR3---->
ADKSSNTAYMQLSSLTSEDSAVYYCALTTAGRAWFAYWGQGTLVTVSA (SEQ ID NO: 35)
Nucleic acid sequence
CAGGTTCAGCTGCAGCAGTCTGGGGCTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA (SEQ ID NO: 36-39)
Light chain
<----------FR1--------->   CDR1   <-----FR2-----> CDR2 <---------------
DIQMIQSTSSLSASLGDRVTISCRASQDISNYLNWYQQKPDGTVKLLIYYTSRLHSGVPSRFSGSGSGTDY

FR3-------------->  CDR3 <---PR3--->
SLTISNLEQEDIATYFCQQGNTLPLTFGAGTKLELK (SEQ ID NO: 40)
Nucleic acid sequence
GACATCCAGATGATTCAGACTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCCGCTCACGTTCGGTGCTGGGACCAAGCTGGAGCTGAAA Clone 2F8:
                                                     (SEQ ID NO: 41-44)
Heavy chain
<-------------FR1-------------> CDR1<----FR2-----> CDR2     <----
QVQLQQSGAELVKPGASVKMSCKASVNTFTGYNMHWVKQTPGQGLEWIGGLHPGNGDTSYNQKFKGKATLT --------FR3----------------> CDR3 <----PR3---->
ADKSSNTAYMQLSSLTSEDSAVYYCALTTAGRAWFPYWGQGTLVTVSA (SEQ ID NO: 45)
Nucleic acid sequence
CAGGTTCAGCTGCAGCAGTCTGGGGCTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA (SEQ ID NI: 46-49)
<----------FR1--------->   CDR1   <-----FR2-----> CDR2 <---------------
DIQMIQSTSSLSASLGDRVTISCRASQDISNYLNWYQQKPDGTVKLLIYYTSRLHSGVPSRFSGSGSGTDY

FR3-------------->  CDR3 <---PR3--->
SLTISNLEQEDIATYFCQQGNTLPWTFGGGTKLELK (SEQ ID NO: 50)
Nucleic acid sequence
GACATCCAGATGACCCAGTCTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCCGCTCACGTTCGGTGCTGGGACCAAGCTGGAAATCAA
```

-continued

Clone 9B4:

(SEQ ID NO: 51-54)
Heavy chain
```
         <-------------FR1------------->  CDR1<----FR2----->      CDR2       <----
QVQLQQSGAELVKPGASVKMSCKASVNTFTGYNMHWIKQTPGQGLEWIGGLHPGNGDTSYNQKFKGKATLT --------FR3---------------->    CDR3  <----FR3---->
ADKSSNTAYMQLSSLTSEDSAVYYCALTTAGRAWFAYWGQGTLVTVSA
```

(SEQ ID NO: 55)
Nucleic acid sequence
CAGGTCCAGCTGCAGCAGTCTGGGGCTGAGCTGGTGAAGCCTGGGGCCTCAGTGAAGATGTCCTG
CAAGGCTTCTGTCAACACATTTACCGGTTACAATATGCACTGGATAAAACAGACACCTGGACAGG
GCCTGGAATGGATTGGAGGTCTTCATCCAGGAAATGGTGATTCTTCCTACAATCAGAAGTTCAAA
GGCAGGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTCCTTACT
GGGGCCAAGGGACTCTGGTCACTGTCTCTGCA (SEQ ID NO: 56-59)
Light chain
```
<----------FR1-------->    CDR1    <-----FR2-----> CDR2  <---------------
DIQMIQSTSSLSASLGDRVTISCRASQDISNYLNWYQQKPDGTVKLLIYYTSRLHSGVPSRFSGSGSGTDY FR3------------->    CDR3   <---PR3--->
SLTISNLEQEDIATYFCQQGNTLPWTFGGGTKLELK
```

(SEQ ID NO: 60)
Nucleic acid sequence
GATATCCAGATGACACAGTCTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCCGCTCACGTTCGGTGCTGGGACCAAGCTGGAAATCAA Clone 9E7:

(SEQ ID NO: 61-64)
Heavy chain
```
         <-------------FR1------------->  CDR1<----FR2----->      CDR2       <----
EVQLQQSGAELVKPGASVKMSCKASVNIFTGYNMHWVKQTPGQGLEWIGGLHPGNGDTSYNQKFKDKATLT --------FR3---------------->    CDR3  <----FR3---->
ADKSSNTAYMQLSSLTSEDSAVYYCALTTAGRAWFAYWGQGTLVTVSA
```

(SEQ ID NO: 65)
Nucleic acid sequence
GAGGTTCAACTGCAGCAGTCTGGGGCTGAGCTGGTGAAGCCTGGGGCCTCAGTGAAGATGTCCTG
CAAGGCTTCTGTCAACATATTTACCGGTTACAATATGCACTGGGTAAAACAGACACCTGGACAGG
GCCTGGAATGGATTGGAGGTCTTCATCCAGGAAATGGTGATACTTCCTACAATCAGAAGTTCAAA
GACAAGGCCACATTGACTGCAGACAGATCCTCCAACACTGCCTACATGCAGCTTAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA (SEQ ID NO: 66-69)
Light chain
```
<----------FR1-------->    CDR1    <-----FR2-----> CDR2  <---------------
DIQMTQTTSSLSASLGDRVTISCRASQDISNYLNWYQQKPDGTVKLLIYYTSRLHSGVPSRFSGSGSGTDY FR3------------->    CDR3   <---PR3--->
SLTISNLEQEDIATYFCQQGNTLPWTFGGGTKLELK
```

(SEQ ID NO: 70)
Nucleic acid sequence
GATATCCAGATGACACAGTCTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAACTCCTGATCTACTACACATCAAGATTACACTCAGGAGTCCCATCAAGGTTCAGTGGCAGT
GGGTCTGGAACAGATTATTCTCTCACCATTAGCAACCTGGAGCAAGAAGATATTGCCACTTACTT
TTGCCAACAGGGTAATACGCTTCCGCTCACGTTCGGTGCTGGGACCAAGCTGGAAATCAA Clone 24G10:

(SEQ ID NO: 71-74)
Heavy chain
```
         <-------------FR1------------->  CDR1<----FR2----->      CDR2       <----
EVKLVESGGGLVKPGGSLKLSCAASGFTFSRYAMSWVRQTPEKRLEWVATISSGGSYTNYADSVKGRFTIS --------FR3---------------->    CDR3  <----FR3---->
RDNVKNTLYLQMNSLRAEDTAVYYCARATARATEFAYWGQGTLVTVSS
```

(SEQ ID NO: 75)
Nucleic acid sequence
GAGGTGAAGCTGGTGGAATCTGGGGGAGGCTTAGTGAAGCCTGGAGGGTCCCTGAAACTTTCCTG
TGCAGCCTCTGGATTCACTTTCAGTAGGTATGCCATGTCTTGGGTTCGCCAGACTCCGGAGAAGA
GGCTGGAGTGGGTCGCAACCATTAGTAGTGGTGGTAGTTATACCAACTATTCAGACAGTGTGAAG
GGGCGATTCACCATCTCCAGAGACAATGTCAAGAACACCCTGTATCTGCAAATGAGCAGTCTGAA
GTCTGAGGACTCGGCCATGTATTACTGTGCAAGGGCGACAGCTCGGGCTACAGAGTTTGCTTACT
GGGGCCAAGGGACTCTGGTCACTGTCTCTGCA (SEQ ID NO: 76-79)
Light chain
<----------FR1--------> CDR1    <-----FR2-----> CDR2  <---------------
DIQMTQTTSSLSASLGDRVTISCRASQDISNYLNWYQQKPDGTVKLLIYYTSRLHSGVPSRFSGSGSGTDY

FR3-------------> CDR3 <---PR3--->
SLTISNLEQEDIATYFCQQGNTLPPTFGGGTKLEL (SEQ ID NO: 80)
Nucleic acid sequence
GACATCCAGATGACACAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCTCCGACGTTCGGTGGAGGCACCAAGCTGGAAATCAA Clone 25D6:
(SEQ ID NO: 81-84)
Heavy chain
<-------------FR1-------------> CDR1<----FR2-----> CDR2      <----
EVQLQQSGAELVKPGASVKMSCKASVNIFTGYNMHWVKQTPGQGLEWIGGLHPGNGDTSYNQKFKDKATLT --------FR3----------------> CDR3 <----FR3---->
ADKSSNTAYMQLSSLTSEDSAVYYCALTTAGRAWFAYWGQGTLVTVSA (SEQ ID NO: 85)
Nucleic acid sequence
CAGGTCCAGCTGCAGCAGTCTGGGGCTGAACTGGTGAAGCCTGGGGCCTCAGTGAAGATGTCCTG
CAAGGCTTCTGTCAACACATTTACCGGTTACAATATGCACTGGGTAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCAG (SEQ ID NO: 86-89)
Light chain
<----------FR1--------> CDR1    <-----FR2-----> CDR2  <---------------
DIQMTQSTSSLSASLGDRVTISCRASQDISNYLNWYQQKPDGTVKLLIYYTSRLHSGVPSRFSGSGSGTDY

FR3-------------> CDR3 <---PR3--->
SLTISNLEQEDIATYFCQQGNTLPWTFGGGTKLEIK (SEQ ID NO: 90)
Nucleic acid sequence
GACATCCAGATGACCCAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCTCCGACGTTCGGTGGAGGCACCAAGCTGGAAATCAA Clone 25G9:
(SEQ ID NO: 91-94)
Heavy chain
<-------------FR1-------------> CDR1<----FR2-----> CDR2      <----
EVQLKESGAELVKPGASVKMSCKASVNIFTGYNMHWVKQTPGQGLEWIGGLHPGNGDTSYNQKFKDKATLT --------FR3----------------> CDR3 <----FR3---->
ADRSSNTAYMQLSSLTSEDSAVYYCALTTAGRAWFAYWGQGTLVTVSA (SEQ ID NO: 95)
Nucleic acid sequence
GAGGTGCAGCTGAAGGAGTCTGGGGCTGAGCTGGTGAAGCCTGGGGCCTCAGTGAAGATGTCCTG
CAAGGCTTCTGTCAACACATTTACCGGTTACAATATGCACTGGGTAAAACAGACACCTGGACAGG
GCCTGGAATGGATTGGAGGTCTTCATCCAGGAAATGGTGATACTTCCTACAATCAGAAGTTCAAA
GACAAGGCCACATTGACTGCAGACAGATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA -continued (SEQ ID NO: 96-99)
Light chain
<----------FR1--------> CDR1    <-----FR2-----> CDR2  <--------------
DIQMTQSTSSLSASLGDRVTISCRASQDISNYLNWYQQKPDGTVKLLIYYTSRLHSGVPSRFSGSGSGTDY

FR3-------------> CDR3 <---PR3--->
SLTISNLEQEDIATYFCQQGNTLPWTFGGGTKLEIK (SEQ ID NO: 100)
Nucleic acid sequence
GACATCCAGATGACTCAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA Clone 35A7:

(SEQ ID NO: 101-104)
Heavy chain
<-------------FR1-------------> CDR1<----FR2----->    CDR2     <----
QVQLKQSGAELVKPGASVKMSCTASVNIFTGYNMHWIKQTPGQGLEWIGGLHPGNGDTSYNQKFKDKATLT --------FR3----------------> CDR3 <----FR3---->
ADRSSNTAYMQLSSLTSEDSAVYYCALTTAGRAWFAYWGQGTLVTVSA (SEQ ID NO: 105)
Nucleic acid sequence
CAGGTCCAGCTGAAGCAGTCTGGGGCTGAGCTGGTGAAGCCTGGGGCCTCAGTGAAGATGTCCTG
CACGGCTTCAGGCAATATATTTAGTGGTTATAATATGCACTGGATAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACAGCCTACATGCAACTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA (SEQ ID NO: 106-109)
Light chain
<----------FR1--------> CDR1    <-----FR2-----> CDR2  <--------------
DIQMNQSTSSLSASLGDRVTISCRASQDISNYLNWYQQKPDGTIKLLIYYTSRLYSGVPSRFSGSGSGTDY

FR3-------------> CDR3 <---PR3--->
SLTISNLEEEDIATYFCQQGNTIPYTFGGGTKLEIK (SEQ ID NO: 110)
Nucleic acid sequence
GACATCCAGATGAACCAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA (SEQ ID NO: 111-114)
Heavy chain
<-------------FR1-------------> CDR1<----FR2----->    CDR2     <----
EVQLQQSGAELVKPGASVKMSCKASVNIFTGYNMHWVKQTPGQGLEWIGGLHPGNGDTSYNQKFKDKATLT --------FR3----------------> CDR3 <----FR3---->
ADRSSNTAYMQLSSLTSEDSAVYYCALTTAGRAWFAYWGQGTLVTVSA (SEQ ID NO: 115)
Light chain
<----------FR1--------> CDR1    <-----FR2-----> CDR2  <--------------
DIQMTQSTSSLSASLGDRVTISCRASQDISNYLNWYQQKPDGTIKLLIYYTSRLHSGVPSRFSGSGSGTDY

FR3-------------> CDR3 <---PR3--->
SLTISNLEEEDIATYFCQQGNTLPWTFGGGTKLEIK (SEQ ID NO: 120)
Nucleic acid sequence
GACATCCAGATGACACAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA Clone 34A2:

(SEQ ID NO: 121-124)
<-------------FR1-------------> CDR1<----FR2----->    CDR2     <----
EVQLQQSGAELVKPGASVKMSCKASVNIFTSYNMHWVKQTPGQGLEWIGGLHPGNGDTSYNQKFKGKATLT

--------FR3----------------> CDR3 <----FR3---->
ADKSSSTAYMQVSMLTSEDSAVYYCVLTTAGRAWFAYWGQGTLVTVSA

-continued (SEQ ID NO: 125)
Nucleic acid sequence
GAGGTTCAACTGCAGCAGTCTGGGGCTGAGCTGGTGAAGCCTGGGGCCTCAGTGAAGATGTCTTG
CAAGGCTTCTGTCAACATATTTACCAGTTACAATATGCACTGGGTAAAACAGACACCTGGACAGG
GCCTGGAATGGATTGGAGGTCTTCATCCAGGAAATGGTGATACTTCCTACAATCAGAACTTCAAA
GGCAAGGCCACATTGACTGCAGACAAATCCTCCAGCACTGCCTACATGCAGGTCAGCAACCTGAC
ATCTGAGGACTCTGCGGTCTATTACTGTGTCCTTACTACGGCTGGCCGGGCCTGGTTTGCTTACT
GGGGCCAAGGGACTCTGGTCACTGTCTCTGCA (SEQ ID NO: 126-129)
Light chain
<----------FR1--------->    CDR1    <-----FR2-----> CDR2   <---------------
DIQMTQSTSSLSASLGDRVTISCRASQDISNYLNWYQQKPDGTIKLLIYYTSRLHSGVPSRFSGSGSGTDY

FR3-------------->   CDR3  <---PR3--->
SLTISNLEEEDIATYFCQQGNTLPWTFGGGTKLEIK (SEQ ID NO: 130)
Nucleic acid sequence
GACATCCAGATGACACAGTCTACATCCTCCCTGTCTGCCTCTCTGGGAGACAGAGTCACCATCAG
CTGCAGGGCAAGTCAGGACATTAGCAATTATTTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA Clone 34H11:
(SEQ ID NO: 131-134)
Heavy chain
<-------------FR1------------->  CDR1<----FR2----->      CDR2      <----
QVQLQESGAELVKPGASVKMSCKASVNTFTGYNMHWVKQTPGQGLEWIGGLHPGNGDTSYNQKFKGKATLT --------FR3---------------->    CDR3  <----FR3---->
ADRSSNTAYMQLSSLTSEDSAVYYCALTTAGRAWFAYWGQGTLVTVSA (SEQ ID NO: 135)
Nucleic acid sequence
CAGGTGCAGCTGCAGGAGTCTGGGGCTGAACTGGTGAAGCCTGGGGCCTCAGTGAAGATGTCCTG
CAAGGCTTCTGTCAACACATTTACCGGTTACAATATGCACTGGGTAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA (SEQ ID NO: 136-139)
Light chain
<----------FR1--------->    CDR1    <-----FR2-----> CDR2   <---------------
DIQMTQTTSSLSASLGDRVTISCRASQDISNYLNWYQQKPDGTVKLLIYYTSRLHSGVPSRFSGSGSGTDY

FR3-------------->   CDR3  <---PR3--->
SLTISNLEEEDIATYFCQQGNTLPWTFGGGTKLEIK (SEQ ID NO: 140)
Nucleic acid sequence
GATATCCAGATGACACAGACTACATCCTCCCTGTCTGCCTCTCTGGGAGACAGAGTCACCATCAG
TTGCAGGGCAAGTCAGGACATTAGCAATTATTTAAACTGGTATCAGCAGAAACCAGATGGAACTG
TTAAACTCCTGATCTACTACACATCAAGATTACACTCAGGAGTCCCATCAAGGTTCAGTGGCAGT
GGGTCTGGAACAGATTATTCTCTCACCATTAGCAACCTGGAACAAGAAGATGTTGCCACTTACTT
TTGCCAACAGGGTAATACGCTTCCGTGGACGTTCGGTGGAGGCAGGAAGCTGGAAATAAA Clone 35D5:
(SEQ ID NO: 141-144)
Heavy chain
<-------------FR1------------->  CDR1<----FR2----->      CDR2      <----
QVQLKQSGAELVKPGASVKMSCKASVNTFTGYNMHWVKQTPGQGLEWIGGLHPGNGDTSYNQKFKGKATLT --------FR3---------------->    CDR3  <----FR3---->
ADKSSNTAYMQLSSLTSEDSAVYYCALTTAGRAWFAYWGQGTLVTVSA (SEQ ID NO: 145)
Nucleic acid sequence
CAGGTCCAGCTGAAGCAGTCTGGGGCTGAACTGGTGAAGCCTGGGGCCTCAGTGAAGATGTCCTG
CAAGGCTTCTGTCAACACATTTACCGGTTACAATATGCACTGGGTAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA -continued (SEQ ID NO: 146-149)
Light chain
<----------FR1-------->    CDR1    <-----FR2-----> CDR2   <---------------
DIQMTQSTSSLSASLGDRVTISCRASQDISNYLNWYQQKPDGTVKLLIYYTSRLHSGVPSRFSGSGSGTDY

FR3------------->    CDR3  <---PR3--->
SLTISNLEEEDIATYFCQQGNTLPWTFGGGTKLEIK (SEQ ID NO: 150)
Nucleic acid sequence
GACATCCAGATGACACAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA Clone 35A7:
(SEQ ID NO: 151-154)
Heavy chain
<-------------FR1-------------> CDR1<----FR2----->     CDR2     <----
QVQLKQSGAELVKPGASVKMSCKASVNTFTGYNMHWIKQTPGQGLEWIGGLHPGNGDTSYNQKFKGKATLT --------FR3---------------->    CDR3   <----FR3---->
ADKSSNTAYMQLSSLTSEDSAVYYCALTTAGRAWFAYWGQGTLVTVSA (SEQ ID NO: 155)
Nucleic acid sequence
CAGGTCCAGCTGAAGCAGTCTGGGGCTGAACTGGTGAAGCCTGGGGCCTCAGTGAAGATGTCCTG
CAAGGCTTCTGTCAACACATTTACCGGTTACAATATGCACTGGGTAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA (SEQ ID NO: 156-159)
Light chain
<----------FR1-------->    CDR1    <-----FR2-----> CDR2   <---------------
DIQMNQSTSSLSASLGDRVTISCRASQDISNYLNWYQQKPDGTIKLLIYYTSRLYSGVPSRFSGSGSGTDY

FR3------------->    CDR3  <---PR3--->
SLTISNLEEEDIATYFCQQGNTLPYTFGGGTKLEIK (SEQ ID NO: 160)
Nucleic acid sequence
GACATCCAGATGACACAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCGTGGACGTTCGGTGGAGGCACCAGACTGGAAATCAAA Clone 36F4:
(SEQ ID NO: 161-164)
Heavy chain
<-------------FR1-------------> CDR1<----FR2----->     CDR2     <----
QVQLQQSGAELVKPGASVKMSCKASVNTITGYNMHWVKQTPGQGLEWIGGLHPGNGDTSYNQKFKDKATLT --------FR3---------------->    CDR3   <----FR3---->
ADKSSNTAYMQLSSLTSEDSAVYYCALTTAGRAWFAYWGQGTLVTVSA (SEQ ID NO: 165)
Nucleic acid sequence
CAGGTCCAGCTGCAGCAGTCTGGGGCTGAACTGGTGAAGCCTGGGGCCTCAGTGAAGATGTCCTG
CAAGGCTTCTGTCAACACATTTACCGGTTACAATATGCACTGGGTAAAGCAGACACCTGGACAGG
GCCTGGAATGGATTGGAGGTCTTCATCCAGGAAATGGTGATACTTCCTACAATCAGAAGTTCAAA
GGCAAGGCCACATTGACTGCAGACAAATCCTCCAACACTGCCTACATGCAGCTCAGCAGCCTGAC
ATCTGAGGACTCTGCGGTCTATTACTGTGCCCTTACTACGGCTGGCCGGGCCTGGTTTGCTTACT
GGGGCCAAGGGACTCTGGTCACTGTCTCTGCA (SEQ ID NO: 166-169)
Light chain
<----------FR1-------->    CDR1    <-----FR2-----> CDR2   <---------------
DIKMTQSTSSLSASLGDRVTTSCRASQDISNYLNWYQQKPDGTVKLLIYYTSRLHSGVPSRFSGSGSGTDY

FR3------------->    CDR3  <---PR3--->
SLTISNLEEEDIATYFCQQGNTLPPWTFGGGTKLEIK (SEQ ID NO: 170)
GACATCAAGATGACCCAGTCTACATCCTCCCTGTCTGCCTCTCTGGGAGACAGAGTCACCATCAG
CTGCAGGGCAAGTCAGGACATTAGCAATTATTTAAACTGGTATCAGCAGAAACCAGATGGAACTG
TTAAACTCCTGATCTACTACACATCAAGATTATACTCAGGAGTCCCATCAAGGTTCAGTGGCAGT
GGGTCTGGAACAGATTATTCTCTCACCATTAGCAACCTGGAACAAGAACATATTGCCACTTACTT
TTGCCAACAGGGTAATACGCTTCCTCCGTGGACGTTCGGTGGAGGCACCAGACTGGAAATCAAA

6. Construction of Chimeric Antibody Expression Vector

The variable region sequence fragments of the heavy and light chains described above are PCR amplified, and the heavy chain variable region is cloned into a vector containing the human heavy chain constant region and regulatory elements to express the entire IgG heavy chain in mammalian cells. Similarly, the light chain variable region is cloned into a vector containing the human light chain constant region and regulatory elements to express the entire IgG light chain in mammalian cells. After correct sequencing, the vector is transfected into HEK293-6E mammalian cells, and IgG is secreted into the culture medium by expression, and the supernatant is pooled and collected, and purified by filtration. The IgG is purified by Protein A chromatography, and the culture supernatant is loaded onto a Protein A column with proper size and washed with 50 mM Tris-HCl (pH 8.0) and 250 mM NaCl, and the bound IgG is eluted off with 0.1 M Glycine-HCl (pH 3.0). The protein is concentrated by ultrafiltration using a concentrating tube (Millipore), OD280 is detected, and the concentration of IgG is determined spectrophotometrically. The aggregation or degradation of purified IgG is analyzed by SDS-PAGE.

7. Fortebio Assay of Antibody Affinity

PBS is added to any column of the 96-well plate, 100 ul/well, and the 96-well plate is placed in the probe holder cassette. When taking the probe, be careful to completely hang it on the holder to prevent the probe from touching the holder. The immobilized biotin-labeled hIL-4Rα is diluted to 5 ug/ml with PBS; a new 96-well plate is taken, and the diluted immobilized material is added column by column, 100 ul/well. The antibody is diluted to 50 ug/ml with PBS and then diluted at 1:1 to prepare 6 concentration series: 50 ug/ml, 25 ug/ml, 12.5 ug/ml, 6.25 ug/ml, 3.125 ug/ml, 0 ug/ml, with 100 ul per well, which amount can be appropriately adjusted depending on the binding ability of the specific analyte. A new 96-well plate is taken, and PBS is added to columns 1 and 2, 100 ul/well (the same buffer for both baseline and dissociation); the diluted immobilized material is added to column 3; the analyte diluted according to the series is added to column 4; 10 mM HCl (pH 1.9) is added to column 11; and PBS is added to column 12. The SA probe binds very strongly to the immobilized biotin material. When regenerated, the immobilized material is still bound to the probe, so it can be reused after immobilizing only once. Then the experimental method is set up in the Fortebio software, and then the experimental program is run for detection. The detection results of antibody affinity are as shown in Table 1 below.

TABLE 1

| No. | KD (nm) | kon (1/Ms) | kdis (1/s) |
|---|---|---|---|
| 31H7 | 9.6 | 2.66E+04 | 2.56E−04 |
| 31B9 | 1.9 | 3.30E+04 | 6.28E−05 |
| 34A2 | 0.001 | 2.90E+04 | 1.00E−07 |
| 34H11 | 6.6 | 2.69E+04 | 1.76E−04 |
| 35D5 | 1.3 | 3.87E+04 | 5.05E−05 |
| 35A7 | 0.001 | 2.47E+04 | 1.00E−07 |
| 36F4 | 1.8 | 5.09E+04 | 9.37E−05 |
| 24G10 | 0.94 | 2.53E+04 | 2.37E−05 |
| 25D6 | 5.9 | 2.65E+04 | 1.57E−04 |
| 25G9 | 0.001 | 3.79E+04 | 1.00E−07 |
| 1D8 | 8.06 | 7.01E+04 | 5.66E−04 |
| 2H1 | 5.27 | 7.16E+04 | 3.77E−04 |
| 1B6 | 20.78 | 2.46E+04 | 5.10E−04 |
| 1A6 | 11.3 | 5.30E+04 | 6.02E−04 |
| 1H9 | 8.9 | 2.93E+04 | 2.62E−04 |
| 2F8 | 0.9 | 2.93E+04 | 8.68E−06 |

8. Humanization of Antibodies

The selected monoclonal antibody variable region sequence is aligned with the germline sequences of human antibodies to find a sequence with high homology for CDR grafting; then, a computer is used to perform homology modeling, amino acid sequences of the CDR region and its surrounding framework are analyzed, and their spatial stereoscopic combination is investigated. By calculating electrostatic force, van der Waals force, hydrophilicity and entropy, the key amino acid individuals that may interact with IL-4Rα and maintain the spatial framework in the gene sequence of the positive monoclonal antibody are analyzed, and reversion mutation sites are designed on this basis. The HLA-DR affinity is analyzed and investigated to select a human embryonic framework sequence with low immunogenicity.

A total of 8 heavy chain derivatives (VH1021 to VH1028) and 4 light chain derivatives (VL1011 to VL1014) are designed; the light and heavy chain derivatives are separately synthesized (SynbioTech, Suzhou, and GENE WIZ, Suzhou) and cloned into vectors pHCT2 and HCT1 containing the antibody kappa chain constant region Ckappa or the human IgG1 constant region CH1-CH3; the plasmids are matched and are used to transfect HEK293.6E cells for expression for 5-6 days; and the supernatant is taken and purified by protein A column.

Heavy chain variable region sequences of the humanized antibody:

(SEQ ID NO: 171-175)

```
VH1021:
<-------------FR1------------> CDR1<----FR2-----> CDR2 <----
EVQLVESGGGLVKPGGSLRLSCAASGFTFSRYAMSWVRQAPGKGLEWVSTISSGGSYTNYADSVKGRFTIS

--------FR3---------------> CDR3 <----FR3---->
RDNVKNTLYLQMNSLRAEDTAVYYCARATARATEFAYWGQGTLVTVSS

Nucleic acid sequence
GAGGTGCAGCTGGTTGAATCTGGCGGAGGACTGGTTAAGCCTGGCGGCTCTCTGAGACTGTCTTG
TGCCGCTTCTGGCTTCACCTTCAGCAGATACGCCATGAGCTGGGTCCGACAGGCTCCTGGCAAAG
GACTGGAATGGGTGTCCACAATCAGCAGCGGCGGCAGCTACACAAACTACGCCGATAGCGTGAAG
GGCAGATTCACCATCTCCAGAGACAACGTGAAGAACACCCTGTACCTGCAGATGAACAGCCTGAG
AGCCGAGGACACCGCCGTGTACTACTGTGCCAGAGCCACAGCCAGAGCTACCGAGTTTGCTTACT
GGGGCCAGGGCACACTGGTCACCGTTTCTTCT
```

(SEQ ID NO: 179-180)
VH1022:
```
<-------------FR1-------------> CDR1<----FR2-----> 	    CDR2		<----
EVQLLESGGGLVQPGGSLRLSCAASGFTFSRYAMSWVRQAPGKGLEWVSTISSGGSYTNYADSVKGRFTIS

--------FR3----------------> 	CDR3 <----PR3---->
RDNVKNTLYLQMNSLRAEDTAVYYCARATARATEFAYWGQGTLVTVSS

Nucleic acid sequence
GAGGTGCAGCTGCTGGAATCTGGCGGAGGACTGGTTAAGCCTGGCGGCTCTCTGAGACTGTCTTG
TGCCGCTTCTGGCTTCACCTTCAGCAGATACGCCATGAGCTGGGTCCGACAGGCTCCTGGCAAAG
GACTGGAATGGGTGTCCACAATCAGCAGCGGCGGCAGCTACACAAACTACGCCGATAGCGTGAAG
GGCAGATTCACCATCTCCAGAGACAACGTGAAGAACACCCTGTACCTGCAGATGAACAGCCTGAG
AGCCGAGGACACCGCCGTGTACTACTGTGCCAGAGCCACAGCCAGAGCTACCGAGTTTGCTTACT
GGGGCCAGGGCACACTGGTCACCGTTTCTTCT
```

(SEQ ID NO: 181-185)
VH1023:
```
<-------------FR1-------------> CDR1<----FR2----->        CDR2        <----
QVQLVQSGAELKKPGASVKVSCKASGNTFTGYNMHWIQQSPGQGLEWMGGLHPGNGDSSYNQKFQGRVTLT

--------FR3---------------->   CDR3 <----PR3---->
ADKSSNTAYMELSSLRSEDSAVYYCALTTAGRAWFPYWGQGTLVTVSS

Nucleic acid sequence
CAGGTTCAGCTGGTTCAGTCTGGCGCCGAAGTGAAGAAACCTGGCGCCTCTGTGAAGGTGTCCTG
CAAGGCTAGCGGCAACACATTCACCGGCTACAACATGCATTGGATCCAGCAGAGCCCTGGACAGG
GCCTCGAATGGATGGGAGGACTGCATCCTGGCAACGGCGACAGCAGCTACAACCAGAAATTCCAG
GGCAGAGTGACCCTGACCGCCGACAAGTCTAGCAACACCGCCTACATGGAACTGAGCAGCCTGAG
AAGCGAGGACACCGCCGTGTACTACTGTGCCCTTACAACAGCCGGCAGAGCCTGGTTTCCTTACT
GGGGACAGGGAACCCTGGTCACCGTTAGCTCT
```

(SEQ ID NO: 186-190)
VH1024:
```
<-------------FR1-------------> CDR1<----FR2----->        CDR2        <----
QVQLVQSGAEVKKPGASVKMSCKASVYTFTGYNMHWIQQSPGQGLEWMGGLHPGNGDSSYNQKFQGRATLT

--------FR3---------------->   CDR3 <----PR3---->
ADKSSNTAYMELSSLRSEDSAVYYCALTTAGRAWFPYWGQGTLVTVSS

Nucleic acid sequence
CAGGTTCAGCTGGTTCAGTCTGGCGCCGAAGTGAAGAAACCTGGCGCCTCTGTGAAGGTGTCCTG
CAAGGCTAGCGGCAACACATTCACCGGCTACAACATGCATTGGATCCAGCAGAGCCCTGGACAGG
GCCTCGAATGGATGGGAGGACTGCATCCTGGCAACGGCGACAGCAGCTACAACCAGAAATTCCAG
GGCAGAGTGACCCTGACCGCCGACAAGTCTAGCAACACCGCCTACATGGAACTGAGCAGCCTGAG
AAGCGAGGACACCGCCGTGTACTACTGTGCCCTTACAACAGCCGGCAGAGCCTGGTTTCCTTACT
GGGGACAGGGAACCCTGGTCACCGTTAGCTCT
```

(SEQ ID NO: 191-195)
VH1025:
```
<-------------FR1-------------> CDR1<----FR2----->        CDR2        <----
QVQLVQSGAEVKKPGASVKVSCKASGNIFTGYNMHWVRQAPGQGLEWMGGLHPGNGDSSYNQKFQGRVTLT

--------FR3---------------->   CDR3 <----PR3---->
ADKSSNTAYMELSSLRSEDSAVYYCALTTAGRAWFAYWGQGTLVTVSS

Nucleic acid sequence
GAGGTGCAGCTGCTGGAATCTGGCGGAGGACTGGTTAAGCCTGGCGGCTCTCTGAGACTGTCTTG
TGCCGCTTCTGGCTTCACCTTCAGCAGATACGCCATGAGCTGGGTCCGACAGGCTCCTGGCAAAG
GACTGGAATGGGTGTCCACAATCAGCAGCGGCGGCAGCTACACAAACTACGCCGATAGCGTGAAG
GGCAGATTCACCATCTCCAGAGACAACGTGAAGAACACCCTGTACCTGCAGATGAACAGCCTGAG
AGCCGAGGACACCGCCGTGTACTACTGTGCCAGAGCCACAGCCAGAGCTACCGAGTTTGCTTACT
GGGGCCAGGGCACACTGGTCACCGTTTCTTCT
```

(SEQ ID NO: 196-200)
VH1026:
```
<-------------FR1-------------> CDR1<----FR2----->        CDR2        <----
QVQLVQSGAEVKKPGASVKMSCKASVYTFTGYNMHWVRQAPGQGLEWIGGLHPGNGDSSYNQKFQGRATLT

--------FR3---------------->   CDR3 <----PR3---->
ADKSSNTAYMELSSLRSEDSAVYYCALTTAGRAWFAYWGQGTLVTVSS

Nucleic acid sequence
CAGGTTCAGCTGGTTCAGTCTGGCGCCGAAGTGAAGAAACCTGGCGCCTCTGTGAAGGTGTCCTG
CAAGGCTAGCGGCAACACATTCACCGGCTACAACATGCATTGGATCCAGCAGAGCCCTGGACAGG
GCCTCGAATGGATGGGAGGACTGCATCCTGGCAACGGCGACAGCAGCTACAACCAGAAATTCCAG
GGCAGAGTGACCCTGACCGCCGACAAGTCTAGCAACACCGCCTACATGGAACTGAGCAGCCTGAG
AAGCGAGGACACCGCCGTGTACTACTGTGCCCTTACAACAGCCGGCAGAGCCTGGTTTCCTTACT
GGGGACAGGGAACCCTGGTCACCGTTAGCTCT
```

-continued (SEQ ID NO: 201-205)

VH1027:
```
<-------------FR1-------------> CDR1<----FR2----->       CDR2       <----
EVQLVQSGAEVKKPGATVKISCKASGNIFTSYNMHWVRQAPGQGLEWMGGLHPGNGDTSYNQKFQGRVTLT

--------FR3---------------->   CDR3 <----FR3---->
ADKSSSTAYMELSSLRSEDTAVYYCVLTTAGRAWFAYWGQGTLVTVSS
```

Nucleic acid sequence
```
GAAGTGCAGCTGGTTCAGTCTGGCGCCGAAGTGAAGAAACCTGGCGCCACCGTGAAGATCAGCTG
CAAGGCTAGCGGCAACATCTTCACCAGCTACAACATGCACTGGGTCCGACAGGCCCCTGGACAGG
GACTTGAATGGATGGGAGGACTGCACCCTGGCAACGGCGACACAAGCTACAACCAGAAATTCCAG
GGCAGAGTGACCCTGACCGCCGACAAGTCTAGCAGCACCGCCTACATGGAACTGAGCAGCCTGAG
AAGCGAGGACACCGCCGTGTACTACTGTGCCCTTACAACAGCCGGCAGAGCCTGGTTTCCTTACT
GGGGCCAGGGAACCCTGGTCACCGTTTCTTCT
```

(SEQ ID NO: 206-210)

VH1028:
```
<-------------FR1-------------> CDR1<----FR2----->       CDR2       <----
EVQLVQSGAEVKKPGATVKMSCKASVYTFTSYNMHWVRQAPGQGLEWIGGLHPGNGDTSYNQKFKGRATLT

--------FR3---------------->   CDR3 <----FR3---->
ADKSSSTAYMELSSLRSEDTAVYYCVLTTAGRAWFAYWGQGTLVTVSS
```

Nucleic acid sequence
```
GAAGTGCAGCTGGTTCAGTCTGGCGCCGAAGTGAAGAAACCTGGCGCCACCGTGAAGATCAGCTG
CAAGGCTAGCGGCAACATCTTCACCAGCTACAACATGCACTGGGTCCGACAGGCCCCTGGACAGG
GACTTGAATGGATGGGAGGACTGCACCCTGGCAACGGCGACACAAGCTACAACCAGAAATTCCAG
GGCAGAGTGACCCTGACCGCCGACAAGTCTAGCAGCACCGCCTACATGGAACTGAGCAGCCTGAG
AAGCGAGGACACCGCCGTGTACTACTGTGCCCTTACAACAGCCGGCAGAGCCTGGTTTCCTTACT
GGGGCCAGGGAACCCTGGTCACCGTTTCTTCT
```

Light chain variable region sequences of the humanized antibody:

(SEQ ID NO: 211-215)

VL1011:
```
<----------FR1--------->     CDR1    <-----FR2-----> CDR2 <--------------
DIQMTQSPSSLSASVGDRVTITCQASQDISNYLNWYQQKPGKAPKLLIYYTSRLHSGVPSRFSGSGSGTDY

FR3-------------->    CDR3 <---PR3--->
TFTISSLQPEDIATYFCQQGNTLPWTFGGGTKVEIK
```

Nucleic acid sequence
```
GACATCCAGATGACACAGAGCCCTAGCAGCCTGTCTGCCAGCGTGGGAGACAGAGTGACCATCAC
CTGTCAGGCCAGCCAGGACATCAGCAACTACCTGAACTGGTATCAGCAGAAGCCCGGCAAGGCCC
CTAAGCTGCTGATCTACTACACCAGCAGACTGCACAGCGGCGTGCCCTCTAGATTTTCTGGCAGC
GGCTCTGGCACCGACTACACCTTCACAATCAGCAGCCTGCAGCCTGAGGATATCGCTACCTACTT
CTGCCAGCAAGGCAACACCCTGCCTTGGACATTTGGCGGAGGCACCAAGGTGGAAATCAAG
```

(SEQ ID NO: 216-220)

VL1012:
```
<----------FR1--------->     CDR1    <-----FR2-----> CDR2 <--------------
DIQMTQSPSSLSASVGDRVTITCRASQDISNYLNWYQQKPGKAPKLLIYYTSRLHSGVPSRFSGSGSGTDY

FR3-------------->    CDR3 <---PR3--->
TLTISSLQPEDFATYFCQQGNTLPWTFGGGTKVEIK
```

Nucleic acid sequence
```
GACATCCAGATGACACAGAGCCCTAGCAGCCTGTCTGCCAGCGTGGGAGACAGAGTGACCATCAC
CTGTCAGGCCAGCCAGGACATCAGCAACTACCTGAACTGGTATCAGCAGAAGCCCGGCAAGGCCC
CTAAGCTGCTGATCTACTACACCAGCAGACTGCACAGCGGCGTGCCCTCTAGATTTTCTGGCAGC
GGCTCTGGCACCGACTACACCTTCACAATCAGCAGCCTGCAGCCTGAGGATATCGCTACCTACTT
CTGCCAGCAAGGCAACACCCTGCCTTGGACATTTGGCGGAGGCACCAAGGTGGAAATCAAG
```

(SEQ ID NO: 221-225)

VL1013:
```
<----------FR1--------->     CDR1    <-----FR2-----> CDR2 <--------------
DIQMTQSPSSLSASVGDRVTITCQASQDISNYLNWYQQKPGKAPKLLIYYTSRLHSGVPSRFSGSGSGTDY

FR3-------------->    CDR3 <---PR3--->
TLTISSLQPEDFATYFCQQGNTLPLTFGGGTKVEIK
```

```
                                                           (SEQ ID NO: 226-230)
Nucleic acid sequence
GACATCCAGATGACACAGAGCCCTAGCAGCCTGTCTGCCAGCGTGGGAGACAGAGTGACCATCAC
CTGTCAGGCCAGCCAGGACATCAGCAACTACCTGAACTGGTATCAGCAGAAGCCCGGCAAGGCCC
CTAAGCTGCTGATCTACTACACCAGCAGACTGCACAGCGGCGTGCCCTCTAGATTTTCTGGCAGC
GGCTCTGGCACCGACTACACCTTCACAATCAGCAGCCTGCAGCCTGAGGATATCGCTACCTACTT
CTGCCAGCAAGGCAACACCCTGCCTTGGACATTTGGCGGAGGCACCAAGGTGGAAATCAAG VL1014:
<---------FR1--------->    CDR1    <-----FR2-----> CDR2   <---------------
DIQMTQSPSSLSASVGDRVTITCQASQDISNYLNWYQQKPGKAPKLLIYYTSRLHSGVPSRFSGSGSGTDY FR3-------------->    CDR3   <---PR3--->
TLTISSLQPEDFATYFCQQGNTLPWTFGGGTKVEIK Nucleic acid sequence
GACATCCAGATGACACAGAGCCCTAGCAGCCTGTCTGCCAGCGTGGGAGACAGAGTGACCATCAC
CTGTCAGGCCAGCCAGGACATCAGCAACTACCTGAACTGGTATCAGCAGAAGCCCGGCAAGGCCC
CTAAGCTGCTGATCTACTACACCAGCAGACTGCACAGCGGCGTGCCCTCTAGATTTTCTGGCAGC
GGCTCTGGCACCGACTACACCTTCACAATCAGCAGCCTGCAGCCTGAGGATATCGCTACCTACTT
CTGCCAGCAAGGCAACACCCTGCCTTGGACATTTGGCGGAGGCACCAAGGTGGAAATCAAG
```

9. FACS Analysis for Binding of Candidate Humanized Antibodies to IL-4Rα

9.1 FACS Analysis for Binding of Candidate Humanized Antibodies to Stably Transfected Cell Line of HEK293-IL-4Rα

Figure 5A:
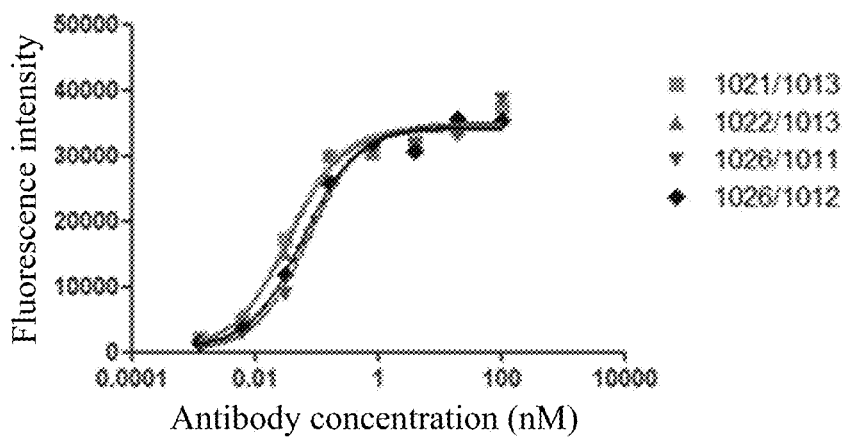
FIG. 5A shows that the humanized candidate antibodies can specifically bind to stably-transfected HEK293 cells expressing IL-4Rα.

In order to further verify the binding of candidate humanized antibodies to IL-4Rα by FACS, HEK293 cells and 293-hIL-4Rα stably transfected cells are prepared with 5*10⁴ cells per well; 5 ml of 0.5% BSA/PBS is added and centrifuged at 1000 rpm for 3 minutes, and washed 3 times. Every 1*10⁶ cells corresponds to 100 μl of 3% BSA/PBS solution, and the solution is blocked at 4° C. for 20 minutes. The prepared cells are added to a 96-well U-type plate at a volume of 100 μl/well, and centrifuged at 1100 rpm for 3 minutes, and the supernatant is discarded; and the primary antibody solution is added and incubated for 1 hour on ice. Purified Fab antibodies are made into a 5-concentration series with a starting concentration of 500 nM (12.5 μg/ml), and diluted according to a series of 1:5. After incubation with the primary antibody solution, additional 0.5% BSA/PBS is added to a volume of 150 μl, centrifuged at 1100 rpm for 3 minutes, and the supernatant is discarded. 150 μl of 0.5% BSA/PBS is further added, centrifuged at 1100 rpm for 3 minutes, and the supernatant is discarded; before adding a secondary antibody anti-human IgG, Fab'2-AF647, same is diluted at 1:300 with 1% BSA/PBS. 40 μl of the secondary antibody solution is added to each well and incubated on ice for 45 minutes. After incubation with the secondary antibody solution, additional 0.5% BSA/PBS is added to a volume of 150 μl, centrifuged at 1100 rpm for 3 minutes, and the supernatant is discarded; 150 μl of 0.5% BSA/PBS is further added, centrifuged at 1100 rpm for 3 minutes, and the supernatant is discarded; 20-100 μl of PBS is added to resuspend the cells to 1*10⁶ cells per ml, and the obtained suspension is loaded onto a flow cytometer (I-Que screener). After opening the instrument and operating system according to the correct process, and setting the correct parameters, the cells are loaded to the test plate, and the fluorescent signal is detected, analysis is performed using Graph Pad Prism 5 software. The results are as shown in FIG. 5A, showing that the humanized candidate antibodies are specifically bound to HEK293 stably transfected cells expressing IL-4Rα.

Figure 5B:
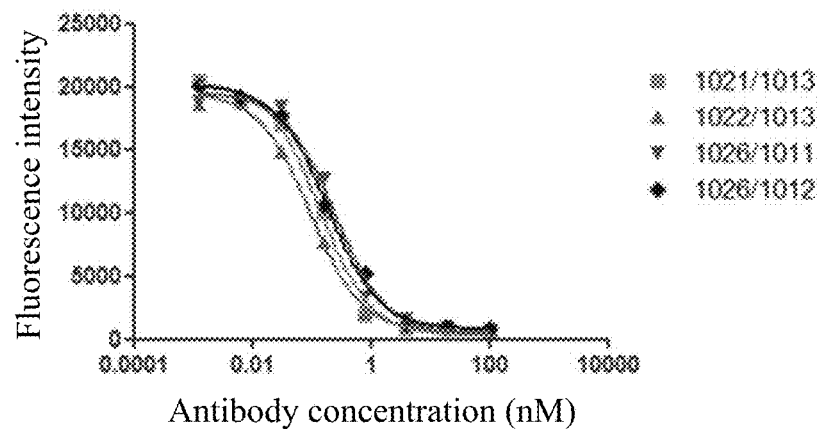
FIG. 5B shows that the candidate antibody can inhibit the binding of human IL-4 to cells expressing hIL-4Rα.

9.2 FACS Analysis for Inhibiting the Binding of Human IL-4 to HEK293-IL-4Rα Stably Transfected Cells by Humanized Candidate Antibodies HEK293 cells and 293-hIL-4Rα stably transfected cells are prepared with 3*10⁴ cells per well; 5 ml of 0.5% BSA/PBS is added and centrifuged at 1000 rpm for 3 minutes, and washed 3 times. Every 1*10⁶ cells corresponds to 100 μl of 3% BSA/PBS solution, and the solution is blocked at 4° C. for 20 minutes. The prepared cells are added to a 96-well U-type plate at a volume of 100 μl/well, and centrifuged at 1100 rpm for 3 minutes, and the supernatant is discarded; and the primary antibody solution is added and incubated for 1 hour on ice. Purified candidate antibodies are made into 5 concentration series with a starting concentration of 100 nM, and diluted according to a series of 1:5. After incubation with the primary antibody solution, additional 0.5% BSA/PBS is added to a volume of 150 μl, centrifuged at 1100 rpm for 3 minutes, and the supernatant is discarded. 150 μl of 0.5% BSA/PBS is further added, centrifuged at 1100 rpm for 3 minutes, and the supernatant is discarded; biotin-labeled IL-4 at a final concentration of 0.15 ug/ml is added and incubated on ice for 45 minutes. The secondary antibody SA-PE is diluted at 1:300 with 10% BSA/PBS; 40 μl of the secondary antibody solution is added to each well and incubated on ice for 45 minutes. After incubation with the secondary antibody solution, additional 0.5% BSA/PBS is added to a volume of 150 μl, centrifuged at 1100 rpm for 3 minutes, and the supernatant is discarded; 150 μl of 0.5% BSA/PBS is further added, centrifuged at 1100 rpm for 3 minutes, and the supernatant is discarded. 20-100 μl of PBS is added to resuspend the cells to 1*10⁶ cells per ml, and the obtained suspension is loaded onto a flow cytometer (I-Que screener). After opening the instrument and operating system according to the correct process, and setting the correct parameters, the cells are loaded to the test plate, and the fluorescent signal is detected, analysis is performed using Graph Pad Prism 5 software. The results are as shown in FIG. 5B, showing that the candidate antibodies can inhibit the binding of human IL-4 to cells expressing hIL-4Rα.

10. Inhibition of the Effect of hIL-4 or hIL-13 on the Proliferation of TF-1 Cells by Candidate Humanized Antibodies 10.1 Experiment of Stimulation of TF-1 Cell Proliferation by hIL-4 or hIL-13

The cryopreserved TF-1 cells (ATCC: CRL-2003™) are taken out from the liquid nitrogen tank and gently shaken in a water bath at 37° C. to dissolve same quickly. The dissolved cell suspension is transferred to a 50 ml centrifuge tube containing 10 ml of pre-warmed 1640 medium (Gibco, Cat: C11875500BT), and centrifuged at 1000 rpm for 3 min; the supernatant is discarded, 1640 complete medium containing GM-CSF is added and transferred to T75 cell culture flask, and placed in a 5% carbon dioxide cell incubator at 37° C. for static culture. The cell suspension is taken out every 2-3 days, and centrifuged at 800 rpm for 3 min; the cells are resuspended with addition of 15 ml of 1640 complete medium, and $1*10^6$ cells are taken and placed in T75 culture flask containing 10 ml of 1640 complete medium for 2-3 consecutive passages. When the cells are crystal clear, in a single and suspension state, and slightly irregular in morphology, and the cell viability is greater than 90%, the cell activity detection experiment is performed.

Figure 6A:
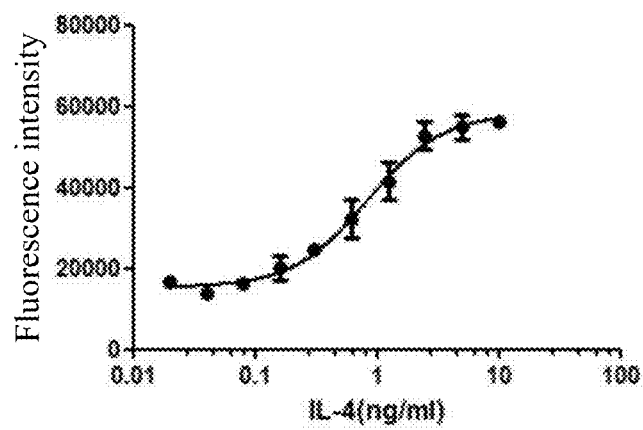
FIG. 6A shows that hIL-4 can stimulate TF-1 cell proliferation.
Figure 6B:
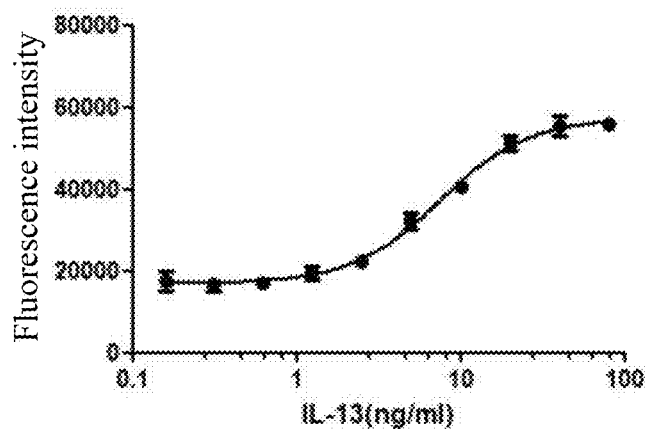
FIG. 6B shows that hIL-13 can stimulate TF-1 cell proliferation.

According to the experimental design, a cell solution containing $1.5\times10^6$ cells is prepared, centrifuged at 1000 rpm for 5 min, and then the supernatant is discarded; the cell pellet is resuspended with complete medium without GM-CSF, centrifuged at 1000 rpm for 5 min, and the supernatant is discarded, and the obtained cell pellet is resuspended with 4.2 ml of complete medium without GM-CSF. The sampling is counted by a microscope, and the cell liquid density is adjusted to $3\times10^5$ cells/ml based on the counting result. Then, the cell solution and the culture medium are added to a 96-well plate, 100 ul/well, 200 ul of PBS is added to the blank groups, and the plate is cultured in an incubator for 24 hours under the conditions of 37° C. and 5% $CO_2$. Firstly, hIL-4 (Sino Biological, Cat: 11846-HNAC) and hIL-13 (Sino Biological, Cat: 10369-HNAC) are diluted to 100 ng/ml and 800 ng/ml, respectively, then same is diluted 9 times in 2× series, and according to experiment design, the diluted IL-4 and IL-13 are added to the wells of the plate by a multichannel pipette with 10 ul per well, and uniformly mixed. The plate is returned to the incubator for further 72 hours, the plate is taken out, the cells are uniformly mixed with a multichannel pipette, and 80 ul of the cell solution is uniformly pipetted and added to the corresponding well of the 96-well black ELISA plate. Then 80 ul of Cell titer-Glo (Promega, Cat: G7570) dissolved and uniformly mixed in advance is added to each well, the 96-well black ELISA plate (JET, Cat: LTP-021-896) is then gently shaken on a shaker (Thermo, Cat: 8880024) for 2 minutes, and incubated for 10 min at room temperature to produce a stable luminescent signal. The luminescence is detected with an ELISA reader and the detection time is set to 1 second. The results are as shown in FIG. 6A and FIG. 6B, showing that hIL-4 can stimulate TF-1 cell proliferation and that hIL-13 can stimulate TF-1 cell proliferation, respectively.

Figure 6C:
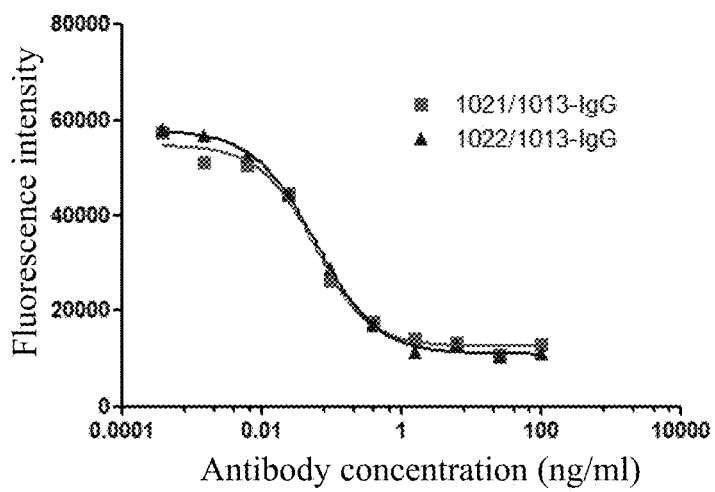
FIG. 6C shows that the humanized antibodies can inhibit hIL-4-stimulated TF-1 cell proliferation.
Figure 6D:
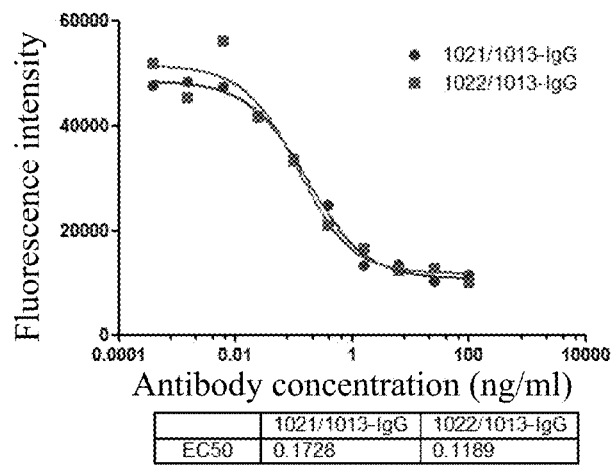
FIG. 6D shows that the humanized antibodies inhibit hIL-13-stimulated TF-1 cell proliferation.
Figure 6E:
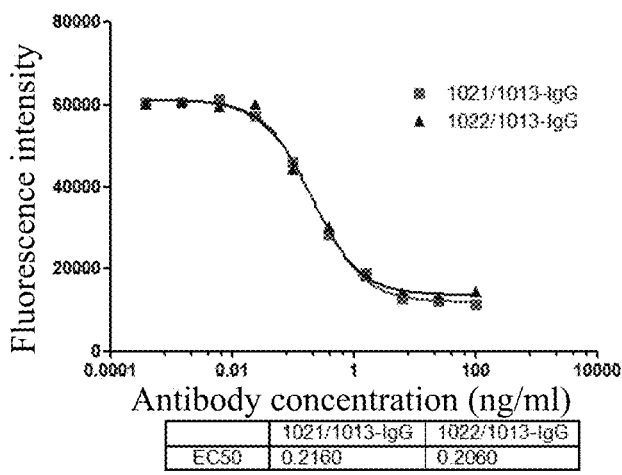
FIG. 6E shows that the humanized antibodies can simultaneously inhibit hIL-4-stimulated and hIL-13-stimulated TF-1 cell proliferation.

10.2 ELISA Detection for Inhibition of the Effect of hIL-4 or hIL-13 on the Proliferation of TF-1 Cells by Candidate Humanized Antibodies The TF-1 cells are cultured as described in 5.1, and 100 ul of cell solution ($3\times10^5$ cells/ml) is added to a 96-well plate according to the experimental design and cultured for 24 hours under conditions without any cytokines, and the edge holes are sealed with PBS. The antibody is diluted to a concentration of 1 mM, hIL-4 is diluted to 3 ng/ml, and hIL-13 is diluted to 30 ng/ml. The antibody is diluted in a 2× series and added to the cells with 10 ul/well, uniformly mixed, and incubated for 1 hour under the conditions of 37° C. and 5% $CO_2$; 10 ul of 1640 medium is added to the blank groups, uniformly mixed, and incubated for 1 hour under the conditions of 37° C. and 5% $CO_2$. According to the experimental design, hIL-4 and hIL-13 are added to the cells with 10 ul/well, uniformly mixed, and cultured for 72 hour under the conditions of 37° C. and 5% $CO_2$; 10 ul of 1640 medium is added to the blank groups, uniformly mixed, and cultured for 72 hour under the conditions of 37° C. and 5% $CO_2$. The uniformly mixed cell solution is inoculated into the 96-well black ELISA plate, 80 ul/well; 80 ul of Cell Titer-Glo is added to each well, and the microwell plate is then gently shaken and uniformly mixed on a shaker for 2 minutes, and incubated for 10 min at room temperature to produce a stable luminescent signal. The luminescence is detected with an ELISA reader and the detection time is set to 1 second. The results are as shown in FIG. 6C, FIG. 6D and FIG. 6E, showing that the humanized antibodies can inhibit hIL-4-stimulated TF-1 cell proliferation, the humanized antibodies can inhibit hIL-13-stimulated TF-1 cell proliferation, the humanized antibodies can simultaneously inhibit hIL-4-stimulated and hIL-13-stimulated TF-1 cell proliferation, respectively.

Figure 7A:
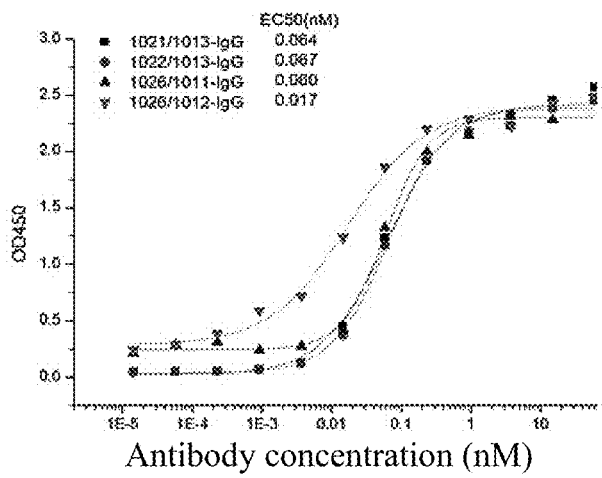
FIG. 7A shows that the humanized candidate antibodies bind to the human IL-4Rα protein.
Figure 7B:
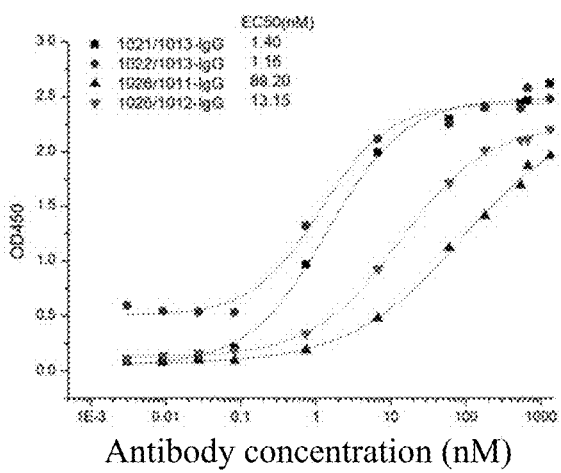
FIG. 7B shows the humanized candidate antibodies bind to the protein of cynomolgus monkey IL-4Rα.
Figure 7C:
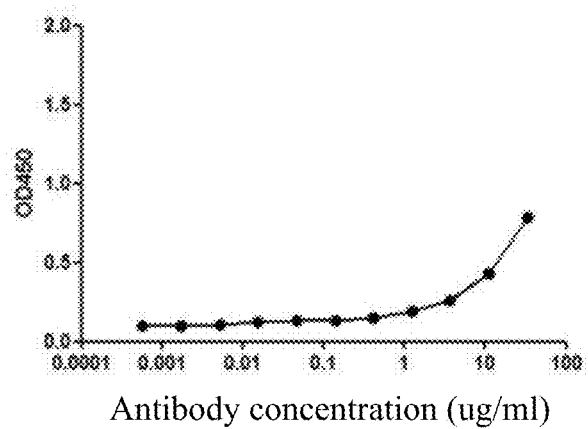
FIG. 7C shows that the candidate humanized antibodies does not bind to mouse IL-4Rα protein.
Figure 7D:
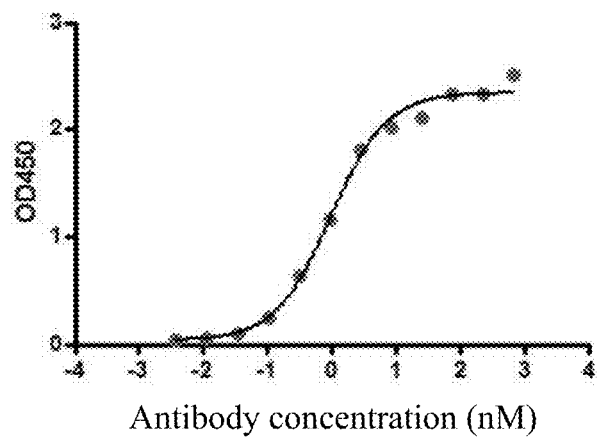
FIG. 7D shows that the humanized candidate antibodies bind to rat IL-4Rα protein.

11. Binding of Humanized Candidate Antibodies to Cynomolgus, Mouse and Rat IL-4RαProteins 1 ug/ml human hIL-4Rα, 10 ug/ml cynomolgus cynoIL-4Rα, 1 ug/ml mouse mIL-4Rα (Sino Biological, Cat: 80198-R08H) and 1 ug/ml rat-derived ratIL-4Rα (Sino Biological, Cat: 51180-M08H) are diluted in 0.05 M carbonate coating buffer (pH 9.5) at 4° C. overnight. The solution in the wells is discarded the next day and the wells are washed 3 times with PBS washing buffer. Then PBS solution containing 2% BSA is added for blocking for 2 hours. After washing 3 times with PBS washing buffer, 100 ul of humanized candidate antibodies at different diluted concentrations is added, incubated for 1 h at room temperature, and then washed 3 times with PBS washing buffer; the HRP cross-linked antibody (Jackson Immuno Research) is diluted at 1:10000 with PBS washing buffer and incubated for 1 hour at room temperature. After washing 3 times with PBS washing buffer, 100 ul of TMB substrate solution is added to develop color, and after reaction at room temperature for 10 minutes; the reaction is stopped by the addition of 50 ul of 0.5 M concentrated sulfuric acid solution and the absorbance at 450 nm is read. The results are: FIG. 7A shows that the humanized candidate antibodies bind to the human IL-4Rα protein; FIG. 7B shows the humanized candidate antibodies bind to the protein of cynomolgus monkey IL-4Rα; FIG. 7C shows that the candidate humanized antibodies does not bind to mouse IL-4Rα protein; FIG. 7D shows that the humanized candidate antibodies bind to rat IL-4Rα protein; it can be seen that humanized antibodies can bind to human or cynomolgus or rat IL-4Rα protein with similar affinity, but do not interact with mouse IL-4Rα protein.

The invention claimed is:

1. An antibody or a functional fragment thereof that specifically binds to IL-4Rα, wherein the antibody or functional fragment thereof comprises a heavy chain CDR1 selected from amino acid sequence SEQ ID NO: 172, a heavy chain CDR2 selected from amino acid sequence SEQ ID NO: 173, and a heavy chain CDR3 selected from amino acid sequence SEQ ID NO: 174; and a light chain CDR1 selected from amino acid sequence SEQ ID NO: 222, a light chain CDR2 selected from amino acid sequence SEQ ID NO: 223, and a light chain CDR3 selected from amino acid sequence SEQ ID NO: 224.

2. The antibody or functional fragment thereof according to claim 1, wherein the antibody or functional fragment thereof comprises a heavy chain variable region selected from amino acid sequence SEQ ID NO: 171, and a light chain variable region selected from amino acid sequence SEQ ID NO: 221.

3. The antibody or functional fragment thereof according to claim 1, wherein the antibody or functional fragment thereof inhibits the interaction of hIL-4 with hIL-4Rα; preferably, the antibody or functional fragment thereof also inhibits the binding of hIL-4Rα to a complex hIL-13Rα/hIL-13; and optionally, the antibody or functional fragment thereof is humanized.

4. The antibody or functional fragment thereof according to claim 1, wherein the antibody or a functional fragment thereof comprises a heavy chain variable region selected from amino acid sequence SEQ ID NO: 176, and a light chain variable region selected from amino acid sequence SEQ ID NO: 221.

5. The antibody or functional fragment thereof according to claim 1, wherein the antibody or functional fragment thereof comprises a heavy chain variable region selected from amino acid sequence SEQ ID NO: 196, and a light chain variable region selected from amino acid sequence SEQ ID NO: 211.

6. The antibody or functional fragment thereof according to claim 1, wherein the antibody or functional fragment thereof comprises a heavy chain variable region selected from amino acid sequence SEQ ID NO: 196, and a light chain variable region selected from amino acid sequence SEQ ID NO: 216.

7. A method of treating an allergy, asthma, or chronic obstructive pulmonary disease, comprising administering to a mammalian patient in need thereof the antibody or functional fragment thereof according to claim 1.

8. The method according to claim 7, wherein the antibody or functional fragment thereof comprises a heavy chain variable region selected from amino acid sequence SEQ ID NO: 171, and a light chain variable region selected from amino acid sequence SEQ ID NO: 221.

9. The method according to claim 7, wherein the antibody or functional fragment thereof comprises a heavy chain variable region selected from amino acid sequence SEQ ID NO: 176, and a light chain variable region selected from amino acid sequence SEQ ID NO: 221.

10. The method according to claim 7, wherein the antibody or functional fragment thereof comprises a heavy chain variable region selected from amino acid sequence SEQ ID NO: 196, and a light chain variable region selected from amino acid sequence SEQ ID NO: 211.

11. The method according to claim 7, wherein the antibody or functional fragment thereof comprises a heavy chain variable region selected from amino acid sequence SEQ ID NO: 196, and a light chain variable region selected from amino acid sequence SEQ ID NO: 216.

\* \* \* \* \*